United States Patent
Hadley et al.

(10) Patent No.: US 6,605,607 B1
(45) Date of Patent: Aug. 12, 2003

(54) TETRAHYDROBENZAZEPINE DERIVATIVES USEFUL AS MODULATORS OF DOPAMINE $D_3$ RECEPTORS (ANTIPSYCHOTIC AGENTS)

(75) Inventors: Michael Stewart Hadley, Sawbridgeworth (GB); Christopher Norbert Johnson, Saffron Walden (GB); Gregor James MacDonald, Trumpington (GB); Geoffrey Stemp, Bishops Stortford (GB); Antonio Kuok Keong Vong, Sawbridgeworth (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/806,902

(22) PCT Filed: Oct. 6, 1999

(86) PCT No.: PCT/EP99/07763

§ 371 (c)(1),
(2), (4) Date: Jul. 16, 2001

(87) PCT Pub. No.: WO00/21951

PCT Pub. Date: Apr. 20, 2000

(30) Foreign Application Priority Data

| Oct. 8, 1998 | (GB) | 9821976 |
|---|---|---|
| Nov. 6, 1998 | (GB) | 9824340 |
| May 7, 1999 | (GB) | 9910711 |
| Jul. 30, 1999 | (GB) | 9918032 |

(51) Int. Cl.[7] .................... A61K 31/55; A61P 25/18; C07D 223/16
(52) U.S. Cl. .................... 514/217.01; 540/594
(58) Field of Search .................... 514/217.01; 540/594

(56) References Cited

U.S. PATENT DOCUMENTS

| 4,220,778 A | 9/1980 | Ellefson et al. ............ 546/150 |
| 4,925,850 A | 5/1990 | George et al. ............ 514/307 |
| 5,294,621 A | 3/1994 | Russell .................... 514/301 |
| 5,350,754 A | 9/1994 | Crawley et al. ............ 514/277 |
| 5,414,010 A | 5/1995 | Downing et al. ............ 514/316 |
| 5,478,934 A | 12/1995 | Yuan et al. .................... 540/546 |
| 5,532,240 A | 7/1996 | Nakao et al. ............ 514/254 |
| 5,633,376 A | 5/1997 | Thurkauf et al. ............ 544/360 |
| 5,688,950 A | 11/1997 | Chen et al. .................... 544/354 |
| 5,891,877 A | 4/1999 | Brocchini et al. ....... 514/235.8 |

FOREIGN PATENT DOCUMENTS

| DE | 4425146 | 1/1996 |
| DE | 19728996 | 1/1999 |
| EP | 0 007 070 | 1/1980 |
| EP | 051 190 A2 | 5/1982 |
| EP | 0 300 865 | 1/1989 |
| EP | 0 431 580 | 6/1991 |
| EP | 0494623 A1 | 7/1992 |
| EP | 0 596 125 A1 | 5/1994 |
| EP | 773223 A1 | 5/1997 |
| FR | 2 706 895 | 12/1994 |
| JP | 07070135 A | 3/1995 |
| JP | 09291034 | 11/1997 |
| JP | 10287631 | 10/1998 |
| WO | 0464 846 A1 | 1/1992 |
| WO | WO 93/03025 | 2/1993 |
| WO | WO 93/13105 | 7/1993 |
| WO | WO 93/20099 | 10/1993 |
| WO | WO 94/01408 | 1/1994 |
| WO | WO 94/03426 | 2/1994 |
| WO | WO 94/10408 | 5/1994 |
| WO | WO 94 21628 | 9/1994 |
| WO | WO 94/24129 | 10/1994 |
| WO | WO 95/00508 | 1/1995 |
| WO | WO 95/04037 | 2/1995 |
| WO | WO 95/04039 | 2/1995 |

(List continued on next page.)

OTHER PUBLICATIONS

Wong et al., Polymorphisms in dopamine receptors: what to they tell us? European Journal of Pharmacology, vol. 410, pp. 183–203, 2000.*

Jerzy L. Mokrosz et al., 8–[4–[2–(1,2,3,4–Tetrahydroisoquinoliny)]butyl]–8azaspiro[4,5]decane–7,9–dione: A new 5–HT1a Receptor Ligand with the same activity profile as buspirone, Journal of Medicinal Chemistry., vol. 39, No. 5, 1996, pp. 1125–1129.

I. Boyfield et al. Bioorg. Med. Chem Lett. 1997, vol. 7 (15), 1995–1998.

I. Boyfield et al., Bioorg. Med. Chem. Lett., 1997, 7(3), 327–330.

Patsenko et al., Chemical Abstracts, vol. 107, No. 11, Sep. 14, 1987 (Abstract No. 089337).

K.Y. Avenell et al., Bioorg. Med. Chem. Lett., 1999, 9(18), 2715–2720.

K.Y. Avenell et al., Bioorg. Med. Chem. Lett., 1998, 8(20), 2859–2864.

N.E. Austin et al., Bioorg. Med. Chem. Lett., 1999, 9(2), 179–184.

D. Bolton et al., Bioorg. Med. Chem. Lett., 1997, 7(4), 485–488.

*Primary Examiner*—Brenda Coleman
(74) *Attorney, Agent, or Firm*—Nora Stein-Fernandez

(57) ABSTRACT

Compounds of Formula I

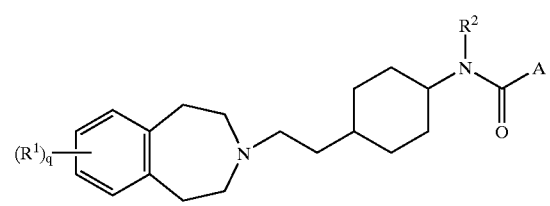

Formula I and their salts having affinity for dopamine receptors, in particular the $D_3$ Receptor, and thus potential in the treatment of conditions wherein modulation of the $D_3$ receptor is beneficial, e.g., as antipsychotic agents.

21 Claims, No Drawings

FOREIGN PATENT DOCUMENTS

| | | |
|---|---|---|
| WO | WO 95/05363 | 2/1995 |
| WO | WO 95/08533 | 3/1995 |
| WO | WO 95/10504 | 4/1995 |
| WO | WO 95/10513 | 4/1995 |
| WO | WO 95/16674 | 6/1995 |
| WO | WO 95/21165 | 8/1995 |
| WO | WO 95/21832 | 8/1995 |
| WO | WO 95/22542 | 8/1995 |
| WO | WO 95/29891 | 11/1995 |
| WO | WO 96/02246 | 2/1996 |
| WO | WO 96/02249 | 2/1996 |
| WO | WO 96/02519 | 2/1996 |
| WO | WO 96/02520 | 2/1996 |
| WO | WO 96/09286 | 3/1996 |
| WO | WO 96/10018 | 4/1996 |
| WO | WO 96/11007 | 4/1996 |
| WO | WO 96/16040 | 5/1996 |
| WO | WO 96/20179 | 7/1996 |
| WO | WO 96/20180 | 7/1996 |
| WO | WO 96/20190 | 7/1996 |
| WO | WO 96/25411 | 8/1996 |
| WO | WO 96/30333 | 10/1996 |
| WO | WO 97/00243 | 1/1997 |
| WO | WO 97/11070 | 3/1997 |
| WO | WO 98/51671 | 5/1997 |
| WO | WO 97/25324 | 7/1997 |
| WO | WO 97/28166 | 8/1997 |
| WO | WO 97/29079 | 8/1997 |
| WO | WO 97/31916 | 9/1997 |
| WO | WO 97/34889 | 9/1997 |
| WO | WO 97/38989 | 10/1997 |
| WO | WO97/40015 | 10/1997 |
| WO | WO 97/43262 | 11/1997 |
| WO | WO 97 43262 | 11/1997 |
| WO | WO 97/47602 | 12/1997 |
| WO | WO 98 06699 | 2/1998 |
| WO | WO 98/07421 | 2/1998 |
| WO | WO 98/23593 | 6/1998 |
| WO | WO 98/48784 | 11/1998 |
| WO | WO98/49145 | 11/1998 |
| WO | WO 98/50363 | 11/1998 |
| WO | WO 98 50364 | 11/1998 |
| WO | WO 98/52923 | 11/1998 |
| WO | WO99/59974 | 11/1999 |
| WO | WO 00/21951 | 4/2000 |
| WO | WO00/24717 | 5/2000 |
| WO | WO 00/42036 | 7/2000 |
| WO | WO 00/42037 | 7/2000 |
| WO | WO 00/42038 | 7/2000 |
| ZA | 8106903 A | 2/1993 |

* cited by examiner

TETRAHYDROBENZAZEPINE DERIVATIVES USEFUL AS MODULATORS OF DOPAMINE D₃ RECEPTORS (ANTIPSYCHOTIC AGENTS)

This application is a national stage entry under 35 U.S.C. §371 of PCT/EP99/07763, filed Oct. 6, 1999.

The present invention relates to novel tetrahydrobenzazepine derivatives, processes for their preparation, pharmaceutical compositions containing them and their use in therapy, as modulators of dopamine $D_3$ receptors, in particular as antipsychotic agents.

U.S. Pat. No. 5,294,621 describes tetrahydropyridine derivatives of the formula:

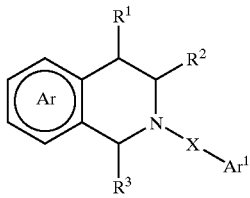

wherein

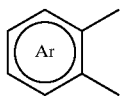

is an optionally substituted thienyl or optionally substituted phenyl ring; $R^1$, $R^2$ and $R^3$ are each inter alia hydrogen; X is inter alia $(CH_2)mNR^7CO$; m is 2–4; and $Ar^1$ is an optionally substituted heterocyclic ring or an optionally substituted phenyl ring. The compounds are said to be useful as antiarrhythmic agents.

EPA 431,580 describes compounds of formula

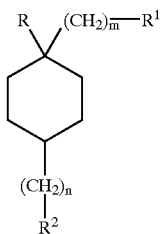

wherein R is $OR^3$, $NR^4R^5$, or $N(OR^4)R^5$, $R^4$ and $R^5$ are inter alia hydrogen, lower alkyl, aroyl or heteroaroyl; m is zero, 1 or 2; $R^1$ is hydrogen, aryl or various heteroaryl groups; n is zero or 1–4; and $R^2$ is:

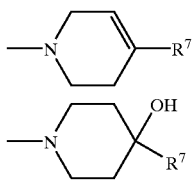

The compounds are said to be dopaminergic agents useful as antipsychotics, antihypertensives and also of use in the treatment of hyperprolactinaemia-related conditions and several central nervous system disorders.

WO 95/10513 describes benzothiophene derivatives and related compounds as estrogen agonists.

WO 97/43262 and WO 98/06699 describe tetrahydroisoquinoline derivatives as having affinity for the dopamine $D_3$ receptor.

We have now found a class of tetrahydrobenzazepine derivatives which have affinity for dopamine receptors, in particular the $D_3$ receptor, and thus potential in the treatment of conditions wherein modulation of the $D_3$ receptor is beneficial, eg as antipsychotic agents.

In a first aspect the present invention provides compounds of formula (I):

Formula (I)

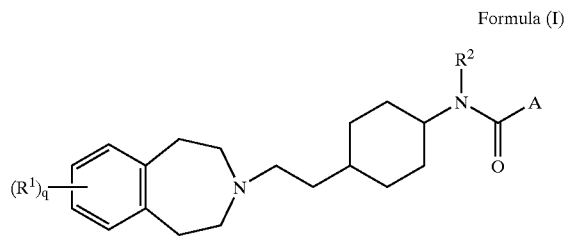

wherein:

$R^1$ represents a substituent selected from: a hydrogen or halogen atom; a hydroxy, cyano, nitro, trifluoromethyl, trifluoromethoxy, trifluoromethanesulfonyloxy, pentafluoroethyl, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl $C_{1-4}$alkylsulfonyl, $C_{1-4}$alkylsulfonyloxy, $C_{1-4}$alkylsulfonyl$C_{1-4}$alkyl, arylsulfonyl, arylsulfonyloxy, arylsulfonyl$C_{1-4}$alkyl, $C_{1-4}$alkylsulfonamido, $C_{1-4}$alkylamido, $C_{1-4}$alkylsulfonamido$C_{1-4}$alkyl, $C_{1-4}$alkylamido $C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacycloalkane or $C_{3-6}$(2-oxo)azacycloalkane ring and p represents zero or an integer from 1 to 4; or a group $Ar^3$—Z, wherein $Ar^3$ represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

q is 1 or 2;

A represents a group of the formula (a), (b) (c) or (d):

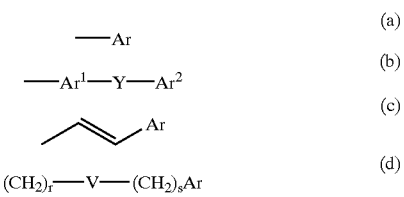

wherein

Ar represents an optionally substituted phenyl ring or an optionally substituted 5- or 6-membered aromatic heterocyclic ring; or an optionally substituted bicyclic ring system;

$Ar^1$ and $Ar^2$ each independently represent an optionally substituted phenyl ring or an optionally substituted 5- or 6-membered aromatic heterocyclic ring; and Y represents a bond, —NHCO—, —CONH—, —CH$_2$—, or —(CH$_2$)$_m$Y$^1$(CH$_2$)$_n$—, wherein Y$^1$ represents O, S, SO$_2$, or CO and m and n each represent zero or 1 such that the sum of m+n is zero or 1; providing that when A represents a group of formula (a), any substituent present in Ar ortho to the carboxamide moiety is necessarily a hydrogen or a methoxy group;

r and s independently represent an integer from zero to 3 such that the sum of r and s is equal to an integer from 1 to 4;

V represents a bond, O or S;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-butyl, and the like.

When R$^1$ represents an arylC$_{1-4}$alkoxy, arylsulfonyl, arylsulfonyloxy, arylsulfonylC$_{1-4}$alkyl, arylsulfonamido, arylcarboxamido, arylsulfonamidoC$_{1-4}$alkyl, arylcarboxamidoC$_{1-4}$alkyl, aroyl, aroylC$_{1-4}$alkyl, or aryl C$_{1-4}$alkanoyl group, the aryl moiety may be selected from an optionally substituted phenyl ring or an optionally substituted 5- or 6-membered heterocyclic ring. In the group R$^1$ an aryl moiety may be optionally substituted by one or more substituents selected from hydrogen, halogen, amino, cyano, C$_{1-4}$alkyl, C$_{1-4}$alkylamino, C$_{1-4}$dialkylamino, C$_{1-4}$alkylamido, C$_{1-4}$alkanoyl, or R$^5$R$^6$NCO where each of R$^5$ and R$^6$ independently represents a hydrogen atom or C$_{1-4}$alkyl group.

A halogen atom present in the compounds of formula (I) may be fluorine, chlorine, bromine or iodine.

When q is 2, the substituents R$^1$ may be the same or different.

An optionally substituted 5- or 6-membered heterocyclic aromatic ring, as defined for any of the groups Ar, Ar$^1$, Ar$^2$ or Ar$^3$ may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, pyrazolyl, isothiazolyl, and isoxazolyl.

Examples of bicyclic, for example bicyclic aromatic or heteroaromatic, ring systems for Ar include naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl, isoquinolinyl, pyrazolo[1,5-a]pyrimidyl, pyrrolo[3,2-b]pyridyl, pyrrolo[3,2-c]pyridyl, thieno[3,2-b]thiophenyl, 1,2-dihydro-2-oxo-quinolinyl, 3,4-dihydro-3-oxo-2H-benzoxazinyl, 1,2-dihydro-2-oxo-3H-indolyl.

The rings Ar, Ar$^1$, or Ar$^2$ may each independently be optionally substituted by one or more substituents selected from: a hydrogen or halogen atom, or a hydroxy, oxo, cyano, nitro, trifluoromethyl, C$_{1-4}$alkyl, C$_{1-4}$alkoxy, C$_{1-4}$alkylenedioxy, C$_{1-4}$alkanoyl, C$_{1-4}$alkylsulfonyl, C$_{1-4}$alkylsulfinyl, C$_{1-4}$alkylthio, R$^7$SO$_2$N(R$^8$)—, R$^7$R$^8$NSO$_2$—, R$^7$R$^8$N—, R$^7$R$^8$NCO—, or R$^7$CON(R$^8$)— group wherein each of R$^7$ and R$^8$ independently represents a hydrogen atom or a C$_{1-4}$ alkyl group, or R$^7$R$^8$ together form a C$_{3-6}$ alkylene chain.

Alternatively, Ar and Ar$^2$ may be optionally substituted by one or more 5- or 6-membered heterocyclic rings, as defined above, optionally substituted by a C$_{1-2}$ alkyl or R$^7$R$^8$N— group; wherein R$^7$ and R$^8$ are as defined above.

In the rings Ar and Ar$^2$ substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulfuric, nitric or phosphoric acid; and organic acids eg. succinic, maleic, acetic, fumaric, citric, tartaric, benzoic, p-toluenesulfonic, methanesulfonic or naphthalenesulfonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

The compounds of formula (I) can exist in the form of cis- and trans-isomers with respect to the configuration at the cyclohexyl ring. When A represents a group (c) the compounds may also exist as geometric isomers around the double bond. The present invention includes within its scope all such isomers, including mixtures. Preferably the compounds of the invention are in the trans configuration with respect to the cyclohexyl ring. For compounds of formula (I) where A represents a group (c), trans geometry of the double bond is preferred.

In compounds of formula (I), it is preferred that R$^1$ represents a substituent selected from: a halogen atom, methyl, cyano, acetyl, trifluoromethyl, pentafluoroethyl, methylsulphonyl, methylsulphonyloxy or trifluoromethoxy group. Alternatively, it is preferred that R$^1$ represents a group Ar$^3$Z, where Z is a bond and Ar$^3$ is a 5- or 6-membered ring heterocycle, optionally substituted by a methyl group, containing at least one N and one O atom. Preferably q is 1. R$^2$ is preferably a hydrogen atom.

When the group A is a group of formula (a), preferred examples of Ar include optionally substituted phenyl, indolyl, pyrazolo[1,5-a]pyrimidyl, cinnolinyl, quinolinyl, benzo[b]furanyl or pyrrolopyridyl.

When the group A is a group of formula (b), preferred examples of Ar$^1$ include optionally substituted phenyl, Y is preferably a bond, and preferred examples of Ar$^2$ include optionally substituted phenyl, pyridyl, pyrimidinyl, isoxazolyl, oxazolyl or oxadiazolyl.

When the group A is a group of formula (c), preferred examples of Ar include optionally substituted phenyl.

It is also preferred that the rings Ar, Ar$^1$, or Ar$^2$ are each independently optionally substituted by one or more substituents selected from: a hydrogen or halogen atom, cyano, methoxy, trifluoromethyl, methylenedioxy, acetyl, acetylamino, methylsulfonyl, methylsulfonyloxy, methylaminosulfonyl, methylsulfonylamino, or methylaminocarbonyl group.

Certain of the substituted heteroaromatic ring systems included in compounds of formula (I) may exist in one or more tautomeric forms. The present invention includes within its scope all such tautomeric forms, including mixtures.

Particular compounds according to the invention include those specifically exemplified and named hereinafter:

trans-3-(2-(1-(4-(4-Quinolinyl)carboxamido)cyclohexyl)ethyl)-2,3,4,5-tetrahydro-1H-3-benzazepine;

trans-(E)-3-(2-(1-(4-(3-(3-Methylsulfonyl)
phenylpropenoyl)amino)cyclohexyl)ethyl)-2,3,4,5-
tetrahydro-1H-3-benzazepine;

trans-(E)-3-(2-(1-(4-(3-(4-Fluoro)phenylpropenoyl)
amino)cyclohexyl)ethyl)-2,3,4,5-tetrahydro-1H-3-
benzazepine;

trans-3-(2-(1-(4-(2-Indolyl)carboxamido)cyclohexyl)
ethyl)-2,3,4,5-tetrahydro-1H-3-benzazepine;

trans-3-(2-(1-(4-(3-(3-Pyridyl)phenyl)carboxamido)
cyclohexyl)ethyl)-2,3,4,5-tetrahydro-1H-3-
benzazepine;

trans-3-(2-(1-(4-Phenylacetamido)cyclohexyl)ethyl)-2,3,
4,5-tetrahydro-1H-3-benzazepine;

trans-3-(2-(1-(4-(3-Indolyl)acetamido)cyclohexyl)ethyl)-
2,3,4,5-tetrahydro-1H-3-benzazepine;

trans-3-(2-(1-(4-(4-Quinolinyl)acetamido)cyclohexyl)
ethyl)-2,3,4,5-tetrahydro-1H-3-benzazepine;

trans-(E)-3-(2-(1-(4-(3-(4-Fluoro)phenylpropenoyl)
amino)cyclohexyl)ethyl)-6-methoxy-2,3,4,5-
tetrahydro-1H-3-benzazepine;

trans-6-Methoxy-3-(2-(1-(4-(4-quinolinyl)carboxamido)
cyclohexyl)ethyl)-2,3,4,5-tetrahydro-1H-3-
benzazepine;

trans-6-Methoxy-3-(2-(1-(4-(3-pyrrolo[2,3-b]pyridyl)
carboxamido)cyclohexyl)ethyl)-2,3,4,5-tetrahydro-
1H-3-benzazepine;

trans-(E)-7-Cyano-3-(2-(1-(4-(3-(4-fluoro)
phenylpropenoyl)amino)cyclohexyl)ethyl)-2,3,4,5-
tetrahydro-1H-3-benzazepine;

trans-7-Cyano-3-(2-(1-(4-(3-pyrrolo[2,3-b]pyridyl)
carboxamido)cyclohexyl)ethyl)-2,3,4,5-tetrahydro-
1H-3-benzazepine;

trans-7-Cyano-3-(2-(1-(4-(3-(5-methyl)-1,2,4-
oxadiazolyl)benzoyl)amino)-cyclohexyl)ethyl)-2,3,4,
5-tetrahydro-1H-3-benzazepine;

trans-(E)-7-Cyano-3-(2-(1-(4-(5-quinolinyl)
carboxamido)cyclohexyl)ethyl)-2,3,4,5-tetrahydro-
1H-benzazepine;

trans-(E)-7-Cyano-3-(2-(1-(4-(3-(3-acetylamino)
phenylpropenoyl)amino) cyclohexyl)ethyl)-2,3,4,5-
tetrahydro-1H-3-benzazepine;

trans-7-Cyano-3-(2-(1-(4-(6-(3,4-dihydro-3-oxo)-2H-
benzoxazinyl)carboxamido)-cyclohexyl)ethyl)-2,3,4,
5-tetrahydro-1H-benzazepine;

trans-(E)-7-Cyano-3-(2-(1-(4-(3-(6-(1,2-dihydro-2-oxo)
quinolinyl)propenoyl)amino)-cyclohexyl)ethyl)-2,3,4,
5-tetrahydro-1H-benzazepine;

trans-(E)-7-Cyano-3-(2-(1-(4-(3-(2-fluoro-4-
acetylamino)phenylpropenoyl)amino)-cyclohexyl)
ethyl)-2,3,4,5-tetrahydro-1H-benzazepine;

trans-(E)-7-Cyano-3-(2-(1-(4-(3-(8-(1,2-dihydro-2-oxo)
quinolinyl)propenoyl)amino)cyclohexyl)ethyl)-2,3,4,
5-tetrahydro-1H-benzazepine;

trans-7-Cyano-3-(2-(1-(4-(5-(8-fluoro)quinolinyl)
carboxamido)cyclohexyl)ethyl)-2,3,4,5-tetrahydro-
1H-3-benzazepine;

trans-7-Acetyl-3-(2-(1-(4-(5-quinolinyl)carboxamido)
cyclohexyl)ethyl)-2,3,4,5-tetrahydro-1H-3-
benzazepine;

trans-3-(2-(1-(4-(5-(2-Methyl)quinolinyl)carboxamido)
cyclohexyl)ethyl)-7-methylsulphonyl-2,3,4,5-
tetrahydro-1H-3-benzazepine;

trans-3-(2-(1-(4-(3-(5-Methyl)-1,2,4-oxadiazolyl)
benzoyl)amino)cyclohexyl)ethyl)-7-methylsulphonyl-
2,3,4,5-tetrahydro-1H-3-benzazepine;

trans-7-(5-(3-Methyl)-1,2,4-oxadiazolyl)-3-(2-(1-(4-(3-
pyrrolo[2,3-b]pyridyl)carboxamido)cyclohexyl)ethyl)-
2,3,4,5-tetrahydro-1H-3-benzazepine;

trans-(E)-7-(3-(5-Methyl)-1,2,4-oxadiazolyl)-3-(2-(1-(4-
(3-(4-fluoro)phenylpropenoyl)amino)cyclohexyl)
ethyl)-2,3,4,5-tetrahydro-1H-3-benzazepine;

trans-(E)-7-(5-(3-Methyl)-1,2,4-oxadiazolyl)-3-(2-(1-(4-
(3-(4-fluoro)phenylpropenoyl)amino)cyclohexyl)
ethyl)-2,3,4,5-tetrahydro-1H-3-benzazepine;

trans-(E)-7-(5-(3-Methyl)isoxazolyl)-3-(2-(1-(4-(3-(4-
fluoro)phenylpropenoyl)amino)cyclohexyl)ethyl)-2,3,
4,5-tetrahydro-1H-3-benzazepine;

trans-7-(5-(3-Methyl)-1,2,4-oxadiazolyl)-3-(2-(1-(4-(4-
fluoro)phenylacetamido)cyclohexyl)ethyl)-2,3,4,5-
tetrahydro-1H-3-benzazepine;

trans-7-Cyano-3-(2-(1-(4-(2,5-difluoro)
phenylacetamido)cyclohexyl)ethyl)-2,3,4,5-
tetrahydro-1H-3-benzazepine;

trans-7-Cyano-3-(2-(1-(2-naphthylacetamido)
cyclohexyl)ethyl)-2,3,4,5-tetrahydro-1H-3-
benzazepine;

trans-(E)-7-Cyano-3-(2-(1-(4-(3-(2,4-difluoro)
phenylpropenoyl)amino)cyclohexyl)ethyl)-2,3,4,5-
tetrahydro-1H-3-benzazepine;

trans-(E)-7-Cyano-3-(2-(1-(4-(3-(2,5-difluoro)
phenylpropenoyl)amino)cyclohexyl)ethyl)-2,3,4,5-
tetrahydro-1H-3-benzazepine;

trans-(E)-7-Cyano-3-(2-(1-(4-(3-(3-fluoro)
phenylpropenoyl)amino)cyclohexyl)ethyl)-2,3,4,5-
tetrahydro-1H-3-benzazepine;

trans-7-Cyano-3-(2-(1-(4-(3-phenylpropanoyl)amino)
cyclohexyl)ethyl)-2,3,4,5-tetrahydro-1H-3-
benzazepine;

trans-(E)-7-Cyano-3-(2-(1-(4-(3-(2-fluoro)
phenylpropenoyl)amino)cyclohexyl)ethyl)-2,3,4,5-
tetrahydro-1H-3-benzazepine;

trans-7-Cyano-3-(2-(1-(4-(8-(1,4-dihydro-4-oxo)
quinolinyl)carboxamido)cyclohexyl)ethyl)-2,3,4,5-
tetrahydro-1H-3-benzazepine;

trans-7-Cyano-3-(2-(1-(4-(2-naphthyl)carboxamido)
cyclohexyl)ethyl)-2,3,4,5-tetrahydro-1H-3-
benzazepine;

trans-(E)-7-Cyano-3-(2-(1-(4-(3-(2-methoxy)
phenylpropenoyl)amino)cyclohexyl)ethyl)-2,3,4,5-
tetrahydro-1H-3-benzazepine;

trans-(E)-7-Cyano-3-(2-(1-(4-(3-(3-methoxy)
phenylpropenoyl)amino)cyclohexyl)ethyl)-2,3,4,5-
tetrahydro-1H-3-benzazepine;

trans-(E)-7-Cyano-3-(2-(1-(4-(3-(4-methoxy)
phenylpropenoyl)amino)cyclohexyl)ethyl)-2,3,4,5-
tetrahydro-1H-3-benzazepine;

trans-(E)-7-Cyano-3-(2-(1-(4-(3-(2-acetyl)
phenylpropenoyl)amino)cyclohexyl)ethyl)-2,3,4,5-
tetrahydro-1H-3-benzazepine;

trans-(E)-7-Cyano-3-(2-(1-(4-(3-(4-acetyl)
phenylpropenoyl)amino)cyclohexyl)ethyl)-2,3,4,5-
tetrahydro-1H-3-benzazepine;

trans-(E)-7-Cyano-3-(2-(1-(4-(3-(2-cyano)
phenylpropenoyl)amino)cyclohexyl)ethyl)-2,3,4,5-
tetrahydro-1H-3-benzazepine;

trans-(E)-7-Cyano-3-(2-(1-(4-(3-(3-cyano)
phenylpropenoyl)amino)cyclohexyl)ethyl)-2,3,4,5-
tetrahydro-1H-3-benzazepine;

trans-7-Cyano-3-(2-(1-(4-(3-(5-(3-methyl)isoxazolyl)
benzoyl)amino)-cyclohexyl)ethyl)-2,3,4,5-tetrahydro-
1H-3-benzazepine;

trans-7-Cyano-3-(2-(1-(4-(7-(1,2-dihydro-2-oxo)
quinolinyl)carboxamido)cyclohexyl)ethyl)-2,3,4,5-
tetrahydro-1H-3-benzazepine;

trans-(Z)-7-Cyano-3-(2-(1-(4-(3-phenylpropenoyl)
amino)cyclohexyl)ethyl)-2,3,4,5-tetrahydro-1H-3-
benzazepine;

trans-(E)-7-Cyano-3-(2-(1-(4-(3-(2-pyridyl)propenoyl)
amino)cyclohexyl)ethyl)-2,3,4,5-tetrahydro-1H-3-
benzazepine;

trans-(E)-7-Cyano-3-(2-(1-(4-(3-(1-(4-fluoro)$_n$naphthyl)
propenoyl)amino)cyclohexyl)ethyl)-2,3,4,5-
tetrahydro-1H-3-benzazepine;

trans-(E)-7-Cyano-3-(2-(1-(4-(3-(6-benzodioxanyl)
propenoyl)amino)cyclohexyl)ethyl)-2,3,4,5-
tetrahydro-1H-3-benzazepine;

trans-(E)-7-Cyano-3-(2-(1-(4-(3-(3-(5-fluoro)indolyl)
propenoyl)amino)cyclohexyl)ethyl)-2,3,4,5-
tetrahydro-1H-3-benzazepine;

trans-(E)-7-Cyano-3-(2-(1-(4-(3-(3-(1-methyl)
benzimidazolyl)propenoyl)amino)cyclohexyl)ethyl)-2,
3,4,5-tetrahydro-1H-3-benzazepine;

trans-(E)-7-Cyano-3-(2-(1-(4-(3-(7-benzofuranyl)
propenoyl)amino)cyclohexyl)ethyl)-2,3,4,5-
tetrahydro-1H-3-benzazepine;

trans-(E)-7-Cyano-3-(2-(1-(4-(3-(5-(3-methyl)indolyl)
propenoyl)amino)cyclohexyl)ethyl)-2,3,4,5-
tetrahydro-1H-3-benzazepine;

trans-(E)-7-Cyano-3-(2-(1-(4-(3-(6-(2,3-dihydro-2-oxo)
indolyl)propenoyl)amino)cyclohexyl)ethyl)-2,3,4,5-
tetrahydro-1H-3-benzazepine;

trans-7-Cyano-3-(2-(1-(2-benzofuranylacetamido)
cyclohexyl)ethyl)-2,3,4,5-tetrahydro-1H-3-
benzazepine;

trans-(E)-7-Cyano-3-(2-(1-(4-(3-(4-(2-methyl)indolyl)
propenoyl)amino)cyclohexyl)ethyl)-2,3,4,5-
tetrahydro-1H-3-benzazepine;

trans-(E)-7-Cyano-3-(2-(1-(4-(3-(5-benzimidazolyl)
propenoyl)amino)cyclohexyl)ethyl)-2,3,4,5-
tetrahydro-1H-3-benzazepine;

trans-(E)-7-Cyano-3-(2-(1-(4-(3-phenylpropenoyl)
amino)cyclohexyl)ethyl)-2,3,4,5-tetrahydro-1H-3-
benzazepine;

trans-(E)-7-Cyano-3-(2-(1-(4-(3-(2,3-methylenedioxy)
phenylpropenoyl)amino)cyclohexyl)ethyl)-2,3,4,5-
tetrahydro-1H-3-benzazepine;

trans-(E)-7-Cyano-3-(2-(1-(4-(3-(3-(1-(2-oxo)
pyrrolidinyl))phenylpropenoyl)amino)cyclohexyl)
ethyl)-2,3,4,5-tetrahydro-1H-3-benzazepine;

trans-7-Cyano-3-(2-(1-(4-(2-indolylacetamido)
cyclohexyl)ethyl)-2,3,4,5-tetrahydro-1H-3-
benzazepine;

trans-7-Cyano-3-(2-(1-(4-(2-benzothiophenylacetamido)
cyclohexyl)ethyl)-2,3,4,5-tetrahydro-1H-3-
benzazepine;

trans-(E)-7-Cyano-3-(2-(1-(4-(3-(2-(3-bromo)
thiophenyl)propenoyl)amino)cyclohexyl)ethyl)-2,3,4,
5-tetrahydro-1H-3-benzazepine;

trans-7-Cyano-3-(2-(1-(4-(3-(2-pyridyl)benzoyl)amino)
cyclohexyl)ethyl)-2,3,4,5-tetrahydro-1H-3-
benzazepine;

trans-7-Cyano-3-(2-(1-(4-(3-(5-pyrimidinyl)benzoyl)
amino)cyclohexyl)ethyl)-2,3,4,5-tetrahydro-1H-3-
benzazepine;

trans-7-Cyano-3-(2-(1-(4-(3-(4-cyanophenyl)benzoyl)
amino)cyclohexyl)ethyl)-2,3,4,5-tetrahydro-1H-3-
benzazepine;

trans-7-Cyano-3-(2-(1-(4-(3-(3-(5-ethyl)-1,2,4-
oxadiazolyl)benzoyl)amino)-cyclohexyl)ethyl)-2,3,4,
5-tetrahydro-1H-3-benzazepine;

trans-(E)-7-Cyano-3-(2-(1-(4-(3-(2-thiophenyl)
propenoyl)amino)cyclohexyl)ethyl)-2,3,4,5-
tetrahydro-1H-3-benzazepine;

trans-(E)-7-Cyano-3-(2-(1-(4-(3-(2-furanyl)propenoyl)
amino)cyclohexyl)ethyl)-2,3,4,5-tetrahydro-1H-3-
benzazepine;

trans-(E)-7-Cyano-3-(2-(1-(4-(3-(3-thiophenyl)
propenoyl)amino)cyclohexyl)ethyl)-2,3,4,5-
tetrahydro-1H-3-benzazepine;

trans-(E)-7-Cyano-3-(2-(1-(4-(3-(3-furanyl)propenoyl)
amino)cyclohexyl)ethyl)-2,3,4,5-tetrahydro-1H-3-
benzazepine;

trans-(E)-7-Cyano-3-(2-(1-(4-(3-(4-quinolinyl)
propenoyl)amino)cyclohexyl)ethyl)-2,3,4,5-
tetrahydro-1H-3-benzazepine;

trans-(E)-7-Cyano-3-(2-(1-(4-(3-(5-pyrimidinyl)
propenoyl)amino)cyclohexyl)ethyl)-2,3,4,5-
tetrahydro-1H-3-benzazepine;

trans-7-Cyano-3-(2-(1-(4-(2,4-difluoro)
phenylacetamido)cyclohexyl)ethyl)-2,3,4,5-
tetrahydro-1H-3-benzazepine;

trans-7-Cyano-3-(2-(1-(4-(1-naphthyl)acetamido)
cyclohexyl)ethyl)-2,3,4,5-tetrahydro-1H-3-
benzazepine;

trans-7-Acetyl-3-(2-(1-(4-(3-pyrrolo[2,3-b]pyridyl)
carboxamido)cyclohexyl)ethyl)-2,3,4,5-tetrahydro-
1H-3-benzazepine;

trans-7-Acetyl-3-(2-(1-(4-(4-fluoro)phenylacetamido)
cyclohexyl)ethyl)-2,3,4,5-tetrahydro-1H-3-
benzazepine;

trans-7-Acetyl-3-(2-(1-(4-(3-(3-(5-methyl)-1,2,4-
oxadiazolyl)benzoyl)amino)-cyclohexyl)ethyl)-2,3,4,
5-tetrahydro-1H-3-benzazepine;

trans-(E)-7-Acetyl-3-(2-(1-(4-(3-(4-fluoro)
phenylpropenoyl)amino)cyclohexyl)ethyl)-2,3,4,5-
tetrahydro-1H-3-benzazepine;

trans-7-Cyano-3-(2-(1-(4-(6-(2-amino)benzothiazolyl)
acetamido)cyclohexyl)ethyl)-2,3,4,5-tetrahydro-1H-3-
benzazepine;

trans-7-Cyano-3-(2-(1-(4-(6-(2-methyl)benzothiazolyl)
acetamido)cyclohexyl)ethyl)-2,3,4,5-tetrahydro-1H-3-
benzazepine;

trans-7-Cyano-3-(2-(1-(4-(6-(2,3-dihydro-2-oxo)indolyl)
acetamido)cyclohexyl)ethyl)-2,3,4,5-tetrahydro-1H-3-
benzazepine;

trans-7-Cyano-3-(2-(1-(4-(5-(2,3-dihydro-2-oxo)indolyl)
acetamido)cyclohexyl)ethyl)-2,3,4,5-tetrahydro-1H-3-
benzazepine;

trans-(E)-7-Cyano-3-(2-(1-(4-(3-(4-
methylaminocarbonyl)phenylpropenoyl)amino)
cyclohexyl)ethyl)-2,3,4,5-tetrahydro-1H-3-
benzazepine;

trans-7-Cyano-3-(2-(1-(4-(5-(2-amino)benzoxazolyl)
acetamido)cyclohexyl)ethyl)-2,3,4,5-tetrahydro-1H-3-
benzazepine;

trans-7-Cyano-3-(2-(1-(4-(6-(1,2-dihydro-2-oxo)quinolinyl)acetamido)cyclohexyl)ethyl)-2,3,4,5-tetrahydro-1H-3-benzazepine;

trans-7-Cyano-3-(2-(1-(4-(7-(1,2-dihydro-2-oxo)quinolinyl)acetamido)cyclohexyl)ethyl)-2,3,4,5-tetrahydro-1H-3-benzazepine;

trans-(E)-7-Acetyl-3-(2-(1-(4-(3-(3-methoxy)phenylpropenoyl)amino)cyclohexyl)ethyl)-2,3,4,5-tetrahydro-1H-3-benzazepine;

trans-(E)-7-Acetyl-3-(2-(1-(4-(3-(2-cyano)phenylpropenoyl)amino)cyclohexyl)ethyl)-2,3,4,5-tetrahydro-1H-3-benzazepine;

trans-(E)-7-Acetyl-3-(2-(1-(4-(3-(3-thiophenyl)propenoyl)amino)cyclohexyl)ethyl)-2,3,4,5-tetrahydro-1H-3-benzazepine;

trans-(E)-7-Acetyl-3-(2-(1-(4-(3-(8-(1,2-dihydro-2-oxo)quinolinyl)propenoyl)amino)cyclohexyl)ethyl)-2,3,4,5-tetrahydro-1H-3-benzazepine;

trans-7-Cyano-3-(2-(1-(4-(3-(1-pyrazolyl)benzoyl)amino)cyclohexyl)ethyl)-2,3,4,5-tetrahydro-1H-3-benzazepine;

trans-7-Cyano-3-(2-(1-(4-(2-thiophenyl)acetamido)cyclohexyl)ethyl)-2,3,4,5-tetrahydro-1H-3-benzazepine;

trans-7-Cyano-3-(2-(1-(4-(3-benzothiophenyl)acetamido)cyclohexyl)ethyl)-2,3,4,5-tetrahydro-1H-3-benzazepine;

trans-7-Cyano-3-(2-(1-(4-(3-(2-(5-methyl)-1,3,4-oxadiazolyl)benzoyl)amino)-cyclohexyl)ethyl)-2,3,4,5-tetrahydro-1H-3-benzazepine;

trans-(E)-7-Cyano-3-(2-(1-(4-(3-(2-naphthyl)propenoyl)amino)cyclohexyl)ethyl)-2,3,4,5-tetrahydro-1H-3-benzazepine;

trans-7-Acetyl-3-(2-(1-(4-(3-benzothiophenyl)acetamido)cyclohexyl)ethyl)-2,3,4,5-tetrahydro-1H-3-benzazepine;

trans-(E)-7-Acetyl-3-(2-(1-(4-(3-(4-acetamido)phenylpropenoyl)amino)cyclohexyl)ethyl)-2,3,4,5-tetrahydro-1H-3-benzazepine;

trans-7-Acetyl-3-(2-(1-(4-(6-(2-amino)benzothiazolyl)acetamido)cyclohexyl)ethyl)-2,3,4,5-tetrahydro-1H-3-benzazepine;

trans-7-Acetyl-3-(2-(1-(4-(8-(1,4-dihydro-4-oxo)quinolinyl)carboxamido)cyclohexyl)ethyl)-2,3,4,5-tetrahydro-1H-3-benzazepine;

trans-(E)-7-Acetyl-3-(2-(1-(4-(3-(2-acetyl)phenylpropenoyl)amino)cyclohexyl)ethyl)-2,3,4,5-tetrahydro-1H-3-benzazepine;

trans-7-Acetyl-3-(2-(1-(4-(2-benzothiophenyl)acetamido)cyclohexyl)ethyl)-2,3,4,5-tetrahydro-1H-3-benzazepine;

trans-(E)-7-Cyano-3-(2-(1-(4-(3-(5-(3-acetyl)indolyl)propenoyl)amino)cyclohexyl)ethyl)-2,3,4,5-tetrahydro-1H-3-benzazepine;

trans-7-Cyano-3-(2-(1-(4-(3-(5-(3-methyl)-1,2,4-oxadiazolyl)benzoyl)amino)-cyclohexyl)ethyl)-2,3,4,5-tetrahydro-1H-3-benzazepine;

trans-7-Cyano-3-(2-(1-(4-(5-(2-methyl)benzimidazolyl)acetamido)cyclohexyl)ethyl)-2,3,4,5-tetrahydro-1H-3-benzazepine;

trans-7-Cyano-3-(2-(1-(4-(6-quinoxalinyl)acetamido)cyclohexyl)ethyl)-2,3,4,5-tetrahydro-1H-3-benzazepine;

trans-(E)-7-Cyano-3-(2-(1-(4-(3-(3-(2-acetyl)furanyl)propenoyl)amino)cyclohexyl)ethyl)-2,3,4,5-tetrahydro-1H-3-benzazepine;

trans-7-Cyano-3-(2-(1-(4-(6-(2-amino)benzoxazolyl)acetamido)cyclohexyl)ethyl)-2,3,4,5-tetrahydro-1H-3-benzazepine;

trans-7-Cyano-3-(2-(1-(4-(6-(3,4-dihydro-2-oxo)-2H-benzoxazinyl)acetamido)cyclohexyl)ethyl)-2,3,4,5-tetrahydro-1H-3-benzazepine;

trans-(E)-7-Cyano-3-(2-(1-(4-(3-(2-fluoro-5-acetamido)phenylpropenoyl)amino)cyclohexyl)ethyl)-2,3,4,5-tetrahydro-1H-3-benzazepine;

trans-7-(5-(3-Methyl)-1,2,4-oxadiazolyl)-3-(2-(1-(4-(2-benzothiophenyl)acetamido)cyclohexyl)ethyl)-2,3,4,5-tetrahydro-1H-3-benzazepine;

trans-(E)-7-(5-(3-Methyl)-1,2,4-oxadiazolyl)-3-(2-(1-(4-(3-(3-thienyl)propenoyl)amino)cyclohexyl)ethyl)-2,3,4,5-tetrahydro-1H-3-benzazepine;

trans-7-(5-(3-Methyl)-1,2,4-oxadiazolyl)-3-(2-(1-(4-(5-quinolinyl)carboxamido)cyclohexyl)ethyl)-2,3,4,5-tetrahydro-1H-3-benzazepine;

trans-7-(5-(3-Methyl)-1,2,4-oxadiazolyl)-3-(2-(1-(4-(3-(3-(5-Methyl)-1,2,4-oxadiazolyl)benzoyl)amino)cyclohexyl)ethyl)-2,3,4,5-tetrahydro-1H-3-benzazepine;

trans-7-(5-(3-Methyl)-1,2,4-oxadiazolyl)-3-(2-(1-(4-(8-(1,4-dihydro-4-oxo)quinolinyl)carboxamido)cyclohexyl)ethyl)-2,3,4,5-tetrahydro-1H-3-benzazepine;

trans-(E)-7-(5-(3-Methyl)-1,2,4-oxadiazolyl)-3-(2-(1-(4-(3-(3-fluoro)phenylpropenoyl)amino)cyclohexyl)ethyl)-2,3,4,5-tetrahydro-1H-3-benzazepine;

trans-(E)-7-(5-(3-Methyl)-1,2,4-oxadiazolyl)-3-(2-(1-(4-(3-(3-acetamido-2-fluoro)phenylpropenoyl)amino)cyclohexyl)ethyl)-2,3,4,5-tetrahydro-1H-3-benzazepine;

trans-(E)-7-(5-(3-Methyl)-1,2,4-oxadiazolyl)-3-(2-(1-(4-(3-(3-acetyl)phenylpropenoyl)amino)cyclohexyl)ethyl)-2,3,4,5-tetrahydro-1H-3-benzazepine;

trans-7-(5-(3-Methyl)-1,2,4-oxadiazolyl)-3-(2-(1-(4-(3-fluoro)phenylacetamido)cyclohexyl)ethyl)-2,3,4,5-tetrahydro-1H-3-benzazepine;

trans-7-(5-(3-Methyl)-1,2,4-oxadiazolyl)-3-(2-(1-(4-(2,4-difluoro)phenylacetamido)cyclohexyl)ethyl)-2,3,4,5-tetrahydro-1H-3-benzazepine;

trans-7-(5-(3-Methyl)-1,2,4-oxadiazolyl)-3-(2-(1-(4-(2-naphthyl)acetamido)cyclohexyl)ethyl)-2,3,4,5-tetrahydro-1H-3-benzazepine;

trans-7-(5-(3-Methyl)-1,2,4-oxadiazolyl)-3-(2-(1-(4-(7-(3,4-dihydro-3-oxo)-2H-benzoxazinyl)carboxamido)cyclohexyl)ethyl)-2,3,4,5-tetrahydro-1H-3-benzazepine;

trans-7-(5-(3-Methyl)-1,2,4-oxadiazolyl)-3-(2-(1-(4-(5-(2-methyl)quinolinyl)carboxamido)cyclohexyl)ethyl)-2,3,4,5-tetrahydro-1H-3-benzazepine;

trans-7-(5-(3-Methyl)-1,2,4-oxadiazolyl)-3-(2-(1-(4-(2-fluoro)phenylacetamido)cyclohexyl)ethyl)-2,3,4,5-tetrahydro-1H-3-benzazepine;

trans-3-(2-(1-(4-(5-(2-Methyl)quinolinyl)carboxamide)cyclohexyl)ethyl)-7-methanesulphonyloxy-2,3,4,5-tetrahydro-1H-3-benzazepine;

trans-7-(5-(3-Methyl)-1,2,4-oxadiazolyl)-3-(2-(1-(4-(2-indolyl)carboxamido)cyclohexyl)ethyl)-2,3,4,5-tetrahydro-1H-3-benzazepine;

trans-7-(3-(5-Methyl)-1,2,4-oxadiazolyl)-3-(2-(1-(4-(2-benzothiophenyl)acetamido)cyclohexyl)ethyl)-2,3,4,5-tetrahydro-1H-3-benzazepine;

trans-(E)-7-(3-(5-Methyl)-1,2,4-oxadiazolyl)-3-(2-(1-(4-(3-(3-thienyl)propenoyl)amino)cyclohexyl)ethyl)-2,3,4,5-tetrahydro-1H-3-benzazepine;

trans-7-(3-(5-Methyl)-1,2,4-oxadiazolyl)-3-(2-(1-(4-(5-quinolinyl)carboxamido)cyclohexyl)ethyl)-2,3,4,5-tetrahydro-1H-3-benzazepine;

trans-7-(3-(5-Methyl)-1,2,4-oxadiazolyl)-3-(2-(1-(4-(3-pyrrolo[2,3-b]pyridyl)carboxamido)cyclohexyl)ethyl)-2,3,4,5-tetrahydro-1H-3-benzazepine;

trans-7-(3-(5-Methyl)-1,2,4-oxadiazolyl)-3-(2-(1-(4-(8-(1,4-dihydro-4-oxo)quinolinyl)carboxamido)cyclohexyl)ethyl)-2,3,4,5-tetrahydro-1H-3-benzazepine;

trans-7-(3-(5-Methyl)-1,2,4-oxadiazolyl)-3-(2-(1-(4-(3-(3-(5-Methyl)-1,2,4-oxadiazolyl)benzoyl)amino)cyclohexyl)ethyl)-2,3,4,5-tetrahydro-1H-3-benzazepine;

trans-(E)-7-(3-(5-Methyl)-1,2,4-oxadiazolyl)-3-(2-(1-(4-(3-(3-fluoro)phenylpropenoyl)amino)cyclohexyl)ethyl)-2,3,4,5-tetrahydro-1H-3-benzazepine;

trans-(E)-7-(3-(5-Methyl)-1,2,4-oxadiazolyl)-3-(2-(1-(4-(3-(2-fluoro)phenylpropenoyl)amino)cyclohexyl)ethyl)-2,3,4,5-tetrahydro-1H-3-benzazepine;

trans-3-(2-(1-(4-(5-(2-Methyl)quinolinyl)carboxamide)cyclohexyl)ethyl)-7-methanesulphonyloxy-2,3,4,5-tetrahydro-1H-3-benzazepine;

trans-(E)-3-(2-(1-(4-(3-(4-fluoro)phenylpropenoyl)amino)cyclohexyl)ethyl)-7-methylsulphonyl-2,3,4,5-tetrahydro-1H-3-benzazepine;

trans-3-(2-(1-(4-(3-(2-(4-Methyl)oxazolyl)benzoyl)amino)cyclohexyl)ethyl)-7-methylsulphonyl-2,3,4,5-tetrahydro-1H-3-benzazepine;

trans-3-(2-(1-(4-(3-trifluoromethylbenzoyl)amino)cyclohexyl)ethyl)-7-methylsulphonyl-2,3,4,5-tetrahydro-1H-3-benzazepine;

trans-3-(2-(1-(4-(5-(8-Chloro-2-methyl)quinolinyl)carboxamide)cyclohexyl)ethyl)-7-methanesulphonyl-2,3,4,5-tetrahydro-1H-3-benzazepine;

trans-7-(5-(3-Methyl)isoxazolyl)-3-(2-(1-(4-(2-fluoro)phenylacetamido)cyclohexyl)ethyl)-2,3,4,5-tetrahydro-1H-3-benzazepine;

trans-7-(3-(5-Methyl)isoxazolyl)-3-(2-(1-(4-(4-fluoro)phenylacetamido)cyclohexyl)ethyl)-2,3,4,5-tetrahydro-1H-3-benzazepine;

trans-(E)-7-(2-(5-Methyl)oxazolyl)-3-(2-(1-(4-(3-(4-fluoro)phenylpropenoyl)amino)cyclohexyl)ethyl)-2,3,4,5-tetrahydro-1H-3-benzazepine;

trans-(E)-7-(3-(5-Methyl)isoxazolyl)-3-(2-(1-(4-(3-(4-fluoro)phenylpropenoyl)amino)cyclohexyl)ethyl)-2,3,4,5-tetrahydro-1H-3-benzazepine;

trans-(E)-7-(2-Pyridyl)-3-(2-(1-(4-(3-(4-fluoro)phenylpropenoyl)amino)cyclohexyl)ethyl)-2,3,4,5-tetrahydro-1H-3-benzazepine;

trans-(E)-7-(2-Pyrimidyl)-3-(2-(1-(4-(3-(4-fluoro)phenylpropenoyl)amino)cyclohexyl)ethyl)-2,3,4,5-tetrahydro-1H-3-benzazepine;

trans-(E)-7-(1-Pyrrolidinylcarbonyl)-3-(2-(1-(4-(3-(4-fluoro)phenylpropenoyl)amino)cyclohexyl)ethyl)-2,3,4,5-tetrahydro-1H-3-benzazepine;

trans-7-(1-Pyrrolidinylcarbonyl)-3-(2-(1-(4-(3-pyrrolo[2,3-b]pyridyl)carboxamido)cyclohexyl)ethyl)-2,3,4,5-tetrahydro-1H-3-benzazepine;

trans-(E)-7-(5-Pyrimidyl)-3-(2-(1-(4-(3-(4-fluoro)phenylpropenoyl)amino)cyclohexyl)ethyl)-2,3,4,5-tetrahydro-1H-3-benzazepine;

trans-7-(5-Pyrimidinyl)-3-(2-(1-(4-(3-(3-(5-Methyl)-1,2,4-oxadiazolyl)benzoyl)amino)cyclohexyl)ethyl)-2,3,4,5-tetrahydro-1H-3-benzazepine;

trans-7-(5-Pyrimidinyl)-3-(2-(1-(4-(5-(2-methyl)quinolinyl)carboxamido)cyclohexyl)ethyl)-2,3,4,5-tetrahydro-1H-3-benzazepine;

trans-7-(3-(5-Methyl)isoxazolyl)-3-(2-(1-(4-(5-(2-methyl)quinolinyl)carboxamido)cyclohexyl)ethyl)-2,3,4,5-tetrahydro-1H-3-benzazepine;

trans-(E)-7-(2-Pyridyl)-3-(2-(1-(4-(3-(2-cyano)phenylpropenoyl)amino)cyclohexyl)ethyl)-2,3,4,5-tetrahydro-1H-3-benzazepine;

trans-(E)-7-(2-Pyridyl)-3-(2-(1-(4-(3-(3-cyano)phenylpropenoyl)amino)cyclohexyl)ethyl)-2,3,4,5-tetrahydro-1H-3-benzazepine;

trans-(E)-7-(2-Pyridyl)-3-(2-(1-(4-(3-(4-cyano)phenylpropenoyl)amino)cyclohexyl)ethyl)-2,3,4,5-tetrahydro-1H-3-benzazepine;

trans-3-(2-(1-(4-(5-(8-Fluoro-2-methyl)quinolinyl)carboxamido)cyclohexyl)ethyl)-7-methylsulphonyl-2,3,4,5-tetrahydro-1H-3-benzazepine;

trans-3-(2-(1-(4-(5-(8-Fluoro-2-methyl)quinolinyl)carboxamido)cyclohexyl)ethyl)-7-methylsulphonyloxy-2,3,4,5-tetrahydro-1H-3-benzazepine;

trans-3-(2-(1-(4-(3-(2-(5-Methyl)oxazolyl)benzoyl)amino)cyclohexyl)ethyl)-7-methylsulphonyloxy-2,3,4,5-tetrahydro-1H-3-benzazepine;

These compounds may be in the form of their free base or physiologically acceptable salts thereof, particularly the monohydrochloride or monomesylate salts.

The present invention also provides a process for preparing compounds of formula (I) which process comprises:

(a) reacting a compound of formula (II):

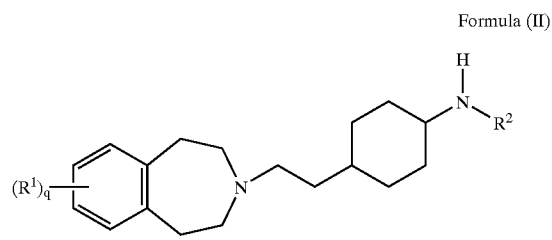

Formula (II)

wherein $R^1$, $R^2$ and q are as hereinbefore defined, with a compound of formula (III):

A—COX                         Formula (III)

wherein A is as hereinbefore defined and X is a halogen atom or the residue of an activated ester;

(b) to prepare a compound of formula (I) by reacting a compound of formula (II) with a compound A—Br, or A—I, or A—OSO$_2$CF$_3$ in the presence of carbon monoxide and a catalyst such as trans-bis-triphenylphosphinepalladium(II)bromide;

(c) to prepare a compound of formula (I) wherein $R^1$ is $Ar^3$—Z and Z is a bond, reacting a compound of formula (IV):

Formula (IV)

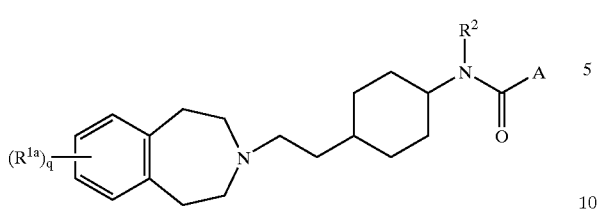

wherein $R^2$ and A are as hereinbefore defined and one $R^{1a}$ represents a group W wherein W is a halogen atom or a trifluoromethylsulfonyloxy group, or W is a group M selected from a boron derivative e.g. a boronic acid function $B(OH)_2$ or a metal function such as trialkylstannyl e.g. $SnBu_3$, zinc halide or magnesium halide, and when q is 2 the other $R^{1a}$ is $R^1$; with a compound $Ar^3$—$W^1$, wherein $W^1$ is a halogen atom or a trifluoromethylsulfonyloxy group when W is a group M or $W^1$ is a group M when W is a halogen atom or a trifluoromethylsulfonyloxy group;

(d) to prepare a compound of formula (I) wherein $R^1$ is $Ar^3$—Z and Z is O or S, reacting a compound of formula (V):

Formula (V)

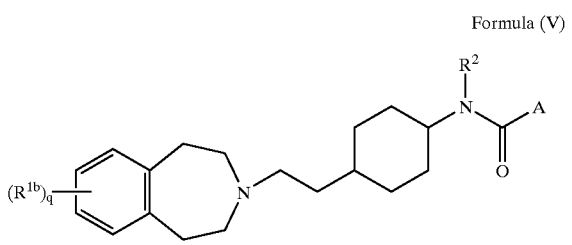

wherein $R^2$ and A are as hereinbefore defined and one $R^{1b}$ represents a group ZH and when q is 2 the other $R^{1b}$ represents $R^1$; with a reagent serving to introduce the group $Ar^3$;

(e) to prepare a compound of formula (I) where Y is a bond, reaction of a compound of formula (VI):

Formula (VI)

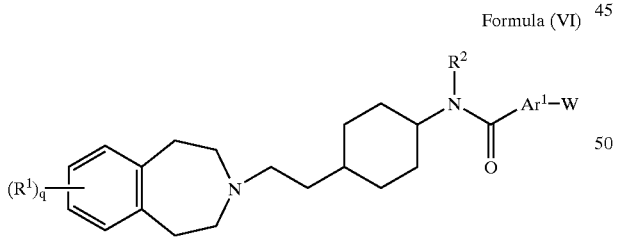

wherein $R^1$, $R^2$, $Ar^1$, W and q are as hereinbefore defined, with a compound $Ar^2$—$W^1$, wherein $W^1$ is a halogen atom or a trifluoromethylsulfonyloxy group when W is a group M, or $W^1$ is a group M when W is a halogen atom or a trifluoromethylsulfonyloxy group.

(f) interconversion of one compound of formula (I) to a different compound of formula (I) e.g. (i) alkylation of a compound (I) wherein $R^2$ represents hydrogen, (ii) conversion of one $R^1$ from alkoxy (e.g.methoxy) to hydroxy, or (iii) conversion of $R^1$ from hydroxy to sulfonyloxy, eg alkylsulfonyloxy or trifluoromethanesulfonyloxy; (iv) conversion of a compound wherein Y represents S to a compound wherein Y is $SO_2$ or (v) conversion of Y from CO to $CH_2$;

(g) separation of cis- and trans-isomers of compounds of formula (I) by conventional methods, e.g. chromatography or crystallisation; and optionally thereafter forming a salt of formula (I).

Process (a) may be effected using conventional methods for the formation of an amide bond. When X is the residue of an activated ester this may be formed with e.g. a carbodiimide such as 1-ethyl-3-(3-dimethylaminopropyl) carbodiimide. The reaction may be carried out in a solvent such as dichloromethane.

Reaction of a compound of formula (IV) with $Ar^3W^1$, according to process (c) or a compound of formula (VI) with $Ar^2$—$W^1$ according to process (e) may be effected in the presence of a transition metal eg palladium catalyst such as bis-triphenylphosphinepalladium dichloride or tetrakis-triphenylphosphinepalladium (0). When M represents a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulfonyloxy group such as trifluoromethylsulfonyloxy; and $W^1$ is preferably a group M, such as trialkylstannyl or $B(OH)_2$.

In process (d) the reagent serving to introduce the group $Ar^3$ is preferably a compound of formula $Ar^3$—Hal, wherein Hal is a halogen atom. The reaction may be effected in the presence of a base, such as potassium carbonate, in a solvent such as dimethylformamide.

Interconversion reactions according to process (f) may be effected using methods well known in the art.

Compounds of formula (II) may be prepared by conversion of a compound of formula (VII), wherein $R^1$ and q are as hereinbefore defined, Formula (VII)

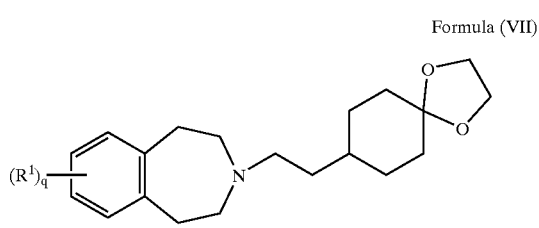

into a corresponding ketone, followed by reductive amination. This may be effected by methods well known in the art for (i) conversion of a ketal to a ketone in the presence of aqueous acid; followed by (ii) reductive amination of the ketone with $R^2NH_2$ or ammonium acetate in the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as methanol, ethanol or dichloroethane.

A compound of formula (VII) may itself be prepared by reacting a compound of formula (VIII):

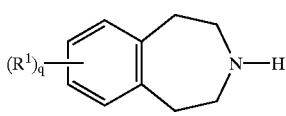

Formula (VIII)

wherein $R^1$ and q are as hereinbefore defined;
with a compound of formula (IX):

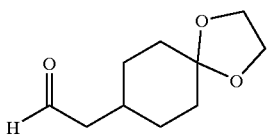

Formula (IX)

in the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol or dichloroethane.

The individual cis- and trans-isomers of a compound of formula (II) may be prepared starting from cis- or trans-4-amino-cyclohexaneacetic acid (T. P. Johnson, et al., J. Med. Chem., 1997, (20), 279–290) followed by functional group interchange and/or protection using methods well known in the art, to give the individual cis- or trans-isomers of a compound of formula (X):

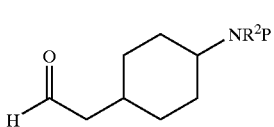

Formula (X)

wherein $R^2$ is as hereinbefore defined, and P is a protecting group, for example trifluoroacetyl or tert-butoxycarbonyl. Subsequent reaction of a compound of formula (X) with a compound of formula (VIII) in the presence of a reducing agent as described above followed by deprotection using standard methodology gives the individual isomers of a compound of formula (II) wherein $R^2$ is as hereinbefore defined.

Compounds of formula (III) are known or may be prepared using standard procedures.

Compounds of formula (IV), (V) or (VI) may be prepared by processes analogous to (a), (b), (c) and (d) described above. Compounds $Ar^2W^1$, $Ar^3W^1$ and $Ar^3Hal$ are commercially available or may be prepared by standard methods. Compounds of formula (VIII), where for example $R^1$ is a halogen, methoxy, acetyl, cyano, carboxylic acid or carboxamide group are known in the literature or may be prepared by known methods. The compound of formula (IX) is likewise known in the literature.

Conversion of a compound of formula (VIII) where $R^1$ is a cyano or acetyl group to a compound of formula (VIII) where $R^1$ is a group $Ar^3Z$, where Ar is an oxadiazole or an isoxazole ring and Z is a bond, may be carried out by (i) conversion to a compound of formula (XI), where $R^1$ and q are as hereinbefore defined, using standard methods; (ii) conversion of $R^1$ from cyano to oxadiazolyl using known methods, or conversion of acetyl to isoxazolyl using known methods; (iii) deprotection of a compound of formula (XI) to a compound of formula (VIII) using standard methods.

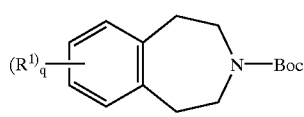

Formula (XI)

Compounds of formula (I) have been found to exhibit affinity for dopamine receptors, in particular the $D_3$ receptor, and are expected to be useful in the treatment of disease states which require modulation of such receptors, such as psychotic conditions. Compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloffet al, Nature, 1990; 347: 146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (eg see Schwartz et al., Brain Res. Reviews, 1998, 26, 236–242). From the localisation of D3 receptors, it could also be envisaged that the compounds could also have utility for the treatment of substance abuse where it has been suggested that D3 receptors are involved (eg see Levant, 1997, Pharmacol. Rev., 49, 231–252). Examples of such substance abuse include alcohol, cocaine and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

A preferred use for $D_3$ antagonists according to the present invention is in the treatment of psychoses such as schizophrenia.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of [$^{125}$I] iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4 @ 37° C.), 120 mM NaCl, 5 mM KCl, 2 mM $CaCl_2$, 1 mM $MgCl_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM $CaCl_2$, 1 mM $MgCl_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used. Competition curves were analysed simultaneously whenever possible using non-linear least-squares fitting procedures, capable of fitting one, two or three site models. Compounds of Examples tested according to this method had pKi values in the range 7.0–9.0 at the human cloned dopamine $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM et al Science 1992 257 1906–1912) In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90 s. The pump was on for the first 60s and the acidification rate determined between 68 and 88 s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. & Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Compounds of Examples tested according to this method were shown to be antagonists with pKb values in the range 7.0–10.0 at the human cloned dopamine $D_3$ receptor.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler * | 50–250 mg |
| Binder | 5–25 mg |
| Disintegrant * | 5–50 mg |
| Lubricant | 1–5 mg |
| Cyclodextrin | 1–100 mg |

* may also include cyclodextrins
Diluent:     e.g. Microcrystalline cellulose, lactose, starch
Binder:      e.g. Polyvinylpyrrolidone, hydroxypropymethylcellulose
Disintegrant: e.g. Sodium starch glycollate, crospovidone
Lubricant:   e.g. Magnesium stearate, sodium stearyl fumarate.

| Oral Suspension | |
|---|---|
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Diluent:      e.g. sorbitol solution, typically water
Preservative: e.g. sodium benzoate
Buffer:       e.g. citrate
Co-solvent:   e.g. alcohol, propylene glycol, polyethylene glycol, cyclodextrin The invention is further illustrated by the following non-limiting examples:

DESCRIPTION 1

2,3,4,5-Tetrahydro-1H-3-benzazepine 1,2-Phenylenediacetonitrile (7.5 g, 48 mmol) dissolved in ethanol (150 ml) was added to Raney Ni (2 g) which had been previously washed with ethanol (3×20 ml). The mixture was then hydrogenated at 50° C. at 50 psi pressure with shaking for 24 h. The reaction mixture was then cooled to room temperature and filtered through a pad of kieselguhr and washed through with ethanol (100 ml). The filtrate was evaporated in vacuo to give a brown oil which was chromatographed on silica gel (100 g), eluting with 2–10% methanol in $CH_2Cl_2$ to give the title compound as a brown oil (2.45 g, 35%).

Mass spectrum (API$^+$) Found: 148 (MH$^+$). C$_{10}$H$_{13}$N requires 147.

DESCRIPTION 2 trans-3-(2-(1-(4-(N-tert-Butoxycarbonyl)amino) cyclohexyl)ethyl)-2,3,4,5-tetrahydro-1H-3-benzazepine Sodium triacetoxyborohydride (4.3 g, 20.4 mmol) was added to a mixture of 2,3,4,5-tetrahydro-1H-3-benzazepine (2.0 g, 13.6 mmol), and trans-2-(1-(4-(N-tert-butoxycarbonyl)amino)cyclohexyl)acetaldehyde in 1,2-dichloroethane (200 ml), and the mixture stirred at room temperature for 0.5 h. The reaction mixture was diluted with CH$_2$Cl$_2$ (100 ml) and washed with saturated aqueous K$_2$CO$_3$ (200 ml), followed by brine (100 ml). The organic layer was separated and dried over Na$_2$SO$_4$, then evaporated in vacuo to give an off-white solid which was chromatographed on silica gel eluting with ethyl acetate to give the title compound as an off-white solid (3.13 g, 62%).

Mass spectrum (API$^+$): Found 373. C$_{23}$H$_{36}$N$_2$O$_2$ requires 372.

The following compound was prepared in a similar manner to Description 2

(a) trans-3-(2-(1-(4-N-tert-Butoxycarbonyl)amino) cyclohexyl)ethyl-6-methoxy-2,3,4,5-tetrahydro-1H-3-benzazapine Mass spectrum (API$^+$): Found 403 (MH$^+$). C$_{24}$H$_{38}$N$_2$O$_3$ requires 402.

b) trans-3-(2-(1-(4-N-tert-Butyloxycarbonyl)amino) cyclohexyl)ethyl-7-cyano-2,3,4,5-tetrahydro-1H-3-benzazepine Mass spectrum (API$^+$) Found 398 (MH$^+$). C$_{24}$H$_{35}$N$_3$O$_2$ requires 397. $^1$H NMR (CDCl$_3$) δ: 0.97–1.13 (4H, m), 1.22 (1H, m), 1.36–1.47 (11H, m), 1.71–1.79 (2H, m), 1.95–2.04 (2H, m), 2.48 (2H, m), 2.61 (4H, m), 2.90–3.00 (4H, m), 3.37 (1H, m), 4.35 (1H, m), 7.17 (1H, d, J=5 Hz), 7.36 (1H, s), 7.52 (1H, d, J=5 Hz).

DESCRIPTION 3 trans-3-(2-(1-(4-Amino)cyclohexyl)ethyl)-2,3,4,5-tetrahydro-1H-3-benzazepine

A mixture of trans-2-(2-(1-(4-(N-tert-butoxcarbonyl) amino)cyclohexyl)ethyl)-2,3,4,5-tetrahydro-1H-3-benzazepine (3.1 g, 8.3 mmol) and trifluoroacetic acid (5 ml) in CH$_2$Cl$_2$ (50 ml) was stirred at room temperature for 1 h, then at 40° C. for 1 h. The reaction mixture was then diluted with CH$_2$Cl$_2$ (100 ml) and washed with saturated aqueous K$_2$CO$_3$ (2×100 ml). The organic layer was dried over Na$_2$SO$_4$ and evaporated in vacuo to give the title compound as a brown oil (2.14 g, 95%).

Mass spectrum (API$^+$): Found: 273 (MH$^+$). C$_{18}$H$_{28}$N$_2$ requires 272.

The following compound was prepared in a similar manner to Descripton 3

(a) trans-3-(2-(1-(4-Amino)cyclohexyl)ethyl)-6-methoxy-2,3,4,5-tetrahydro-1H-3-benzazepine Mass spectrum (API$^+$): Found: 303 (MH$^+$). C$_{19}$H$_{30}$N$_2$O requires 302.

b) trans-3-(2-(1-(4-Amino)cyclohexyl)ethyl)-7-cyano-2,3,4,5-tetrahydro-1H-3-benzazepine Mass spectrum (API$^+$): Found: 298 (MH$^+$). C$_{19}$H$_{27}$N$_3$ requires 297. $^1$H NMR (CDCl$_3$) δ: 0.92–1.18 (6H, m), 1.21 (1H, m), 1.41 (2H, m), 1.75 (2H, m), 1.85 (2H, m), 2.49 (2H, m), 2.60 (5H, m), 2.95 (4H, m), 7.16 (1H, d, J=5 Hz), 7.36 (1H, s), 7.40 (1H, d, J=5 Hz).

DESCRIPTION 4 trans-2-(1-(4-(N-tert-Butyloxycarbonyl)amino) cyclohexyl)acetic Acid, Methyl Ester A mixture of trans-(4-amino)cyclohexylactic acid hydrogen sulfate (T. P. Johnston et al; J. Med Chem., 1977, 20 (2), 279–290), (27.0 g, 106 mmol), conc. H$_2$SO$_4$ (3 ml), and methanol (300 ml) was stirred at reflux for 5 h. Resulting solution was filtered and the filtrate evaporated in vacuo to give a brown oil (36 g). A mixture of this material, triethylamine (36 ml; 26.1 g, 259 mmol), dichloromethane (600 ml) and di-t-butyl dicarbonate (25.5 g, 117 mmol) was stirred at 20° C. for 18 h. Resulting solution was partitioned between saturated aqueous NaHCO$_3$ (500 ml) and dichloromethane (3×200 ml), and the combined extracts were dried (Na$_2$SO$_4$) and evaporated in vacuo to give the title compound (24.6 g, 86%) as a colourless solid.

$^1$H NMR (CDCl$_3$) δ: 1.08 (4H, m), 1.43 (9H, s), 1.76 (3H, m), 2.00 (2H, m), 2.20 (2H, d, J=7 Hz), 3.37 (1H, m), 3.66 (3H, s), 4.39 (1H, br s).

DESCRIPTION 5 trans-2-(1-(4-(N-tert-Butyloxycarbonyl)amino) cyclohexyl)acetaldehyde

To a stirred solution of trans-2-(1-(4-(N-tert-butyloxycarbonyl)amino)cyclohexyl)acetic acid, methyl ester (46.0 g, 170 mmol) in dry toluene (920 ml) at −78° C. under argon was added a solution of di-isobutylaluminium hydride (1M; 285 ml; 285 -mmol), dropwise over 0.5 h. Resulting solution was stirred for a further 0.3 h and quenched with a mixture of methanol (28 ml) in toluene (50 ml) and then poured into saturated aqueous potassium sodium tartrate (1.2 L). The resultant mixture was extracted with ether (4×1 L). The combined organic extracts were dried (Na$_2$SO$_4$) and evaporated in vacuo to give a waxy solid which was purified using silica gel, eluting with 10–50% ethyl acetate/hexane to give the title compound (21.77 g, 53%) as a colourless solid.

$^1$H NMR (CDCl$_3$) δ: 1.12 (4H, m), 1.44 (9H, s), 1.78 (3H, m), 2.00 (2H, m), 2.33 (2H, dd, J=7, 2 Hz), 3.37 (1H, m), 4.40 (1H, m), 9.75 (1H, m).

DESCRIPTION 6

7-Hydroxy-2,3,4,5-tetrahydro-1H-3-benzazepine, Hydrobromide

7-Methoxy-2,3,4,5-tetrahydro-1H-3-benzazepine (10 g) in 48% aqueous hydrobromic acid (350 ml) was allowed to stir at 100° C. for 4 h. The mixture was cooled to 20° C. then evaporated to dryness in vacuo to give the title compound (14.5 g) as a brown solid.

Mass spectrum (API$^+$): Found 164 (MH$^+$). C$_{10}$H$_{13}$NO requires 163. $^1$H NMR (DMSO) δ: 2.80–3.25 (8H, m), 4.42 (2H, br s), 6.50–6.70 (2H, m), 6.98 (1H, d, J=8 Hz), 8.86 (1H, brs).

DESCRIPTION 7

3-(tert-Butyloxycarbonyl)-7-hydroxy-2,3,4,5-tetrahydro-1H-3-benzazepine

To a solution of 7-hydroxy-2,3,4,5-tetrahydro-1H-3-benzazepine, hydrobromide (14.5 g) in tetrahydrofuran (100 ml) and water (70 ml), was added triethylamine (8 g), followed by a solution of di-tert-butyl dicarbonate (14 g) in THF (20 ml). The resulting mixture was allowed to stir at 20° C. for 16 h, partitioned between ethyl acetate (200 ml) and water (200 ml). The aqueous layer was washed with ethyl acetate (100 ml). The combined organic extracts were washed with saturated aqueous sodium bicarbonate (100 ml), dried ($Na_2SO_4$) and evaporated to dryness in vacuo. The resulting oil was purified by silica gel chromatography. Elution with ethyl acetate in hexane (10%–30%) gave the title compound (8 g).

Mass spectrum ($API^+$): Found 164 ($MH^+$—Boc). $C_{15}H_{21}NO_3$ requires 263. $^1H$ NMR ($CDCl_3$) δ: 1.48 (9H, s), 2.75–2.87 (4H, m), 3.40–3.60 (4H, m), 4.95 (1H, s), 6.50–6.62 (2H, m), 6.96 (1H, d, J=8 Hz).

DESCRIPTION 8

3-(tert-Butyloxycarbonyl)-7-trifluoromethylsulfonyloxy-2,3,4,5-tetrahydro-1H-3-benzazepine To a stirred mixture of 3-(tert-butyloxycarbonyl)-7-hydroxy-2,3,4,5-tetrahydro-1H-3-benzazepine (7 g) and triethylamine (5.4 ml) in dry dichloromethane under argon at −20° C., was added, dropwise, trifluoromethanesulfonic anhydride (5 ml). The resulting mixture was allowed to warm slowly to 20° C. over 16 h, then was poured into saturated aqueous sodium bicarbonate (200 ml) and extracted with dichloromethane (2×150 ml). The combined organic extracts were washed with brine (150 ml), dried ($Na_2SO_4$) and evaporated in vacuo to give an amber oil. Silica gel chromatography, eluting with ethyl acetate in hexane (10%–30%) gave the title compound (7 g) as an amber oil.

Mass spectrum ($API^+$): Found 396 ($MH^+$). $C_{16}H_{20}F_3NO_5S$ requires 395. $^1H$ NMR ($CDCl_3$) δ: 1.48 (9H, s), 2.85–2.95 (4H, m), 3.5–3.65 (4H, m), 7.00–7.05 (2H, m), 7.15–7.27 (1H, m).

DESCRIPTION 9

3-(tert-Butyloxycarbonyl)-7-cyano-2,3,4,5-tetrahydro-1H-3-benzazepine

A mixture of 3-(tert-butoxycarbonyl)-7-trifluoromethylsulfonyloxy-2,3,4,5-tetrahydro-1H-3-benzazepine (4.78 g, 12.1 mmol), zinc cyanide (1.42 g, 15.6 mmol) and tetrakis-triphenylphosphine palladium (0) (1.4 g, 1.2 mmol, 10 mol %), in dry dimethylformamide (50 ml) was stirred at 100° C. for 3 h under argon. After cooling to room temperature the reaction mixture was diluted with ethyl acetate (120 ml) and filtered. The filtrate was washed with saturated aqueous sodium bicarbonate (100 ml), then water (2×50 ml), then brine (50 ml). The organic layer was dried over sodium sulfate and evaporated in vacuo to give brown oil, which was purified by chromatography on silica gel with 20–100% ethyl acetate-hexane elution to give the title compound (0.765 g, 23%) as a brown oil.

Mass spectrum ($API^+$): Found 173 ($MH^+$—Boc). $C_{16}H_{20}N_2O_2$ requires 272. $^1H$ NMR ($CDCl_3$) δ: 1.47 (9H, s), 2.93 (4H, m), 3.56 (4H, m), 7.21 (1H, d, J=8 Hz), 7.42 (2H, m).

DESCRIPTION 10

7-Cyano-2,3,4,5-tetrahydro-1H-3-benzazepine

A mixture of 3-(tert-butoxycarbonyl)-7-cyano-2,3,4,5-tetrahydro-1H-3-benzazepine (765 mg, 2.81 mmol) and trifluoroacetic acid (2 ml), in dichloromethane (20 ml) was stirred at 40° C. for 1 h. The reaction mixture was evaporated to dryness in vacuo and partitioned between ethyl acetate (50 ml) and water (50 ml). The aqueous layer was basified using potassium carbonate and re-extracted with ethyl acetate (2×30 ml). The combined basic organic extracts were dried over sodium sulfate and evaporated in vacuo to give the title compound as a colourless oil (212 mg, 44%).

Mass spectrum ($API^+$): Found 173 ($MH^+$). $C_{11}H_{12}N_2$ requires 172. $^1H$ NMR ($CDCl_3$) δ: 2.04 (1H, br s), 2.95 (8H, m), 7.18 (1H, d, J=8 Hz), 7.38 (2H, m).

DESCRIPTION 11

7-Acetyl-trans-3-(2-(1-(4-N-tert-butoxycarbonyl)amino)cyclohexyl)ethyl-2,3,4,5-tetrahydro-1H-3-benzazepine Mass spectrum ($API^+$): Found 415 ($MH^+$). $C_{25}H_{38}N_2O_3$ requires 414.

DESCRIPTION 12

7-Acetyl-trans-3-(2-(1-(4-amino)cyclohexyl)ethyl)-2,3,4,5-tetrahydro-1H-3-benzazepine Mass spectrum ($API^+$): Found 315 ($MH^+$) $C_{20}H_{30}N_2O$ requires 314. $^1H$ NMR ($CDCl_3$) δ: 0.80–1.30 (5H, m), 1.41 (4H, m), 1.65–1.85 (4H, m), 2.48 (2H, m), 2.57 (3H, s), 2.60 (5H, m), 2.97 (4H, m), 7.17 (1H, d, J=8 Hz), 7.70 (2H, m).

DESCRIPTION 13

7-Acetyl-3-(tert-butyloxycarbonyl)-2,3,4,5-tetrahydro-1H-3-benzazepine

To a stirred solution of 3-(tert-butyloxycarbonyl)-7-trifluoromethylsulfonyloxy-2,3,4,5-tetrahydro-1H-3-benzazepine (10 g, 25.3 mmol) in anhydrous dimethylformamide (100 ml) under argon at room temperature, was added triethylamine (7.05 ml, 50.6 mmol), butyl vinyl ether (16.4 ml, 126.6 mmol), 1,3-bis(diphenylphosphino)propane (0.412 g, 1 mmol) and palladium acetate (0.202 g, 0.9 mmol) sequentially. The resultant mixture was heated at 85° C. for 1.5 h and cooled to room temperature. 4% Aqueous hydrochloric acid (150 ml) was added and stirring continued for 0.5 h. The reaction mixture was extracted with dichloromethane (3×300 ml) and the combined organics washed with water (4×500 ml), dried ($Na_2SO_4$) and evaporated in vacuo to afford a brown gum. Chromatography on silica gel with 0–30% ethyl acetate-hexane gradient elution gave the title compound (5.8 g, 79%) as a colourless solid.

$^1H$ NMR ($CDCl_3$) δ: 1.49 (9H, s), 2.58 (3H, s), 2.96 (4H, m), 3.57 (4H, m), 7.21 (1H, d, J=8 Hz), 7.72 (2H, m).

DESCRIPTION 14

7-Acetyl-2,3,4,5-tetrahydro-1H-benzazepine

Prepared from 7-acetyl-3-(tert-butyloxycarbonyl)-2,3,4,5-tetrahydro-1H-3-benzazepine (6.3 g, 21.8 mmol) using the method of Description 10 to afford a pale yellow oil (4.12 g, 100%).

$^1H$ NMR ($CDCl_3$) δ: 1.89 (1H, s), 2.58 (3H, s), 2.97 (8H, s), 7.17 (1H, d, J=8 Hz), 7.70 (2H, m).

DESCRIPTION 15

3-(3-Bromophenyl)-5-methyl-1,2,4-oxadiazole

Potassium tert-butoxide (7.33 g, 65.4 mmol) was added over 5 minutes to ice chilled, stirred methanol under argon.

After a further 5 min hydroxylamine hydrochloride (4.9 g, 70.43 mmol) was added in one portion and the resultant mixture stirred at room temperature for 1 h. A solution of 3-bromobenzonitrile (7.93 g, 43.6 mmol) in methanol (120 ml) was added in one portion and the mixture heated at reflux for 4 h, cooled filtered, and the filtrate evaporated in vacuo. The residue was refluxed in acetic anhydride (60 ml) for 3 h, cooled to room temperature and poured into ice-water (300 ml). The precipitate was filtered, washed with water, dried in vacuo and chromatographed on silica eluting with 0–10% ethyl, acetate-hexane gradient. Fractions containing desired product were pooled and evaporated in vacuo and the residue recrystallised from hexane to afford the title compound as colourless crystals (5.2 g, 50%).

Mass spectrum: (API$^+$) Found: 239 (MH$^+$). $C_9H_7^{79}BrN_2O$ requires 238 $^1$H NMR (CDCl$_3$) δ: 2.66 (3H, s), 7.36 (1H, t, J=8 Hz), 7.63 (1H, m), 8.05 (1H, m), 8.23 (1H, m).

DESCRIPTION 16

3-(5-Methyl-1,2,4-oxadiazol-3-yl)-benzoic Acid

A mixture of 3-(3-bromophenyl)-5-methyl-1,2,4-oxadiazole (2.68 g, 11.3 mmol), tributylamine (3.05 ml, 12.5 mmol) and trans-dibromobis(triphenylphosphine)palladium (II) (0.13 g, 0.16 mmol) in methanol (5 ml) was carbonylated at 30 psi and 100° C. for 18 h. The mixture was cooled to room temperature, diluted with ethyl acetate (100 ml) and washed sequentially with saturated sodium hydrogen carbonate (2×300 ml), brine (100 ml), 0.5 N hydrochloric acid (200 ml), brine (100 ml), then dried Na$_2$SO$_4$) and evaporated in vacuo to afford a yellow oil (2.49 g). A 2 g sample of this oil was dissolved in aqueous methanol (5:3, 80 ml), sodium hydroxide (0.36 g) added and the mixture stirred at room temperature for 20 h. The mixture was evaporated in vacuo and the residue partitioned between ethyl acetate (100 ml) and water (100 ml). The aqueous layer was acidified with 2N HCl and the resultant precipitate filtered, washed with water and dried in vacuo to afford the title compound as a colourless solid (0.78 g, 42%).

Mass spectrum: (API$^+$) Found: 205 (MH$^+$). $C_{10}H_8N_2O_3$ requires 204. $^1$H NMR (CDCl$_3$) δ: 2.70 (3H, s), 7.71 (1H, m), 8.14 (1H, dd, J=7,1 Hz), 8.23 (1H, dd, J=7, 1 Hz), 8.54 (1H, m), 13.35 (1H, br s).

DESCRIPTION 17

3-(1-Pyrazolyl)-benzoic Acid

A mixture of 3-hydrazinobenzoic acid (1.52 g, 0.01 mmol) and malondialdehydebis(dimethylacetal) (2.39 ml; 0.01 mol) in ethanol (10 ml) and water (15 ml) was heated at reflux for 2 h. The resulting solution was cooled and evaporated to afford the title product (1.8 g,; 96%) as a yellow solid.

$^1$H NMR (DMSO-d$_6$) δ: 6.60 (1H, t, J=2 Hz), 7.65 (1H, t, J=8 Hz), 7.81 (1H, d, J=1.5 Hz), 7.89 (1H, dd, J=8 and 1.5 Hz), 8.12 (1H, dd, J=8 and 1.5 Hz), 8.4 (1H, d, J=2 Hz), 8.64 (H,d, J=2 Hz).

Mass spectrum (API$^+$): Found 189 (MH$^+$). $C_{10}H_8N_2O_2$ requires 188.

DESCRIPTION 18

3-(tert-Butoxycarbonyl)-7-(3-(5-methyl)-1,2,4-oxadiazolyl)-2,3,4,5-tetrahydro-1H-3-benzazepine To a suspension of sodium methoxide (0.6 g, 11 mmol) in anhydrous methanol (12 ml) under argon, was added hydroxylamine hydrochloride (0.76 g, 11 mmol), followed by 3-(tert-butyloxycarbonyl)-7-cyano-2,3,4,5-tetrahydro-1H-3-benzazepine (1.5 g, 5.5 mmol). The mixture was stirred under reflux for 16 h, then allowed to cool to room temperature. The methanol was evaporated in vacuo and the resulting residue partitioned between dichloromethane (100 ml) and water (100 ml). The aqueous layer was washed with more CH$_2$Cl$_2$ (100 ml). The combined organic extracts were dried and evaporated in vacuo to give a solid (1.8 g), which was mixed with acetic anhydride (15 ml) and heated at 120° C. for 2 h. Excess acetic anhydride was evaporated in vacuo and the resulting oily residue partitioned between CH$_2$Cl$_2$ (250 ml) and saturated sodium bicarbonate solution (250 ml). The organic layer was washed with more bicarbonate solution (200 ml), dried, and evaporated to give an oil. Gravity silica gel chromatography eluting with ethyl acetate in hexane gave the title compound (3.2 g, 73%) as a colourless oil.

$^1$H NMR (CDCl$_3$) δ: 1.49 (9H, s), 2.65 (3H, s), 2.96 (4H, m), 3.58 (4H, m), 7.22 (1H, d, J=8 Hz), 7.80 (2H, m).

DESCRIPTION 19

7-(3-(5-Methyl)-1,2,4-oxadiazolyl)-2,3,4,5-tetrahydro-1H-3-benzazepine

A solution of 3-(tert-butoxycarbonyl)-7-(3-(5-methyl)-1,2,4-oxadiazolyl)-2,3,4,5-tetrahydro-1H-3-benzazepine (1.2 g, 3.6 mmol) in CH$_2$Cl$_2$ (15 ml) and trifluoroacetic acid (15 ml) was heater under reflux for 2 h. Solvent was evaporated in vacuo and the residue partitioned between diethyl ether (50 ml) and water (50 ml). The aqueous layer was saturated with potassium carbonate then extracted with CH$_2$Cl$_2$ (2×100 ml). The combined organic extracts were dried and evaporated in vacuo to give the title compound (0.74 g, 88%) as an oil.

Mass spectrum (API$^+$): Found 230 (MH$^+$). $C_{13}H_{15}N_3O$ requires 229. $^1$H NMR (CDCl$_3$) δ: 1.80 (1H, br s), 2.65 (3H, s), 2.90–3.00 (8H, m), 7.20 (1H, d, J=8 Hz), 7.75–7.85 (2H, m).

DESCRIPTION 20

7-(3-(tert-Butoxycarbonyl)-2,3,4,5-tetrahydro-1H-3-benzazepinyl)carboxamide

To a solution of 3-tert-butyloxycarbonyl)-7-cyano-2,3,4,5-tetrahydro-1H-3-benzazepine (5.44 g, 20 mmol) cooled in ice bath, was added potassium carbonate (0.4 g) in water (1 ml), followed by dropwise addition of 30% w/w hydrogen peroxide (2.4 ml). The resulting mixture was stirred at 5° C. for 5 min, then the ice-bath was removed. After another 5 min, water (100 ml) was added. The solid precipitate was collected by filtration and dried to give the title compound (4.35 g, 75%) as a colourless solid.

$^1$H NMR (CDCl$_3$) δ: 1.48 (9H, s), 2.96 (4H, m), 3.56 (4H, m), 5.60–6.30 (2H, br d), 7.19 (1H, d, J=8 Hz), 7.50–7.80 (2H, m).

DESCRIPTION 21

3-(tert-Butoxycarbonyl)-7-(5-(3-methyl)-1,2,4-oxadiazolyl)-2,3,4,5-tetrahydro-1H-3-benzazepine A mixture of 7-(3-tert-butoxycarbonyl)-2,3,4,5-tetrahydro-1H-3-benzazepinyl)carboxamide (4.29 g, 14.8 mmol) and N,N-dimethyl acetamide dimethyl acetal (6 ml, 41 mmol) was heated at 125° C. under argon. Methanol was removed from the reaction by means of a distillation condenser over 2 h. The reaction mixture was further evaporated in vacuo to give a thick brown oily residue. To this residue was added, in order, dioxan (10 ml), 5M sodium hydroxide (4 ml), hydroxylamine hydrochloride (1.4 g, 20 mmol) and 70% aqueous acetic acid (20 ml). The combined mixture was allowed to stir at room temperature for 15 min and then at 90° C. for 1 h. The mixture was treated with water (100 ml) and extracted with $CH_2Cl_2$ (2×150 ml). Combined organic extracts were washed with saturated sodium bicarbonate (100 ml), dried and evaporated in vacuo to give an oil. Gravity silica gel chromatography, eluting with ethyl acetate in hexane, gave the title compound (3.9 g, 80%) as a colourless solid.

$^1$H NMR (CDCl$_3$) δ: 1.49 (9H, s), 2.47 (3H, s), 2.98 (4H, m), 3.60 (4H, m), 7.27 (1H, d, J=8 Hz), 7.80–7.90 (2H, m).

DESCRIPTION 22

7-(5-(3-Methyl)-1,2,4-oxadiazolyl)-2,3,4,5-tetrahydro-1H-3-benzazepine

A solution of 3-(tert-butoxycarbonyl)-7-(5-(3-methyl)-1,2,4-oxadiazolyl)-2,3,4,5-tetrahydro-1H-3-benzazepine (3.8 g, 11.6 mmol) in $CH_2Cl_2$ (50 ml) and trifluoroacetic acid (12 ml) was heated under reflux for 2 h. Solvent was evaporated in vacuo and the residue partitioned between diethyl ether (200 ml) and water (200 ml). The aqueous layer was saturated with potassium carbonate then extracted with $CH_2Cl_2$ (3×200 ml). The combined organic extracts were dried and evaporated in vacuo to give the title compound (2.4 g, 91%) as a colourless solid.

Mass spectrum (API$^+$): Found 230 (MH$^+$). $C_{13}H_{15}N_3O$ requires 229. $^1$H NMR (CDCl$_3$) δ: 1.86 (1H, br s), 2.47 (3H, s), 3.00 (8H, m), 7.25 (1H, d, J=8 Hz), 7.80–7.90 (2H, m).

DESCRIPTION 23 trans-3-(2-(1-(4-N-tert-Butyloxycarbonyl)amino) cyclohexyl)ethyl-7-(3-(5-methyl)-1,2,4-oxadiazolyl)-2,3,4,5-tetrahydro-1H-3-benzazepine Prepared from 7-(3-(5-methyl)-1,2,4-oxadiazolyl)-2,3,4,5-tetrahydro-1H-3-benzazepine in a manner similar to Description 2, in 96% yield.

Mass spectrum (API$^+$): Found 455 (MH$^+$). $C_{26}H_{38}N_4O_3$ requires 454. $^1$H NMR (CDCl$_3$) δ: 0.90–1.10 (4H, m), 1.15–1.25 (1H, m), 1.38–1.47 (11H, m), 1.73–1.85 (2H, m), 1.93–2.05 (2H, m), 2.40–2.55 (2H, m), 2.56–2.70 (7H, m), 2.90–3.05 (4H, m), 3.35 (1H, br s), 4.35 (1H, br s), 7.19 (1H, d, J=8 Hz), 7.75–7.85 (2H, m).

DESCRIPTION 24 trans-3-(2-(1-(4-N-tert-Butyoxycarbonyl)amino) cyclohexyl)ethyl-7-(5-(3-methyl)-1,2,4-oxadiazolyl)-2,3,4,5-tetrahydro-1H-3-benzazepine Prepared from 7-(5-(3-methyl)-1,2,4-oxadiazolyl)-2,3,4,5-tetrahydro-1H-3-benzazepine in a manner similar to Description 2, in 94% yield.

Mass spectrum (API$^+$): Found 455 (MH$^+$). $C_{26}H_{38}N_4O_3$ requires 454. $^1$H NMR (CDCl$_3$) δ: 0.95–1.10 (4H, m), 1.23 (1H, br s), 1.40–1.50 (11H, m), 1.70–1.85 (2H, m), 1.95–2.10 (2H, m), 2.46 (3H, s), 2.46–2.52 (2H, m), 2.60–2.70 (4H, m), 2.90–3.60 (4H, m), 3.35 (1H, m), 4.35 (1H, m), 7.23 (1H, d, J=8 Hz), 7.80–7.90 (2H, m).

DESCRIPTION 25 trans-3-(2-(1-(4-Amino)cyclohexyl)ethyl)-7-(3-(5-methyl)-1(2,4-oxadiazoly()-2,3,4,5-tetrahydro-1H-3-benzazepine Prepared from trans-3-(2-(1-(4-N-tert-butyloxycarbonyl) amino)cyclohexyl)ethyl-7-(3-(5-methyl)-1,2,4-oxadiazolyl)-2,3,4,5-tetrahydro-1H-3-benzazepine in a manner similar to Description 3, in 100% yield.

Mass spectrum (API$^+$): found 355 (MH$^+$). $C_{21}H_{30}N_4O$ requires 354. $^1$H NMR (CDCl$_3$) δ: 0.90–1.10 (4H, m), 1.40 (2H, br s), 1.12–1.25 (1H, m), 1.40–1.50 (2H, m), 1.70–1.80 (2H, m), 1.80–1.90 (2H, m), 2.40–2.50 (2H, m), 2.55–2.70 (8H, m), 2.90–3.00 (4H, m), 7.19 (1H, d, J=8 Hz), 7.75–7.85 (2H, m).

DESCRIPTION 26 trans-3-(2-(1-(4-Amino)cyclohexyl)ethyl)-7-(5-(3-methyl)-1,2,4-oxadiazolyl)-2,3,4,5-tetrahydro-1H-3-benzazepine Prepared from trans-3-(2-(1-(4-N-tert-butyloxycarbonyl) amino)cyclohexyl)ethyl-7-(5-(3-methyl)-1,2,4-oxadiazolyl)-2,3,4,5-tetrahydro-1H-3-benzazepine in a manner similar to Description 3, in 100% yield.

Mass spectrum (API$^+$): Found 355 (MH$^+$). $C_{21}H_{30}N_4O$ requires 354. $^1$H NMR (CDCl$_3$) δ: 0.90–1.30 (5H, m), 1.37–1.50 (2H, m), 1.64 (2H, br s), 1.70–1.95 (4H, m), 2.46 (3H, s), 2.46–2.70 (7H, m), 2.90–3.10 (4H, m), 7.24 (1H, d, J=8 Hz), 7.80–7.90 (2H, m).

DESCRIPTION 27

3-Acetyl-2,3,4,5-tetrahydro-1H-3-benzazepine

A solution of acetic anhydride (6.37 g, 0.062 mol) in dichloromethane (50 ml) was added dropwise to a stirred solution of 2,3,4,5-tetrahydro-1H-3-benzazepine (8.35 g, 0.057 mol) and triethylamine (8.7 ml) in dichloromethane (50 ml) at 0° C. under argon. After stirring at room temperature for 18 h, water (80 ml) was added and the organic layer separated. The organic layer was washed with 0.5 M hydrochloric acid (50 ml), saturated sodium bicarbonate solution (50 ml), water (50 ml) and then dried (Na$_2$SO$_4$). Evaporation of the solvent in vacuo gave the title compound (10.24 g, 95%) as a yellow oil which solidified on standing.

$^1$H NMR (CDCl$_3$) δ: 2.18 (3H, s), 2.85–3.00 (4H, m), 3.55–3.60 (2H, m), 3.72–3.80 (2H, m), 7.10–7.20 (4H, m). Mass Spectrum AP$^+$: Found 190 (MH$^+$). $C_{12}H_{15}NO$ requires 189.

DESCRIPTION 28

3-Acetyl-7-chlorosulphonyl-2,3,4,5-tetrahydro-1H-3-benzazepine

A solution of 3-acetyl-2,3,4,5-tetrahydro-1H-3-benzazepine (4.0 g, 0.021 mol) in dichloromethane (25 ml) was added dropwise to a stirred solution of chlorosulphonic acid in dichloromethane (25 ml) at −70° C. under argon. After warming to room temperature, the reaction was stirred for 18 h before being quenched in ice/water (200 ml). The resulting mixture was extracted with ethyl acetate (3×100 ml), dried (Na$_2$SO$_4$) and the solvent evaporated in vacuo to give the title compound (2.74 g, 45%) as a pale yellow solid.

$^1$H NMR: δ (CDCl$_3$): 2.21 (3H, s), 3.0–3.10 (4H, m), 3.60–3.70 (2H, m), 3.74–3.80 (2H, m), 7.35–7.40 (1H, m), 7.80–7.85 (2H, m). Mass spectrum AP$^+$: Found 288 & 290 (MH$^+$). $C_{12}H_{14}NSO_2Cl$ requires 287 & 289.

DESCRIPTION 29

3-Acetyl-7-methylsulphonyl-2,3,4,5-tetrahydro-1H-3-benzazepine

To a stirred solution of sodium sulphite (1.60 g, 12.6 mmol) and sodium hydrogen carbonate (1.14 g, 13.56 mmol) in water (25 ml) was added 7-3-acetyl-7-chlorosulfonyl-2,3,4,5-tetrahydro-1H-3-benzazepine (2.6 g, 9.04 mmol) in tetrahydrofuran (10 ml). The reaction mixture was then heated at 75° C. for 2 h, cooled to 30° C. and methyl iodide (2.8 ml, 45.20 mmol) added. After stirring at 50° C. for 24 h, the reaction mixture was cooled to room temperature and partitioned between water (50 ml) and ethyl acetate (100 ml). The aqueous layer was then separated and further extracted with ethyl acetate (2×80 ml). The combined organics were then dried ($Na_2SO_4$) and the solvent removed in vacuo to give the title compound (1.77 g, 73%) as a pale yellow solid.

$^1$H NMR ($CDCl_3$) 2.20 (3H, s), 2.99–3.05 (4H, m), 3.06 (3H, s), 3.61–3.64 (2H, m), 3.73–3.77 (2H, m), 7.32–7.37 (1H, m), 7.7–7.75 (2H, m). Mass Spectrum $AP^+$: Found 268 ($MH^+$). $C_{13}H_{17}NSO_3$ requires 267.

DESCRIPTION 30

7-Methylsulphonyl-2,3,4,5-tetrahydro-1H-3-benzazepine

A solution of 3-acetyl-7-methylsulphonyl-2,3,4,5-tetrahydro-1H-3-benzazepine (1.75 g, 6.55 mmol) in 5 M hydrochloric acid was heated at reflux for 18 h. The reaction mixture was then cooled to room temperature, basified to pH 12 with potassium carbonate and the solvent evaporated in vacuo. The solid residue was then extracted with ethyl acetate (5×60 ml) and the combined organics dried ($Na_2SO_4$). The solvent was then evaporated in vacuo to give the title compound (450 mg, 32%) as a pale yellow oil.

$^1$H NMR ($CDCl_3$) 1.88 (1H, br s), 2.95–3.13 (8H, m), 3.04 (3H, s), 7.25–7.30 (1H, d), 7.65–7.72 (2H, m). Mass Spectrum $AP^+$: Found 226 ($MH^+$). $C_{11}H_{15}NSO_2$ requires 225.

DESCRIPTION 31 trans-3-(2-(1-(4-(N-tert-Butyloxycarbonyl)amino) cyclohexyl)ethyl-7-methylsulphonyl-2,3,4,5-tetrahydro-1H-3-benzazepine A solution of 7-methylsulphonyl-2,3,4,5-tetrahydro-1H-3-benzazepine (1.0 g, 4.67 mmol) and trans-(1-(4-N-tert-butyloxycarbonyl)amino)cyclohexylacetaldehyde (0.8 g, 3.34 mmol) in dichloroethane (20 ml) was stirred at room temperature for 5 min before sodium triacetoxyborohydride (0.95 g, 4.49 mmol) was added in a single portion. After stirring at room temperature for 48 h, the reaction mixture was partitioned between water (50 ml) and dichloromethane (100 ml). The aqueous layer was separate, re-extracted with dichloromethane (2×50 ml) and the combined organic layers dried ($Na_2SO_4$). The solvent was then removed in vacuo to give a pale yellow solid which was purified by column chromatography (silica gel; ethyl acetate: methanol; 9:1) to give the title compound (1.35 g, 90%) as a colourless solid.

$^1$H NMR ($CDCl_3$): 0.99–1.14 (4H, m), 1.23–1.29 (1H, m), 1.41–1.46 (2H, m), 1.46 (9H, s), 1.73–1.79 (2H, m), 2.00–2.06 (2H, m), 2.50 (2H, t, J=7.6 Hz), 2.62–2.65 (4H, m), 2.99–3.02 (4H, m), 3.05 (3H, s), 3.38 (1H, br s), 4.38 (1H, br s), 7.27–7.30 (1H, d), 7.67–7.74 (2H, m). Mass spectrum: $AP^+$ Found: 351 ([M-BOC]$H^+$). $C_{24}H_{38}N_2SO_4$ requires 450.

DESCRIPTION 32 trans-3-(2-(1-(4-Amino)cyclohexyl)ethyl)-7-methylsulphonyl-2,3,4,5-tetrahydro-1H-3-benzazepine A solution of trans-3-(2-(1-(4-N-tert-butyloxycarbonyl) amino)cyclohexyl)ethyl-7-methylsulphonyl-2,3,4,5-tetrahydro-1H-3-benzazepine (1.3 g, 2.89 mmol) in dichloromethane (24 ml) and trifluoroacetic acid (6 ml) were stirred at room temperature for 2 h. The reaction mixture was then concentrated in vacuo and the residue partitioned between water (60 ml) and ethyl acetate (20 ml). The aqueous layer was separated, extracted with ethyl acetate (30 ml) and then basified to pH=14 with 40% sodium hydroxide. The oily suspension was then extracted with ethyl acetate (3×60 ml) and the combined organic layers dried ($Na_2SO_4$). The solvent was evaporated in vacuo to give the title compound (1.01 g, 100%) as an off-white solid.

$^1$H NMR ($CDCl_3$) δ: 0.90–1.12 (4H, m), 1.15–1.22 (1H, m), 1.35–1.40 (2H, m), 1.72–1.78 (2H, m), 1.82–1.90 (2H, m), 2.45–2.52 (2H, m), 2.55–2.62 (5H, m), 2.98–3.02 (4H, m), 3.04 (3H, s), 7.27 (1H, d, J=7.8 Hz), 7.56 (1H, s), 7.68 (1H, d). Mass spectrum: $AP^+$ 351 ($MH^+$): $C_{19}H_{30}N_2SO_2$ requires 350.

DESCRIPTION 33

3-(tert-Butyloxycarbonyl)-7-(5-(3-methyl) isoxazolyl)-2,3,4,5-tetrahydro-1H-3-benzazepine A mixture of 7-acetyl-3-(tert-butyloxycarbonyl)-2,3,4,5-tetrahydro-1H-3-benzazepine (6.18 g, 21.4 mmol) and dimethylacetamide dimethylacetal (8 ml) was stirred at 125° C. Methanol by-product was removed by means of a Dean-Stark apparatus. After 8 h, excess dimethyl acetamide dimethyl acetal was evaporated in vacuo to give a thick oily residue. Absolute ethanol (20 ml) and hydroxylamine hydrochloride (2.53 g, 36.4 mmol) were added and the resulting mixture was heated under reflux for 2 h. The ethanol was removed in vacuo and the crude product residue was purified by silica gel chromatography eluting with 10–100% ethyl acetate in hexane to give the title compound as a colourless oil (6.1 g, 87%).

Mass spectrum ($API^+$): Found 351 ($MNa^+$). $C_{19}H_{24}N_2O_3$ requires 328. $^1$H NMR ($CDCl_3$) δ: 1.49 (9H, s), 2.35 (3H, s), 2.90–3.00 (4H, m), 3.50–3.65 (4H, m), 6.31 (1H, s), 7.21 (1H, d, J=8 Hz), 7.50–7.53 (2H, m).

DESCRIPTION 34

7-(5-(3-Methyl)isoxazolyl)-2,3,4,5-tetrahydro-1H-3-benzazepine

A solution of 3-(tert-butyloxycarbonyl)-7-(5-(3-methyl) isoxazolyl)-2,3,4,5-tetrahydro-1H-3-benzazepine (5.1 g, 15.6 mmol) in $CH_2Cl_2$ (30 ml) and trifluoroacetic acid (10 ml) was heated under reflux for 2 h. Solvent was evaporated in vacuo and the residue partitioned between diethyl ether (150 ml) and water (150 ml). The aqueous phase was saturated with potassium carbonate then extracted with $CH_2Cl_2$ (2×200 ml). The combined organic extracts were dried and evaporated in vacuo to give the title compound (3.15 g, 88%).

Mass spectrum ($API^+$): Found 229 ($MH^+$). $C_{14}H_{16}N_2O$ requires 228. $^1$H NMR ($CDCl_3$) δ: 1.80 (1H, br s), 2.34 (3H, s), 2.90–3.10 (8H, m), 6.30 (1H, s), 7.17 (1H, d, J=8 Hz), 7.40–7.55 (2H, m).

DESCRIPTION 35 trans-3-(2-(1-(4-N-tert-Butyloxycarbonyl)amino) cyclohexyl)ethyl-7-(5-(3-methyl)isoxazolyl)-2,3,4,5-tetrahydro-1H-3-benzazepine Prepared from 7-(5-(3-methyl)isoxazolyl)-2,3,4,5-tetrahydro-1H-3-benzazepine in a manner similar to Description 2, in 92% yield.

Mass spectrum (API+): Found 454 (MH+). C$_{27}$H$_{39}$N$_{3}$O$_{3}$ requires 453. $^1$H NMR (CDCl$_3$) δ: 1.00–1.10 (4H, m), 1.15–1.25 (1H, m), 1.44 (9H, s), 1.55–1.70 (2H, m), 1.70–1.85 (2H, m), 1.95–2.05 (2H, m), 2.34 (3H, s), 2.45–2.55 (2H, m), 2.55–2.70 (4H, m), 2.90–3.00 (4H, m), 3.35 (1H, m), 4.30–4.40 (1H, m), 6.30 (1H, s), 7.16 (1H, d, J=8 Hz), 7.45–7.55 (2H, m).

DESCRIPTION 36 trans-3-(2-(1-(4-Amino)cyclohexyl)ethyl-7-(5-(3-methyl)isoxazolyl)-2,3,4,5-tetrahydro-1H-3-benzazepine Prepared from trans-3-(2-(1-(4-N-tert-butyloxycarbonyl)amino)cyclohexyl)ethyl-7-(5-(3-methyl)isoxazolyl)-2,3,4,5-tetrahydro-1H-3-benzazepine in a manner similar to Description 3 in 99% yield.

$^1$H NMR (CDCl$_3$) δ: 0.90–1.10 (4H, m), 1.15–1.25 (1H, m), 1.35–1.50 (4H, m), 1.70–1.80 (2H, m), 1.80–1.90 (2H, m), 2.34 (3H, s), 2.42–2.52 (2H, m), 2.55–2.72 (5H, m), 2.90–3.00 (4H, m), 6.30 (1H, s), 7.16 (1H, d, J=8 Hz), 7.45–7.55 (2H, m).

DESCRIPTION 37

3-(tert-Butyloxycarbonyl)-7-methanesulphonyloxy-2,3,4,5-tetrahydro-1H-3-benzazepine A solution of 3-(tert-butyloxycarbonyl)-7-hydroxy-2,3,4,5-tetrahydro-1H-3-benzazepine (3.0 g, 0.011 mol), methanesulphonylchloride (1.44 g, 0.013 mol), triethylamine (1.27 g, 0.013 mol) and dichloromethane (50 ml) was stirred at room temperature for 18 h. The reaction mixture was then partitioned between dichloromethane (50 ml) and a saturated solution of sodium hydrogen carbonate (50 ml). The organic layer was separated, washed with water (50 ml) and then dried (Na$_2$SO$_4$). The solvent was then evaporated in vacuo to give the title compound (3.85 g, 99%) as a pale yellow oil.

$^1$H NMR (CDCl$_3$) δ: 1.48 (9H, s), 2.86–2.92 (4H, m), 3.13 (3H, s), 3.53–3.56 (4H, m), 7.00–7.03 (2H, m), 7.13–7.16 (1H, m). Mass spectrum (AP+): Found 242 [M-BOC]H+. C$_{16}$H$_{23}$NSO$_5$ requires 341.

DESCRIPTION 38

7-Methanesulphonyloxy-2,3,4,5-tetrahydro-1H-3-benzazepine

A solution of 3-(tert-butyloxycarbonyl)-7-methanesulphonyloxy-2,3,4,5-tetrahydro-1H-3-benzazepine (3.8 g, 0.011 mol), trifluoroacetic acid (3.76 g, 0.033 mol) and dichloromethane (50 ml) was heated at 50° C. for 5 h. The solvents were then evaporated in vacuo and the residue partitioned between water (200 ml) and ethyl acetate (150 ml). The aqueous layer was removed and washed with ethyl acetate (100 ml) and then basified to pH 14 with 40% sodium hydroxide. The suspension was then extracted with ethyl acetate (3×150 ml) and the combined organic layers dried (Na$_2$SO$_4$). The solvents were evaporated in vacuo to give the title compound (2.15 g, 80%) as a colourless oil.

$^1$H NMR (CDCl$_3$) δ: 2.88–3.00 (8H, m), 3.13 (3H, s), 6.99–7.03 (2H, m), 7.12 (1H, d). Mass spectrum (AP+): Found 242 (MH)+. C$_{11}$H$_{15}$NSO$_3$ requires 241.

DESCRIPTION 39 trans-3-(2-(1-(4-N-tert-Butyloxycarbonyl)amino)cyclohexyl)ethyl-7-methanesulphonyloxy-2,3,4,5-tetrahydro-1H-3-benzazepine A mixture of 7-(methanesulphonyloxy)-2,3,4,5-tetrahydro-1H-3-benzazepine (2.0 g, 8.3 mmol) and trans-2-(1-(4-N-tert-butyloxycarbonyl)amino)cyclohexyl acetaldehyde (1.37 g, 5.7 mmol) in dichloroethane (30 ml) was stirred at room temperature for 5 min. before sodium triacetoxyborohydride (1.69 g, 7.98 mmol) was addded in a single portion. After stirring at room temperature for 48 h, a saturated solution of sodium hydrogen carbonate (50 ml) was added and the two layers separated. The aqueous layer was extracted with dichloromethane (3×60 ml) and the combined organic layers were dried (Na$_2$SO$_4$). The solvent was then evaporated in vacuo and the residue purified by column chromatography (silica gel, ethyl acetate) to give the title compound (2.54 g, 95%) as a white solid.

$^1$H NMR (CDCl$_3$) δ: 0.9–1.25 (7H, m), 1.44 (9H, s), 1.70–1.80 (2H, m), 1.90–2.05 (2H, m), 2.42–2.50 (2H, m), 2.55–2.65 (4H, m), 2;88–2.95 (4H, m), 3.12 (3H, s), 3.36 (1H, br s), 4.34 (1H, br s), 6.98–7.02 (2H, m), 7.08–7.12 (1H, d). Mass spectrum (AP+): Found 467 [MH+]. C$_{24}$H$_{38}$N$_2$SO$_5$ requires 466.

DESCRIPTION 40 trans-3-(2-(1-(4-Amino)cyclohexyl)ethyl)-7-methanesulphonyloxy-2,3,4,5-tetrahydro-1H-3-benzazepine A solution of trans-3-(2-(1-(4-N-tert-butyloxycarbonyl)amino)cyclohexyl)ethyl-7-methanesulphonyloxy-2,3,4,5-tetrahydro-1H-3-benzazepine, trifluoroacetic acid (8 ml) and dichloromethane (32 ml), were stirred at room temperature for 2 h, under argon. The solvents were then evaporated in vacuo and the residue partitioned between water (150 ml) and ethyl acetate (60 ml). The aqueous layer was removed and washed with ethyl acetate (50 ml). The aqueous layer was then basified to pH 14 with 40% sodium hydroxide. The suspension was then extracted with ethyl acetate (3×80 ml) and the combined organic layers dried (Na$_2$SO$_4$). The solvents were evaporated in vacuo to give the title compound (1.78 g, 93%) as an oil which crystallised on standing.

$^1$H NMR (CDCl$_3$) δ: 0.95–1.45 (7H, m), 1.70–1.86 (2H, m), 1.80–1.90 (2H, m), 2.49 (2H, t, J=7.8 Hz), 2.55–2.65 (5 H, m), 2.88–2.95 (4H, m), 3.12 (3H, s), 6.99–7.02 (2H, m), 7.11 (1H, d, J=8 Hz). Mass Spectrum (AP+): Found 367 (MH+). C$_{19}$H$_{30}$N$_2$SO$_3$ requires 366.

EXAMPLES

The Compounds of Examples tabulated below (Tables 1–3) were all prepared using the following general method:

A mixture of the appropriate trans-2-(2-(1-(4-amino)cyclohexyl)ethyl)-2,3,4,5-tetrahydro-1H-3-benzazepine (0.35 mmol), the appropriate acid (0.35 mmol), 1-ethyl-3-(3-dimethylaminopropyl)carbodiimide hydrochloride (0.35 mmol), 1-hydroxybenzotriazole (catalytic amount) and dichloromethane (5 ml) was shaken for 16 h. Saturated sodium bicarbonate (4 ml) was then added and the mixture shaken for 0.25 h. Chromatography of the organic layer on silica with 50–100% ethyl acetate in hexane and 0–10% methanol in ethyl acetate gradient elution gave the title compounds.

TABLE 1

[Structure: A benzazepine ring with R¹ substituent connected via ethyl linker to a cyclohexyl group bearing an NH-C(=O)-A amide]

| Example | R¹ | A | Characterising Data Mass Spectrum (API⁺); ¹H NMR (CDCl₃) |
|---|---|---|---|
| 1 | H | 4-Quinolinyl | Found: 428 (MH⁺). $C_{28}H_{33}N_3O$ requires 427.<br>δ: 1.06–1.37(5H, m), 1.47(2H, m), 1.78 (2H, m), 2.19(2H, m), 2.51(2H, m), 2.64 (4H, m), 2.93(4H, m), 4.03(1H, m), 5.90 (1H, d, J=8Hz), 7.10(4H, m), 7.40(1H, d, J=4Hz), 7.60(1H, m), 7.75(1H, m), 8.15(2H, m), 8.91(1H, d, J=4Hz). |
| 2 | H | trans-CH=CHC₆H₄(3-SO₂Me) | Found: 481(MH⁺). $C_{28}H_{36}N_2O_3S$ requires 480.<br>δ: 1.01–1.33(5H, m), 1.45(2H, m), 1.81 (2H, m), 2.02(2H, m), 2.50(2H, m), 2.63 (4H, m), 2.93(4H, m), 3.07(3H, s), 3.84 (1H, m), 5.64(1H, d, J=8Hz), 6.49(1H, d, J=16Hz), 7.09(4H, m), 7.64(3H, m), 7.89(1H, d, J=8Hz), 8.09(1H, s). |
| 3 | H | trans-CH=CHC₆H₄(4-F) | Found: 421(MH⁺). $C_{27}H_{33}FN_2O$ requires 420.<br>δ: 1.00–1.33(5H, m), 1.43(2H, m), 1.79 (2H, m), 2.04(2H, m), 2.49(2H, m), 2.62 (4H, m), 2.93(4H, m), 3.86(1H, m), 5.51 (1H, d, J=8Hz), 6.26(1H, d, J=16Hz), 7.11(6H, m), 7.47(2H, m), 7.56(1H, d, J=16Hz). |
| 4 | H | 2-Indolyl | Found: 416(MH⁺). $C_{27}H_{33}N_3O$ requires 415.<br>δ: 1.05–1.37(5H, m), 1.46(2H, m), 1.82 (2H, m), 2.12(2H, m), 2.52(2H, m), 2.63 (4H, m), 2.92(4H, m), 3.96(1H, m), 5.98 (1H, d, J=8Hz), 6.79(1H, m), 7.14(5H, m), 7.26(1H, m), 7.41(1H, m), 7.64(1H, d, J=8Hz), 9.35(1H, br s). |
| 5 | H | —C₆H₄(3-(3-pyridyl)) | Found: 454(MH⁺). $C_{30}H_{35}N_3O$ requires 453.<br>δ: 1.08–1.37(5H, m), 1.46(2H, m), 1.84 (2H, m), 2.12(2H, m), 2.51(2H, m), 2.63 (4H, m), 2.92(4H, m), 3.95(1H, m), 6.02 (1H, d, J=8Hz), 7.11(4H, m), 7.38(1H, m), 7.54(1H, t, J=8Hz), 7.72(2H, m), 7.91(1H, m), 7.98(1H, s), 8.62(1H, m), 8.86(1H, d, J=2Hz). |
| 6 | H | —CH₂Ph | Found 391(MH⁺). $C_{26}H_{34}N_2O$ requires 390.<br>δ: 0.87–1.14(5H, m), 1.40(2H, m), 1.68 (2H, m), 1.89(2H, m), 2.45(2H, m), 2.49 (4H, m), 2.89(4H, m), 3.54(2H, s), 3.68 (1H, m), 5.14(1H, m), 7.10(4H, m), 7.30 (5H, m). |
| 7 | H | —CH₂(3-indolyl) | Found: 430(MH⁺). $C_{28}H_{35}N_3O$ requires 429.<br>δ: 0.77–1.13(5H, m), 1.36(2H, m), 1.64 (2H, m), 1.84(2H, m), 2.42(2H, m), 2.57 (4H, m), 2.98(4H, m), 3.70(3H, m), 5.46 (1H, d, J=8Hz), 7.12(7H, m), 7.39(1H, d, J=8Hz), 7.53(1H, d, J=8Hz), 8.24 (1H, br s). |
| 8 | H | —CH₂(4-quinolyl) | Found: 442(MH⁺) $C_{29}H_{35}N_3O$ requires 441.<br>δ: 0.80–1.15(5H, m), 1.35–1.45(2H, m), 1.65–1.75(2H, m), 1.80–1.90(2H, m), 2.45–2.52(2H, m), 2.60–2.70(4H, m), 2.85–3.00(4H, m), 3.70(1H, m), 3.99 (2H, s), 5.13(1H, d, J=8Hz), 7.00–7.16 (4H, m), 7.33(1H, d, J=3Hz), 7.60(1H, m), 7.75(1H, m), 7.98(1H, d, J=8Hz), |

TABLE 1-continued

| Example | R¹ | A | Characterising Data Mass Spectrum (API⁺); ¹H NMR (CDCl₃) |
|---|---|---|---|
| | | | 8.14(1H, d, J=8Hz), 8.88(1H, d, J=3Hz). |
| 9 | 6-OMe | trans-CH=CHC₆H₄(4-F) | Found: 451(MH⁺), $C_{28}H_{35}FN_2O_2$ requires 450. δ: 1.10–1.30(5H, m), 1.40–1.50(2H, m), 1.75–1.85(2H, m), 2.00–2.10(2H, m), 2.40–2.52(2H, m), 2.55–2.70(4H, m), 2.85–3.10(4H, m), 3.80(3H, s), 3.86 (1H, m), 5.37(1H, d, J=8Hz), 6.26(1H, d, J=15Hz), 6.74(2H, m), 7.06(3H, m), 7.47(2H, dd, J=9Hz, 6Hz), 7.54(1H, d, J=15Hz). |
| 10 | 6-OMe | 4-Quinolyl | Found: 458(MH⁺), $C_{29}H_{35}N_3O_2$ requires 457 δ: 1.05–1.35(5H, m), 1.55–1.69(2H, m), 1.70–1.80(2H, m), 2.10–2.24(2H, m), 2.90–3.35(10H, m), 3.80(3H, s), 4.00(1H, m), 5.85(1H, d, J=8Hz), 6.75 (2H, m), 7.13(1H, t, J=8Hz), 7.41(1H, d, J=4Hz), 7.60(1H, m), 7.78(1H, m), 8.16 (2H, m), 8.94(1H, d, J=4Hz). |
| 11 | 6-OMe | 3-(pyrrolo[2,3-b]pyridyl) | Found: 447(MH⁺), $C_{27}H_{34}N_4O_2$ requires 446. δ: 1.30–1.35(5H, m), 1.45–1.55(2H, m), 1.75–1.80(2H, m), 2.10–2.20(2H, m), 2.55–2.85(6H, m), 2.90–3.20(4H, m), 3.80(3H, s), 3.96(1H, m), 5.65(1H, d, J=8Hz), 6.74(2H, m), 7.10(1H, t, J=8Hz), 7.20(1H, m), 7.80(1H, s), 8.35(2H, m), 9.45(1H, br s). |
| 30 | 7-CN | —CH₂Ph(2,5-diF) | Found: 452(MH⁺); $C_{27}H_{31}F_2N_3O$ requires 451. δ: 0.80–1.00(4H, m), 1.10(1H, m), 1.40–1.50(2H, m), 1.55–1.65(2H, m), 1.80–1.90(2H, m), 2.70–2.80(2H, m), 2.90–3.20(8H, m), 3.48(2H, s), 3.60(1H, m), 5.28(1H, d, J=8Hz), 6.90–7.05(3H, m), 7.21(1H, d, J=8Hz), 7.40(1H, s), 7.45 (1H, d, J=6Hz). |
| 31 | 7-CN | —CH₂(2-naphthyl) | Found: 466(MH⁺); $C_{31}H_{35}N_3O$ requires 465. δ: 0.80–1.20(5H, m), 1.30–1.40(2H, m), 1.65–1.75(2H, m), 1.85–1.90(2H, m), 2.35–2.50(2H, m), 2.50–2.60(4H, m), 2.85–3.00(4H, m), 3.60–3.85(3H, m), 5.16(1H, d, J=9hz), 7.10(1H, d, J=9Hz), 7.30–7.40(3H, m), 7.40–7.60(2H, m), 7.70(1H, s), 7.80–7.90(3H, m). |
| 32 | 7-CN | trans-CH=CHC₆H₃(2,4-diF) | Found: 464(MH⁺); $C_{28}H_{31}N_3OF_2$ requires 463. δ: 1.02–1.30(5H, m), 1.40–1.48(2H, m), 1.78–1.82(2H, m), 2.03–2.06(2H, m), 2.50(2H, t, J=8Hz), 2.62–2.66(4H, m), 2.93–3.00(4H, m), 3.79–3.91(1H, m), 5.72(1H, d, J=8Hz), 6.43(1H, d, J=16Hz), 6.75–6.95(2H, m), 7.18(1H, d, J=8 Hz), 7.38–7.47(3H, m), 7.59(1H, d, J=16Hz). |
| 33 | 7-CN | trans-CH=CHC₆H₃(2,5-diF) | Found: 464(MH⁺); $C_{28}H_{31}N_3OF_2$ requires 463. (CD₃OD) δ: 1.06–1.40(5H, m), 1.60–1.74(2H, m), 1.80–1.85(2H, m), 1.92–1.97(2H, m), 2.90–3.40(8H, m), 3.64–3.79(3H, m), 6.64(1H, d, J=16Hz), 7.09– |

TABLE 1-continued

| Example | R¹ | A | Characterising Data Mass Spectrum (API⁺); ¹H NMR (CDCl₃) |
|---|---|---|---|
| 34 | 7-CN | trans-CH=CHC₆H₄(3-F) | 7.18(2H, m), 7.29–7.39(2H, m), 7.52–7.58(3H, m). Found: 446(MH⁺); C₂₈H₃₂N₃OF requires 445. δ: 1.03–1.35(5H, m), 1.40–1.48(2H, m), 1.75–2.10(4H, m), 2.51(2H, t, J=8Hz), 2.61–2.65(4H, m), 2.93–2.99(4H, m), 3.72–3.88(1H, m), 6.36(1H, d, J=18Hz), 7.04(1H, m), 7.17–7.45(7H, m), 7.55(1H, d, J=16Hz) |
| 35 | | —CH₂CH₂C₆H₅ | Found: 430(MH⁺); C₂₈H₃₅N₃O requires 429. δ: 0.90–1.25(5H, m), 1.30–1.45(2H, m), 1.65–1.95(4H, m), 2.35–2.50(4H, m), 2.55–2.65(4H, m), 2.90–3.04(6H, m), 3.66–3.69(1H,m), 5.09(1H, d, J=8Hz), 7.15–7.35(6H, m), 7.37–7.42(2H, m). |
| 36 | 7-CN | trans-CH=CHC₆H₄(2-F) | Found: 446(MH⁺), C₂₈H₃₂FN₃O requires 445. δ: 1.00–1.30(5H, m), 1.40–1.50(2H, m), 1.75–1.85(2H, m), 2.00–2.10(2H, m), 2.45–2.50(2H, m), 2.60–2.70(4H, m), 2.85–3.00(4H, m), 3.80–3.95(1H, m), 5.43(1H, d, J=8Hz), 6.47(1H, d, J=16 Hz), 7.00–7.20(3H, m), 7.26–7.35(1H, m), 7.30–7.55(3H, m), 7.66(1H, d, J=16 Hz). |
| 37 | 7-CN | 8-(1,4-dihydro-4-oxo)-quinolinyl | Found: 469(MH⁺); C₂₉H₃₂N₄O₂ requires 468. δ: 1.05–1.35(5H, m), 1.40–1.50(2H, m), 1.80–1.90(2H, m), 2.10–2.20(2H, m), 2.45–2.55(2H, m), 2.60–2.70(4H, m), 2.90–3.00(4H, m), 3.95(1H, m), 6.30–6.40(2H, m), 7.18(1H, d, J=8Hz), 7.32(1H, t, J=8Hz), 7.37(1H, s), 7.41(1H, d, J=8Hz), 7.67(1H, t, J=5Hz), 7.80(1H, d, J=7Hz), 8.52(1H, d, J=8Hz), 12.50(1H, br s). |
| 38 | 7-CN | 2-naphthyl | Found: 452(MH⁺); C₃₀H₃₃N₃O requires 451. δ: 1.09–1.26(5H, m), 1.42–1.50(2H, m), 1.80–1.87(2H, m), 2.10–2.25(2H, m), 2.40–2.54(2H, m), 2.61–2.70(4H, m), 2.92–2.99(4H, m), 3.95–4.00(1H, m), 5.81(1H, d, J=8Hz), 7.18(1h, d, J=8Hz), 7.30–7.59(6H, m), 7.84–7.95(2H, m), 8.20–8.29(1H, m). |
| 39 | 7-CN | trans-CH=CHC₆H₄(2-OMe) | Found: 458(MH⁺); C₂₉H₃₅N₃O₂ requires: 457. (DMSO-d₆) δ: 0.99–1.07(2H, m), 1.15–1.28(3H, m), 1.35–1.40(2H, m), 1.78–1.88(4H, m), 2.46(2H, t, J=7Hz), 2.58(4H, m, obscurred by DMSO), 2.90–2.96(4H, m), 3.58–2.64(1H, m), 3.87(3H, s), 6.64(1H, d, J=16Hz), 6.99(1H, t, J=7Hz), 7.09(1H, d, J=8Hz), 7.34–7.39(2H, m), 7.49–7.51(1H, m), 7.58–7.66(3H, m), 7.93–7.96(1H, m). |
| 40 | 7-CN | trans-CH=CHC₆H₄(3-OMe) | Found: 458(MH⁺); C₂₉H₃₅N₃O₂ requires 457. (DMSO-d₆) δ: 0.80–0.98(2H, m), 1.00–1.20(3H, m), 1.20–1.35(2H, m), 1.78–1.82(2H, m), 1.88–1.92(2H, m), 2.49(2H, t, J=8Hz), 2.51–2.60(4H, m, obscurred by DMSO), 2.90–3.00(4H, m), |

TABLE 1-continued

| Example | R¹ | A | Characterising Data Mass Spectrum (API⁺); ¹H NMR (CDCl₃) |
|---|---|---|---|
| | | | 3.62(1H, m), 3.83(3H, s), 6.65(1H, d, J=16Hz), 7.00(1H, m), 7.15–7.17(2H, m), 7.35–7.43(3H, m), 7.61–7.63(2H, m), 7.99(1H, d, J=8Hz). |
| 41 | 7-CN | trans-CH=CHC₆H₄(4-OMe) | Found: 458(MH⁺); C₂₉H₃₅N₃O₂ requires: 457. (DMSO-d₆) δ: 1.00–1.10(2H, m), 1.15–1.27(3H, m), 1.38–1.41(2H, m), 1.77–1.80(2H, m), 1.85–1.87(2H, m), 2.47 (2H, t, J=7Hz), 2.53–2.57(4H, m, obscurred by DMSO), 2.91–2.97(4H, m), 3.58–3.65(1H, m), 3.81(3H, s), 6.48(1H, d, J=16Hz), 7.00(2H, m), 7.35–7.40 (2H, m), 7.51(2H, m), 7.58–7.52(2H, m), 7.88(1H, d, J=8Hz). |
| 42 | 7-CN | trans-CH=CHC₆H₄(2-COMe) | Found: 470(MH⁺); C₃₀H₃₅N₃O₂ requires 469. (DMSO-d₆) δ: 0.90–1.40(7H, m), 1.60–2.90(4H, m), 2.46(2H, t, J=8Hz), 2.46–2.54(4H, m, obscurred by DMSO), 2.52 (3H, s), 2.80–3.00(4H, m), 3.60(1H, m), 6.47(1H, d, J=16Hz), 7.35(2H, d, J=8Hz), 7.40–7.63(4H, m), 7.75(1H, d, J=16Hz), 7.89(1H, d, J=8Hz), 8.04(1H, d, J=8Hz). |
| 43 | 7-CN | trans-CH=CHC₆H₄(4-COMe) | Found: 470(MH⁺); C₃₀H₃₅N₃O₂ requires: 469. (DMSO-d₆): 0.90–1.40(7H, m), 1.73–1.88(4H, m), 2.43(2H, t, J=8Hz), 2.47–2.54(4H, m, obscurred by DMSO), 2.59 (3H, s), 2.80–2.93(4H, m), 3.50–3.70 (1H, m), 6.73(1H, d, J=16Hz), 7.32(1H, d, J=7hz), 7.45(1H, d, J=16Hz), 7.55–7.59(2H, m), 7.68(2H, d, J=8Hz), 7.98 (2H, m), 8.08(1H, d, J=8Hz). |
| 44 | 7-CN | trans-CH=CHC₆H₄(2-CN) | Found: 453(MH⁺); C₂₉H₃₂N₄O requires 452. (DMSO-d₆) δ: 1.02–1.09(2H, m), 1.10–1.35(3H, m), 1.36–1.42(2H, m), 1.78–1.81(2H, m), 1.88–1.90(2H, m), 2.47 (2H, t, J=7Hz), 2.50–2.59.(4H, m, obscurred by DMSO), 2.92–2.97(4H, m), 3.62–3.58(1H, m), 6.85(1H, d, J=16Hz), 7.36(1H, d, J=8Hz), 7.58–7.67 (4H, m), 7.79–7.89(2H, m), 7.92–7.95 (1H, m), 8.22–8.25(1H, m). |
| 45 | 7-CN | trans-CH=CHC₆H₄(3-CN) | Found: 453(MH⁺): C₂₉H₃₂N₄O requires: 452. (DMSO-d₆) δ: 0.94–1.38(7H, m), 1.70–1.87(4H, m), 2.43(2H, t, J=7Hz), 2.46–2.59(4H, m, obscurred by DMSO), 2.85–2.97(4H, m), 3.52–3.65(1H, m), 6.72 (1H, d, J=16Hz), 7.32(1H, d, J=8Hz), 7.42(1H, d, J=16Hz), 7.55–7.62(3H, m), 7.80–7.91(2H, m), 8.02(1H, s), 8.09 (1H, d, J=8Hz). |
| 46 | 7-CN | —C₆H₄(3-(5-(3-methyl)isoxazolyl) | Found: 483(MH⁺); C₃₀H₃₄N₄O₂ requires 482. (DMSO-d₆) δ: 0.96–1.10(2H, m), 1.23–1.50(5H, m), 1.70–1.89(4H, m), 2.31 (3H, s), 2.42–2.55(6H, m, obscurred by DMSO), 2.80–2.95(4H, m), 3.75(1H, m), 6.96(1H, s), 7.33(1H, d, J=8Hz), 7.50–7.60(3H, m), 7.90–8.00(2H, m), 8.28 (1H, m), 8.41(1H, d, J=8Hz). |

TABLE 1-continued

| Example | R¹ | A | Characterising Data Mass Spectrum (API⁺); ¹H NMR (CDCl₃) |
|---|---|---|---|
| 47 | 7-CN | 7-(1,2-dihydro-2-oxo)quinolinyl | Found: 469(MH⁺); $C_{29}H_{32}N_4O_2$ requires 468.<br>(DMSO–TFA) δ: 0.98–1.45(5H, m), 1.56–1.63(1.56–1.63(2H, m), 1.75–1.89 (4H, m), 2.95–3.32(8H, m), 3.65–3.85 (3H, m), 5.67(1H, s), 6.60(1H, d, J=10 10Hz), 7.41(1H, d, J=8Hz), 7.59–7.70 (4H, m), 7.75(1H, s), 7.90(1H, d, J= 10Hz), 8.32(1H, d), 9.69(1H, s). |
| 48 | 7-CN | cis-CH=CHC₆H₅ | Found: 428(MH⁺); $C_{28}H_{33}N_3O$ requires 427.<br>δ: 0.80–1.15(5H, m), 1.30–1.40(2H, m), 1.65–1.75(2H, m), 1.80–1.95(2H, m), 2.40–2.50(2H, m), 2.55–2.65(4H, m), 2.85–3.00(4H, m), 3.75(1H, m), 5.25 (1H, d, J=8Hz), 5.98(1H, d, J=12.5Hz), 6.76(1H, d, J=12.5Hz), 7.17(1H, d, J=8Hz), 7.30–7.45(7H, m). |
| 49 | 7-CN | trans-CH=CH(2-pyridyl) | Found: 429(MH⁺); $C_{27}H_{32}N_4O$ requires 428.<br>δ(DMSO+TFA): 0.90–1.30(5H, m), 1.55–1.70(2H, m), 1.70–1.80(2H, m), 1.80–1.90(2H, m), 2.90–3.30(8H, m), 3.50–3.80(3H, m), 7.08(1H, d, J=16Hz), 7.40–7.50(2H, m), 7.55–7.60(1H, m), 7.65–7.80(3H, m), 8.05(1H, m), 8.25(1H, d, J=8Hz), 8.70(1H, m). 9.70(1H, br q) |
| 50 | 7-CN | trans-CH=CH(1-(4-fluoro)naphthyl) | Found: 496(MH⁺); $C_{32}H_{34}FN_3O$ requires 495.<br>δ: (DMSOd₆ + TFA); 0.97–1.41(5H, m), 1.63(2H, m), 1.79(2H, m), 1.90(2H, m), 3.06(2H, m), 3.23(6H, m), 3.70(3H, m), 6.64(1H, d, J=16Hz), 7.47(2H, m), 7.73 (5H, m), 8.12(3H, m), 8.24(1H, m). |
| 51 | 7-CN | trans-CH=CH(6-benzodioxanyl) | Found: 486(MH⁺); $C_{30}H_{35}N_3O$ requires 485.<br>δ: (DMSOd₆+TFA): 0.93–1.33(5H, m), 1.60(2H, m), 1.81(4H, m), 3.04(2H, m), 3.17(6H, m), 3.67(3H, m), 4.26(4H, s), 6.42(1H, d, J=16Hz), 6.87(1H, d, J= 9Hz), 7.03(2H, m), 7.27(1H, d, J=16Hz), 7.46(1H, d, J=8Hz), 7.73(2H, m), 7.90 (1H, d, J=8Hz), 9.78(1H, br s). |
| 52 | 7-CN | trans-CH=CH(3-indolyl[5-F]) | Found: 485(MNa⁺); $C_{30}H_{33}FN_4O$ requires 484.<br>(DMSO-d₆) δ: 0.98–1.08(2H, m), 1.11–1.28(3H, m), 1.35–1.42(2H, m), 1.75–1.80(2H, m), 1.87–1.91(2H, m), 2.47 (2H, t, J=7Hz), 2.52–2.59(4H, m, obscurred by DMSO), 2.89–2.94(4H, m), 3.55–3.62(1H, m), 6.56(1H, d, J= 16Hz), 7.03–7.09(1H, m), 7.34(1H, d, J= 8Hz), 7.44–7.49(1H, m), 7.56–7.75(5H, m), 7.80(1H, s), 11.63(1H, s). |
| 53 | 7-CN | trans-CH=CH(6-benzimidazolyl[1-methyl] | Found: 482(MH⁺); $C_{30}H_{35}N_5O$ requires 481.<br>(DMSO-d₆) δ: 0.98–1.07(2H, m), 1.16–1.27(3H, m), 1.30–1.40(2H, m), 1.75–1.79(2H, m), 1.84–1.89(2H, m), 2.46 (2H, t, J=7Hz), 2.50–2.55(4H, m, obscurred by DMSO), 2.90–2.97(4H, m), 3.60–3.66(1H, m), 3.87(3H, s), 6.64(1H, d, J=16HZ), 7.34(1H, d, J=8Hz), 7.41– |

TABLE 1-continued

[Structure: benzazepine with R¹ substituent connected via ethyl linker to cyclohexyl-NH-C(=O)-A]

| Example | R¹ | A | Characterising Data Mass Spectrum (API⁺); ¹H NMR (CDCl₃) |
|---|---|---|---|
| 54 | 7-CN | trans-CH=CH(7-benzofuranyl) | 7.45(1H, m), 7.53–7.45(1H, m), 7.53–7.61(3H, m), 7.66(1H, d, J=8Hz), 7.77 (1H, s), 7.91–7.94(1H, m), 8.24(1H, s). Found: 468(MH⁺); C₃₀H₃₃N₃O₂ requires 467. (DMSO/TFA) δ: 1.02–1.43(5H, m), 1.65–1.75(2H, m), 1.75–2.00(4H, m), 3.08–3.35(8H, m), 3.65–3.80(3H, m), 7.09–7.15(2H, m), 7.36(1H, t); 7.48–7.56(2H, m), 7.66(1H, d, J=15.8Hz), 7.73–7.80 (3H, m), 8.15(1H, d, J=2.2Hz), 8.25(1H, d). |
| 55 | 7-CN | trans-CH=CH(5-indolyl[3-methyl]) | Found: 481(MH⁺) C₃₁H₃₆N₄O requires 480. (DMSO/TFA) δ: 0.95–1.35(5H, m), 1.55–1.70(2H, m), 1.70–1.95(4H, m), 2.27 (3H, s), 2.95–3.30(8H, m), 3.55–3.80 (3H, m), 6.52(1H, d, J=15.7Hz), 7.14 (1H, s), 7.33(2H, m), 7.46(2H, m), 7.71 (3H, m), 7.84(1H, d), 9.82(1H, br s). |
| 56 | 7-CN | trans-CH=CH(6-(2,3-dihydro-2-oxo)indolyl) | Found: 483(MH⁺); C₃₀H₃₄N₄O₂ requires 482. (DMSO) δ: 0.87–1.36(7H, m), 1.74–1.90 (4H, m), 2.44(2H, t, J=7.2Hz), 2.50–2.65(4H, m, under DMSO), 2.80–2.95 (4H, m), 3.49(2H, s), 3.57–3.70(1H, m), 6.54(1H, d, J=15.8Hz), 6.95(1H, s), 7.09(1H, d, J=8), 7.22(1H, d, J=7.5), 7.27–7.39(2H, m), 7.56–7.60(2H, m), 7.92(1H, d). |
| 57 | 7-CN | —CH₂(2-benzofuranyl) | Found: 456(MH⁺); C₂₉H₃₃N₃O₂ requires 455. (DMSO) δ: 0.95–1.23(5H, m), 1.31–1.36 (2H, m), 1.72–1.82(4H, m), 2.42(2H, t, J=7.4Hz), 2.49–2.53(4H, m, under DMSO), 2.88–2.93(4H, m), 3.47–3.52 (1H, m), 3.63(2H, s), 6.65(1H, s), 7.19–7.24(2H, m), 7.31(1H, d, J=7.7Hz), 7.49 (1H, d, J=7.9Hz), 7.55–7.59(3H, m), 8.02(1H, d). |
| 58 | 7-CN | trans-CH=CH(4-indolyl[2-methyl]) | Found: 479(MR⁻); C₃₁H₃₆NO₄ requires 480. (DMSO+TFA) δ: 0.83–1.25(5H, m), 1.48–1.55(2H, m), 1.63–1.67(2H, m), 1.75–1.80(2H, m), 2.31(3H, s), 2.85–3.20(8H, m), 3.45–3.65(3H, m), 6.36(1H, s), 6.62 (1H, d, J=16Hz), 6.89(1H, t, J=8Hz), 7.00(1H, d, J=7Hz), 7.18(1H, d, J=8 Hz), 7.34(1H, d, J=8Hz), 7.49(1H, d, J=16Hz), 7.55–7.62(2H, m), 7.90(1H, d, J=8Hz), 9.75(1H, b s), 11.09(1H, s). |
| 59 | 7-CN | trans-CH=CH(5-benzimidazolyl) | Found: 466(MH⁻); C₂₉H₃₃N₅O requires 467. (DMSO+TFA) δ: 1.02–1.35(5H, m), 1.57–1.61(2H, m), 1.75–1.78(2H, m), 1.90–1.93(2H, m), 3.00–3.30(8H, m), 3.65–3.70(3H, m), 6.66 and 6.73(1H, 2 x d, J=16Hz), 7.43(1H, d, J=8Hz), 7.60–8.08 (6H, m), 8.00 and 8.06(1H, 2 x s), 9.59 (1H, m), 9.88(1H, b s). |
| 60 | 7-CN | trans-CH=CHC₆H₅ | Found: 428(MH⁺); C₂₈H₃₃N₃O requires 427. (DMSO-d₆+TFA) δ: 0.96–1.36(5H, m), 1.62(2H, m), 1.81(4H, m), 3.05(2H, m), 3.18(6H, m), 3.67(3H, m), 6.60(1H, d, J= |

TABLE 1-continued

[Structure: benzazepine with R¹ substituent, connected via ethyl linker to cyclohexyl group bearing NH-C(=O)-A]

| Example | R¹ | A | Characterising Data Mass Spectrum (API⁺); ¹H NMR (CDCl₃) |
|---------|----|----|----------------------------------------------------------|
| 61 | 7-CN | trans-CH=CHC₆H₃(2,3-methylenedioxy) | 16Hz), 7.27–7.59(7H, m), 7.72(2H, m), 7.99(1H, d, J=8Hz), 9.72(1H, br s). Found: 472(MH⁺); C₂₉H₃₃N₃O₃ requires 471. (DMSO-d₆+TFA) δ: 0.94–1.32(5H, m), 1.61(2H, m), 1.82(4H, m), 3.03(2H, m), 3.18(6H, m), 3.64(3H, m), 6.13(2H, s), 6.71(1H, d, J=16Hz), 6.94(3H, m), 7.32 (1H, d, J=16Hz), 7.46(1H, d, J=8Hz), 7.71(2H, m), 8.09(1H, d, J=8Hz), 9.75 (1H, br s). |
| 62 | 7-CN | trans-CH=CHC₆H₄(3-(1-(2-oxo)pyrrolidinyl)) | Found: 51.1(MH⁺); C₃₂H₃₈N₄O₂ requires 510. (DMSO-d₆) δ: 0.9–1.28(5H, m), 1.35 (2H, m), 1.79(4H, m), 2.07(2H, m), 2.48 (8H, m), 2.91(4H, m), 3.59(1H, m), 3.86 (2H, t, J=7Hz), 6.60(1H, d, J=16Hz), 7.34(4H, m), 7.60(3H, m), 7.89(1H, m), 7.99(1H, d, J=8Hz). |
| 63 | 7-CN | —CH₂(2-indolyl) | Found: 455(MH⁺); C₂₉H₃₄N₄O requires 454. (DMSO-d₆) δ: 0.96(2H, m), 1.15(3H, m), 1.34(2H, m), 1.76(4H, m), 2.42(2H, m), 2.50(4H, m), 2.90(4H, m), 3.45(1H, m), 3.53(2H, s), 6.17(1H, m), 6.94(2H, m), 7.32(2H, m), 7.41(1H, d, J=8Hz), 7.56 (2H, m), 7.87(1H, d, J=8Hz), 10.85(1H, br s). |
| 64 | 7-CN | —CH₂(2-benzothiophenyl) | Found: 472(MH⁺); C₂₉H₃₃N₃SO requires 471. (DMSO) δ: 0.95–1.20(5H, m), 1.31–1.35 (2H, m), 1.71–1.81(4H, m), 2.42(2H, t, J=7.4Hz), 2.50–2.53(4H, m), 2.87–2.93 (4H, m), 3.44–3.48(1H, m), 3.70(2H, s), 7.19(1H, s), 7.27–7.32(3H, m), 7.55–7.58(2H, m), 7.75(1H, d, J=7.4Hz), 7.88 (1H, d, J=7.8Hz), 8.04(1H, m). |
| 65 |  | trans-CH=CH(2-thiophenyl[3-Br]) | Found: 512 & 514 (MH⁺); C₂₆H₃₀N₃SOBr requires 511 & 513. (DMSO) δ: 0.95–1.40(7H, ), 1.72–1.85 (4H, m), 2.42(2H, m), 2.50–2.58(4H, m, under DMSO), 2.87–2.95(4H, m), 3.54–3.62(1H, m), 6.48(1H, d), 7.19(1H, d, J=5.4Hz), 7.32(1H, d), 7.48(1H, d), 7.55–7.60(2H, m), 7.72(1H, d), 8.05(1H, d). |
| 66 | 7-CN | —C₆H₄(3-(2-pyridyl)) | Found: 479(MH⁺); C₃₁H₃₄N₄O requires 478. (DMSO-d₆) δ: 1.04–1.37(2H, m), 1.28–1.47(5H, m), 1.81–1.97(4H, m), 2.49 (2H, t, J=7Hz), 2.56–2.61(4H, m, obscurred by DMSO), 2.92–3.00(4H, m), 3.79–3.88(1H, m), 7.38(1H, d, J=8Hz), 7.44–7.47(1H, m), 7.60–7.66(3H, m), 7.90–8.00(2H, m), 8.06–8.10(1H, m), 8.25–8.27(1H, m), 8.37–8.40(1H, m), 8.55(1H, s), 8.73–8.76(1H, m). |
| 67 | 7-CN | —C₆H₄(3-(5-pyrimidinyl)) | Found: 480(MH⁺); C₃₀H₃₃N₅O requires 479. (DMSO-d₆) & [HCl salt] δ: 1.05–1.12 (2H, m), 1.30–1.41(3H, m), 1.65–1.70 (2H, m), 1.78–1.82(2H, m), 1.88–1.92 (2H, m), 2.96–3.04(2H, m), 3.08–3.20 (4H, m), 3.30–3.45(2H, m), 3.65–3.71 (2H, m), 3.75–3.80(1H, m), 7.45(1H, d, J= 8Hz), 7.60–7.73(2H, m), 7.92–7.98 |

TABLE 1-continued

[Structure: benzazepine with R¹ substituent connected via ethyl linker to cyclohexyl-NH-C(=O)-A]

| Example | R¹ | A | Characterising Data Mass Spectrum (API⁺); ¹H NMR (CDCl₃) |
|---|---|---|---|
| | | | (3H, m), 8.23(1H, s), 8.32–8.36(1H, m), 9.21–9.23(3H, m), 10.67(1H, s). |
| 68 | 7-CN | —C₆H₄(3-C₆H₄(4-CN)) | Found: 503(MH⁺); C₃₃H₃₄N₄O requires 502. (DMSO-d₆) δ: 1.00–1.11(2H, m), 1.20–1.43(5H, m), 1.79–1.83(2H, m), 1.88–1.93(2H, m), 2.48(2H, t, J=7Hz), 2.52–2.58(4H, m, obscurred by DMSO), 2.91–2.96(4H, m), 3.75–8.83(1H, m), 7.34(1H, d, J=8Hz), 7.58–7.61(3H, m), 7.83–7.89(3H, m), 7.95–8.05(3H, m), 8.20(1H, s), 8.33–8.35(1H, m). |
| 69 | 7-CN | —C₆H₄(3-(3-(5-ethyl)-1,2,4-oxadiazolyl) | Found: 498(MH⁺); C₃₀H₃₅N₅O₂ requires 497. δ: 1.07–1.33(5H, m), 1.41–1.50(5H, m), 1.82–1.86(2H, m), 2.09–2.13(2H, m), 2.48–2.54(2H, m), 2.61–2.64(4H, m), 2.90–3.10(6H, m), 3.89–4.04(1H, m), 6.05(1H, d, J=8Hz), 7.18(1H, d, J=8 8Hz), 7.38–7.43(2H, m), 7.57(1H, t, J=8Hz), 7.99(1H, dd, J=8Hz and 1Hz), 8.20(1H, dd, J=8Hz and 1Hz), 8.33(1H, d, J=1Hz). |
| 70 | 7-CN | trans-CH=CH(2-thiophenyl) | Found: 434(MH⁺); C₂₆H₃₁N₃OS requires 433. (DMSOd₆) δ: 0.85–1.30(5H, m), 1.37(2H, m), 1.90(4H, m), 2.45–2.75(6H, m), 3.00(4H, m), 3.58(1H, m), 6.35(1H, d, J=16Hz), 7.10(1H, m), 7.35(2H, m), 7.45–7.65(4H, m), 7.97(1H, d, J=16Hz). |
| 71 | 7-CN | trans-CH=CH(2-furanyl) | Found: 418(MH⁺); C₂₆H₃₁N₃O₂ requires 417. (DMSOd₆) δ: 0.80–1.30(5H, m), 1.37(2H, m), 1.78(4H, m), 2.30–2.70(6H, m), 2.93(4H, m), 3.55(1H, m), 6.38(1H, d, J=16Hz), 6.55(1H, dd, J=3,2Hz), 6.74(1H, d, J=3Hz), 7.19(1H, d, J=16Hz), 7.33(1H, d, J=8Hz), 7.57(2H, m), 7.75(1H, s), 8.00(1H, d, J=8Hz). |
| 72 | 7-CN | trans-CH=CH(3-thiophenyl) | Found: 434(MH⁺); C₂₆H₃₁N₃OS requires 433. (DMSOd₆) δ: 0.85–1.30(5H, m), 1.40(2H, m), 1.80(4H, m), 2.35–2.70(6H, m), 2.90(4H, m), 3.60(1H, m), 6.40(1H, d, J=16Hz), 7.30(2H, m), 7.38(1H, d, J=16Hz), 7.60(3H, m), 7.75(1H, m), 7.90(1H, d, J=8Hz). |
| 73 | 7-CN | trans-CH=CH(3-furanyl) | Found: 418(MH⁺); C₂₆H₃₁N₃O₂ requires 417. (DMSOd₆) δ: 0.85–1.30(5H, m), 1.35(2H, m), 1.80(4H, m), 2.30–2.60(6H, m), 2.85(4H, m), 3.55(1H, m), 6.28(1H, d, J=16Hz), 6.66(1H, s), 7.28(1H, d, J=16Hz), 7.31(1H, d, J=8Hz), 7.55(2H, m), 7.71(1H, s), 7.85(1H, d, J=8Hz), 7.98(1H, s). |
| 74 | 7-CN | trans-CH=CH(4-quinolinyl) | Found: 479(MH⁺); C₃₁H₃₄N₄O requires 478. δ(DMSO+TFA): 1.00–1.30(5H, m), 1.60–1.70(2H, m), 1.75–1.81(2H, m), 1.90–1.95(2H, m), 2.90–3.30(8H, m), 3.60–3.80(2H, m), 7.07(1H, d, J=16Hz), 7.47(1H, d, J=8Hz), 7.71(1H, dd, J=8Hz), 7.75(1H, s) 7.95(1H, m), 8.05–8.30(4H, m), 8.45(1H, d, J=8Hz), 8.53 |

TABLE 1-continued

| Example | R¹ | A | Characterising Data Mass Spectrum (API⁺); ¹H NMR (CDCl₃) |
|---|---|---|---|
| | | | (1d, J=8Hz), 9.25(1H, d, J=5Hz), 9.78(1H, br s). |
| 75 | | trans-CH=CH(5-pyrimidinyl) | Found: 430(MH⁺); $C_{26}H_{31}N_5O$ requires 429.<br>δ: (DMSO+TFA): 1.00–1.30(5H, m), 1.55–1.65(2H, m), 1.75–1.80(2H, m), 1.80–1.90(2H, m), 3.00–3.25(8H, m), 3.60–3.75(3H, m), 6.80(1H, d, J=16Hz), 7.42(1H, d, J=16Hz), 7.46(1H, d, J=8Hz), 7.71(1H, dd, J=8Hz, 2Hz), 7.74 (1H, s), 8.15(1H, d, J=8Hz), 9.00(2H, s), 9.15(1H, s), 9.72(1H, br s). |
| 76 | 7-CN | —CH₂C₆H₃(2,4-diF) | Found: 452(MH⁺); $C_{27}H_{31}F_2N_3O$ requires 451.<br>δ(DMSO+TFA): 0.90–1.10(2H, m), 1.20–1.30(3H, m), 1.50–1.65(2H, m), 1.70–1.85(4H, m), 2.90–3.30(8H, m), 3.40(2H, s), 3.50(1H, m), 3.67(2H, m), 7.00(1H, m), 7.15(1H, m), 7.40(1H, m), 7.45(1H, d, J=8Hz), 7.70(1H, m), 7.73 (1H, s), 7.96(1H, d, J=8Hz), 9.70(1H, br s). |
| 77 | 7-CN | —CH₂(1-naphthyl) | Found: 466(MH⁺); $C_{31}H_{35}N_3O$ requires 465.<br>δ: 0.70–0.80(2H, m), 0.90–1.10(3H, m), 1.30–1.40(2H, m), 1.60–1.70(2H, m), 1.70–1.80(2H, m), 2.40(2H, m), 2.55 (4H, m), 2.80–3.00(4H, m), 3.66(1H, m), 4.00(2H, s), 5.05(1H, d, J=8Hz), 7.15 (1H, d, J=8Hz), 7.34(1H, s), 7.35–7.40 (2H, m), 7.45(1H, m), 7.50(2H, m), 7.83 (1H, d, J=8Hz), 7.86(1H, m), 7.93(1H, m). |
| 78 | 7-COMe | 3-pyrrolo[2,3-b]pyridyl | Found: 459(MH⁺); $C_{28}H_{34}N_4O_2$ requires 458.<br>(DMSOd₆) δ: 1.0–1.20(2H, m), 1.25–1.55(5H, m), 1.75–2.00(4H, m), 2.40–2.65(6H, m), 2.56(3H, s), 2.95(4H, m), 3.75(1H, m), 7.15(1H, m), 7.25(1H, m), 7.74(3H, m), 8.15(1H, s), 8.25(1H, m), 8.45(1H, m), 12.05(1H, br s). |
| 79 | 7-COMe | —CH₂C₆H₄(4-F) | Found: 451(MH⁺); $C_{28}H_{35}FN_2O_2$ requires 450.<br>(DMSOd₆) δ: 0.85–1.20(5H, m), 1.35 (2H, m), 1.85(4H ,m), 2.40–2.65(6H, m), 2.54(3H, s), 2.76(4H, m), 3.35(2H, s), 3.45(1H, m), 7.10(2H, m), 7.25(3H, m), 7.65(2H, m), 7.90(1H, d, J=8Hz). |
| 80 | 7-COMe | —C₆H₄(3-(3-(5-methyl)-1,2,4-oxadiazolyl)) | Found: 501(MH⁺); $C_{30}H_{36}N_4O_3$ requires 500.<br>(DMSOd₆) δ: 0.90–1.45(7H, m), 1.84 (4H, m), 2.40–2.60(6H, m), 2.55(3H, s), 2.70(3H, s), 2.94(4H, m), 3.91(1H, m), 7.26(1H, d, J=8Hz), 7.60–7.75(3H,m), 8.05(1H, m), 8.10(1H, m), 8.45(2H, m). |
| 81 | 7-COMe | trans-CH=CHC₆H₄(4-F) | Found: 463(MH⁺); $C_{29}H_{35}FN_2O_2$ requires 462.<br>δ: (DMSOd₆) δ: 0.95–1.30(5H, m), 1.40 (2H, m), 1.82(4H, m), 2.40–2.65(6H, m), 2.56(3H, s), 2.95(4H, m), 3.62(1H, m), 6.56(1H, d, J=16Hz), 7.25(3H, m), 7.40 (1H, d, J=16Hz), 7.65(2H, m), 7.70(2H, m), 7.95(1H, d, J=8Hz). |

TABLE 1-continued

| Example | R¹ | A | Characterising Data Mass Spectrum (API⁺); ¹H NMR (CDCl₃) |
|---|---|---|---|
| 82 | 7-CN | —CH₂(6-(2-amino)benzo-thiazolyl) | Found: 488(MH⁺); $C_{28}H_{33}N_5OS$ requires 487.<br>δ: 0.85–1.11(5H, m), 1.37(2H, m), 1.68 (2H, m), 1.89(2H, m), 2.45(2H, m), 2.59 (4H, m), 2.92(4H, m), 3.57(2H, s), 3.68 (1H, m), 5.16(3H, m), 7.17(2H, m), 7.38 (2H, m), 7.52(2H, m). |
| 83 | 7-CN | —CH₂(6-(2-methyl)-benzothiazolyl) | Found: 487(MH⁺); $C_{29}H_{34}N_4OS$ requires 486.<br>δ(DMSO-d₆): 0.93(2H, m), 1.15(3H, m), 1.33(2H, m), 1.75(4H, m), 2.42(2H, m), 2.52(4H, m), 2.77(3H, s), 2.90(4H, m), 3.43(3H, m), 7.33(2H, m), 7.56(2H, m), 7.82(2H, m), 7.95(1H, d, J=8Hz). |
| 84 | 7-CN | —CH₂(6-(2,3-dihydro-2-oxo)-indolinyl) | Found: 471(MH⁺); $C_{29}H_{34}N_4O_2$ requires 470.<br>δ (DMSO-d₆+TFA): 0.88–1.32(5H, m), 1.59(2H, m), 1.74(4H, m), 2.90–3.27 (8H, m), 3.29(2H, s), 3.40(2H, s), 3.45 (1H, m), 3.65(2H, m), 6.73(1H, s), 6.79 (1H, d, J=9Hz), 7.08(1H, d, J=9Hz), 7.45(1H, d, J=9Hz), 7.69(1H, d, J= 9Hz), 7.72(1H, s), 7.90(1H, d, J=9Hz), 9.86(1H, br s), 10.33(1H, br s). |
| 85 | 7-CN | —CH₂(5-(2,3-dihydro-2-oxo)-indolinyl) | Found: 471(MH⁺); $C_{29}H_{34}N_4O_2$ requires 470.<br>δ(DMSO-d₆+TFA): 0.90–1.35(5H, m), 1.59(2H, m), 1.75(4H, m), 2.91–3.29 (8H, m), 3.27(2H, s), 3.43(2H, s), 3.47 (1H, m), 3.66(2H, m), 6.72(1H, d, J= 9Hz), 7.01(1H, d, J=9Hz), 7.06(1H, s), 7.45(1H, d, J=9Hz), 7.69(1H, d, J= 9Hz), 7.72(1H, s), 7.88(1H, d, J=9Hz), 9.90(1H, br s), 10.29(1H, br s). |
| 86 | 7-CN | CH=CHC₆H₄(4-CONHMe) | Found: 485(MH⁺); $C_{30}H_{36}N_4O_2$ requires 484.<br>(DMSO+TFA) δ: 0.97–1.28(5H, m), 1.58–1.64(2H, m), 1.76–1.90(4H, m), 2.79(3H, m), 2.99–3.33(8H, m), 3.66–3.77(3H, m), 6.69(1H, d, J=16Hz), 7.41–7.45(2H, m), 7.60–7.73(3H, m), 7.86 (2H, d, J=8Hz), 8.03(1H, d), 8.45(1H, m), 9.75(1H, bs). |
| 87 | 7-CN | CH₂(5-(2-amino)benzoxazolyl | Found: 472(MH⁺); $C_{28}H_{33}N_5O_2$ requires 471.<br>(DMSO+TFA) δ: 0.77–1.23(5H, m), 1.54–1.62(2H, m), 1.70–1.79(4H, m), 2.99–3.24(8H, m), 3.38–3.45(3H, m), 3.60–3.69(2H, m), 6.49(1H, d, J= 10Hz), 7.15(1H, s), 7.32(1H, d, J=8Hz), 7.45(1H, d, J=8Hz), 7.67–7.72(2H, m), 7.93(1H, d), 8.21(2H, b s), 9.92(1H, bs). |
| 88 | 7-CN | —CH₂(6-(1,2-dihydro-2-oxo)quinolinyl) | Found: 483(MH⁺); $C_{30}H_{34}N_4O_2$ requires 482.<br>δ(DMSO+TFA): 0.90–1.20(5H, m), 1.50–1.65(2H, m), 1.70–1.80(4H, m), 2.90–3.30(8H, m), 3.40(2H, s), 3.45(1H, m), 3.60–3.70(2H, m), 6.48(1H, d, J=10 Hz), 7.22(1H, d, J=8Hz), 7.50(1H, dd, J= 10Hz, 2Hz), 7.60–7.50(2H, m), 7.80 (1H, dd, J=10Hz, 2Hz), 7.70(1H, s), 7.86(1H, d, J=9Hz), 7.95(1H, d, J= 8Hz), 9.80(1H, br s), 11.70(1H, br s). |

TABLE 1-continued

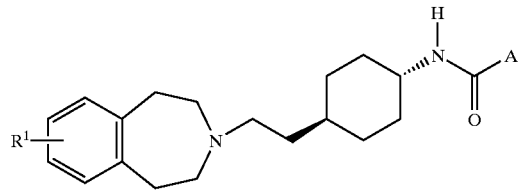

| Example | R¹ | A | Characterising Data Mass Spectrum (API⁺); ¹H NMR (CDCl₃) |
|---|---|---|---|
| 89 | 7-CN | —CH₂(7-(1,2-dihydro-2-oxo)quinolinyl) | Found: 483(MH⁺); $C_{30}H_{34}N_4O_2$ requires 482. δ(DMSO): 0:90–1.00(2H, ,m), 1.10–1.20(5H, m), 1.25–1.40(2H, m), 1.70–1.80(4H, m), 2.40–2.50(4H, m), 2.80–2.90(4H, m), 3.30–3.45(3H, m), 6.43 (1H, d, J=8Hz), 7.05(1H, d, J=8Hz), 7.17(1H, s), 7.32(1H, d, J=8Hz), 7.50–7.60(3H, m), 7.84(1H, d, J=9Hz), 7.97 (1H, d, J=8Hz), 11.70(1H, s). |
| 90 | 7-COMe | trans-CH=CHC₆H₄(3-OMe) | Found: 475(MH⁺); $C_{30}H_{38}N_2O_3$ requires 474. δ: 1.05–1.40(5H, m), 1.44(2H, m), 1.81 (2H, m), 2.05(2H, m), 2.48(2H, m), 2.58 (3H, s), 2.62(4H, m), 2.98(4H, m), 3.82 (3H, s), 3.85(1H, m), 5.43(1H, d, J= 8Hz), 6.33(1H, d, J=16Hz), 6.89(1H, dd, J=2, 8Hz), 7.00(1H, m), 7.08(1H, d, J= 8Hz), 7.17(1H, d, J=8Hz), 7.29(1H, m), 7.56(1H, d, J=16Hz), 7.70(1H, s), 7.73 (1H, m). |
| 91 | 7-COMe | trans-CH=CHC₆H₄(2-CN) | Found: 470(MH⁺); $C_{30}H_{35}N_3O_2$ requires 469. δ: 1.05–1.35(5H, ), 1.43(2H, m), 1.81 (2H, m), 2.06(2H, m), 2.49(2H, m), 2.58 (3H, s), 2.63(4H, m), 2.98(4H, m), 3.86 (1H, m), 5.62(1H, d, J=8Hz), 6.66(1H, d, J=16Hz), 7.17(1H, d, J=8Hz), 7.43 (1H, m), 7.60(2H, m), 7.70(3H, m), 7.77 (1H, d, J=16Hz). |
| 92 | 7-COMe | trans-CH=CH(3-thiophenyl) | Found: 451(MH⁺); $C_{27}H_{34}N_2O_2S$ requires 450. δ: 1.05–1.35(5H, m), 1.42(2H, m), 1.80 (2H, m), 2.05(2H, m), 2.49(2H, m), 2.58 (3H, s), 2.62(4H, m), 2.98(4H, m), 3.85 (1H, m), 5.41(1H, d, J=8Hz), 6.18(1H, d, J=16Hz), 7.15(1H, d, J=8Hz), 7.25 (2H, m), 7.42(1H, m), 7.59(1H, d, J= 16Hz), 7.69(1H, s), 7.72(1H, m). |
| 93 | 7-COMe | trans-CH=CH(8-(1,2-dihydro-2-oxo)-quinolinyl) | Found: 512(MH⁺); $C_{32}H_{37}N_3O_3$ requires 511. DMSOd₆, HCl salt) δ: 1.00–1.40(5H, m), 1.60–1.95(6H, m), 2.56(3H, s), 2.90–3.20(6H, m), 3.40(2H, m), 3.65(3H, m), 6.55(2H, m), 7.22(1H, t, J=8Hz), 7.37 (1H, d, J=8Hz), 7.70(2H, m), 7.80(2H, m), 7.90–8.10(3H, m), 10.59(1H, br s), 11.35(1H, br s). |
| 94 | 7-CN | —C₆H₄(3-(1-pyrazolyl)) | Found: 468(MH⁺); $C_{29}H_{33}N_5O$ requires 467. δ: 1.06–1.40(5H, m), 1.40–1.50(2H, m), 1.81–1.86(2H, m), 2.08–2.13(2H, m), 2.38–2.54(2H, m), 2.61–2.65(4H, m), 2.90–3.00(4H, m), 3.89 3.96(1H, m), 6.06(1H, d, J=8Hz), 6.50(1H, t, J= 2Hz), 7.18(1H, d, J=8Hz), 7.29–7.43 (2H, m), 7.51(1H, t, J =8Hz), 7.68(1H, d, J=8Hz), 7.75(1H, d, J=1.5Hz), 7.79–7.83(1H, m), 8.00(1H, m), 8.08(1H, m). |
| 95 | 7-CN | —CH₂(2-thiophenyl) | Found: 422 (MH⁺); $C_{25}H_{31}N_3OS$ requires 421 δ: 0.90–1.20(5H, m), 1.35–1.46(2H, m), 1.69–1.72(2H, m), 1.80–2.00(2H, m), 2.42–2.48(2H, m), 2.57–2.65(4H, m), 2.90–2.96(4H, m), 3.65–3.75(1H, m), |

TABLE 1-continued

| Example | R¹ | A | Characterising Data Mass Spectrum (API⁺); ¹H NMR (CDCl₃) |
|---|---|---|---|
| | | | 3.74(2H, s), 5.38(1H, d, J=8Hz), 8.92 (1H, m), 6.98(1H, m), 7.16(1H, d, J= 8Hz), 7.23–7.26(1H, m), 7.36–7.42(2H, m). |
| 96 | 7-CN | —CH₂(3-benzothiophenyl) | Found: 472(MH⁺); C₂₉H₃₃N₃OS requires 471. δ: 0.80–1.20(5H, m), 1.30–1.40(2H, m), 1.60–1.75(2H, m), 1.80–1.90(2H, m), 2.40–2.50(2H, m), 2.50–2.70(4H, m), 2.85–2.95(4H, m), 3.65–3.75(1H, m), 3.80(2H, s), 5.23(1H, d, J=8Hz), 7.16 (1H, d, J=8Hz), 7.30–7.45(5H, m), 7.60–7.70(1H, m), 7.85–7.92(1H, m). |
| 97 | 7-CN | —C₆H₄(3-(2-(5-methyl)-1,3,4-oxadiazolyl) | Found: 484(MH⁺); C₂₉H₃₃N₅O₂ requires 483. δ: 1.10–1.40(5H, m), 1.41–1.50(2H, m), 1.82–1.87(2H, m), 2.10–2.14(2H, m), 2.48–2.54(2H, m), 2.62–2.65(7H, m), 2.93–3.00(4H, m), 3.93–3.97(1H, m), 6.04(1H, d, J=8Hz), 7.18(1H, d, J= 8Hz), 7.35–7.43(2H, m), 7.59(1H, t, J= 8Hz), 7.97(1H, dd, J=6 and 1Hz), 8.11 (1H, dd, J=8 and 1Hz), 8.36(1H, d, J= 1Hz). |
| 98 | 7-CN | trans-CH=CH(2-naphthyl) | Found: 478(MH⁺); C₃₂H₃₅N₃O requires 477. δ(DMSO+TFA): 1.00–1.65(5H, m), 1.63(2H, m), 1.76–1.91(4H, m), 2.97–3.32(8H, m), 3.66–3.93(3H, m), 6.75 (1H, d, J=16Hz), 7.47(1H, d), 7.54–7.62 (3H, m), 7.65–7.80(3H, m), 7.85–7.95 (3H, m), 8.00–8.10(2H, m), 9.77(1H, b s). |
| 99 | 7-COMe | CH₂(3-benzothiophenyl) | Found: 489(MH⁺); C₃₀H₃₆N₂O₂S requires 488. δ: 0.80–1.25(5H, m), 1.37(2H, m),1.70 (2H, m), 1.85(2H, m), 2.41(2H, m), 2.57 (3H, s), 2.59(4H, m), 2.94(4H, m), 3.67 (1H, m), 3.80(2H, s), 5.23(1H, d, J= 8Hz), 7.16(1H, d, J=8Hz), 7.32(1H, s), 7.40(2H, m), 7.67(1H, s), 7.70(2H, m), 7.88(1H, m). |
| 100 | 7-COMe | trans-CH=CC₆H₄(4-NHCOMe) | Found: 502(MH⁺); C₃₁H₃₉N₃O₃ requires 501. δ: 0.90–1.35(5H, m), 1.39(2H, m), 1.80 (4H, m), 2.05(3H, s), 2.50–2.80(6H, m), 2.54(3H, s), 2.94(4H, m), 3.60(1H, m), 6.47(1H, d, J=16Hz), 7.20–7.40(2H, m), 7.46(2H, d, J=9Hz), 7.61(2H, d, J= 9Hz), 7.71(2H, m), 7.91(1H, d, J=8Hz), 10.09(1H, s). |
| 101 | 7-COMe | —CH₂(6-(2-amino)-benzothiazolyl) | Found: 505(MH⁺); C₂₉H₃₆N₄O₂S requires 504. δ(DMSOd₆): 0.85–1.30(5H, m), 1.48 (2H, m), 1.75(4H, m), 2.55(3H, s), 2.70–3.25(10H, m), 3.34(2H, s, obscurred by H₂O), 3.55(1H, m), 7.05(1H, m), 7.15–7.35(2H, m), 7.39(2H, br s), 7.47(1H, m), 7.75(2H, m), 7.90(1H, d, J=8Hz). |
| 102 | 7-COMe | 8-(1,4-dihydro-4-oxo)-quinolinyl | Found: 486(MH⁺); C₃₀H₃₅N₃O₃ required 485. δ(DMSOd₆): 0.95–1.20(2H, m), 1.20–1.70(5H, m), 1.70–2.00(4H, m), 2.56 (3H, s), 2.65–3.20(10H, m), 3.82(1H, m), 6.08(1H, d, J=7Hz), 7.25–7.45(2H, m), |

TABLE 1-continued

| Example | R¹ | A | Characterising Data Mass Spectrum (API⁺); ¹H NMR (CDCl₃) |
|---|---|---|---|
| | | | 7.77(2H, m), 7.93(1H, m), 8.10(1H, m), 8.26(1H, d, J=8Hz), 8.71(1H, d, J=8Hz), 12.05(1H, m). |
| 103 | 7-COMe | trans-CH=CHC₆H₄(2-COMe) | Found: 487(MH⁺); C₃₁H₃₈N₂O₃ requires 486. δ: 1.05–1.40(5H, m), 1.44(2H, m), 1.80(2H, m), 2.05(2H, m), 2.50(2H, m), 2.58(3H, s), 2.60(3H, s), 2.64(4H, m), 2.98(4H, m), 3.85(1H, m), 5.50(1H, d, J=8Hz), 6.20(1H, d, J=16Hz), 7.18(1H, d, J=8Hz), 7.35–7.65(3H, m), 7.69(3H, m), 7.91(1H, d, J=16Hz). |
| 104 | 7-COMe | —CH₂(2-benzothiophenyl) | Found: 489(MH⁺); C₃₀H₃₆N₂O₂S requires 488. δ: 1.00–1.30(5H, m), 1.40(2H, m), 1.72(2H, m), 1.94(2H, m), 2.44(2H, m), 2.57(3H, s), 2.61(4H, m), 2.95(4H, m), 3.73(1H, m), 3.82(2H, s), 5.47(1H, d, J=8Hz), 7.16(2H, m), 7.30–7.39(2H, m), 7.65–7.81(4H, m). |
| 105 | 7-CN | trans-CH=CH(5-(3-acetyl)indolyl) | Found: 509(MH⁺); C₃₂H₃₆N₄O₂ requires 508. δ(DMSOd₆): 0.85–1.28(5H, m), 1.35(2H, m), 1.65–1.95(4H, m), 2.35–2.65(6H, m), 2.46(3H, s), 2.91(4H, m), 3.59(1H, m), 6.60(1H, d, J=16Hz), 7.30–7.65(6H, m), 7.96(1H, d, J=8Hz), 8.37(2H, m), 12.05(1H, br s). |
| 106 | 7-CN | —C₆H₄(5-(3-methyl)-1,2,4-oxadiazolyl) | Found: 484(MH⁺); C₂₉H₃₃N₅O₂ requires 483. δ(CDCl₃): 1.13–1.28(5H, m), 1.43–1.48(2H, m), 1.83–1.86(2H, m), 2.10–2.13(2H, m), 2.49(3H, s), 2.51(2H, m), 2.62–2.64(4H, m), 2.88–2.98(4H, m), 3.94–3.98(1H, m), 6.02(1H, d, J=8Hz), 7.18(1H, d, J=7.7Hz), 7.38(1H, s), 7.39(1H, d, H=7.7Hz), 7.64(1H, t, J=7.8Hz), 8.05(1H, d), 8.21(1H, d), 8.39(1H, br s). |
| 107 | 7-CN | —CH₂(5-(2-methyl)-benzimidazolyl) | Found: 470(MH⁺); C₂₉H₃₅N₅O requires 469. δ: 0.87–1.09(5H, m), 1.14(1H, br s), 1.37(2H, m), 1.70(2H, m), 1.88(2H, m), 2.45(2H, m), 2.56(3H, s), 2.60(4H, m), 2.93(4H, m), 3.61(2H, s), 3.69(1H, m), 3.61(2H, s), 3.69(1H, m), 5.44(1H, d, J=7Hz), 7.04(1H, dd, J=8, 2Hz), 7.15(1H, d, J=8Hz), 7.30–7.47(4H, m). |
| 108 | 7-CN | —CH₂(6-quinoxalinyl) | Found: 468(MH⁺); C₂₉H₃₃N₅O requires 467. δ: 0.90–1.15(5H, m), 1.40(2H, m), 1.73(2H, m), 1.93(2H, m), 2.45(2H, m), 2.59(4H, m), 2.94(4H, m), 3.67(1H, m), 3.76(2H, s), 5.33(1H, d, J=7Hz), 7.16(1H, d, J=8Hz), 7.31–7.44(2H, m), 7.72(1H, dd, J=9, 2Hz), 7.96(1H, d, J=2Hz), 8.08(1H, d, J=9Hz), 8.85(2H, s). |
| 109 | 7-CN | trans-CH=CH(3-(2-acetyl)furanyl) | Found: 460(MH⁺); C₂₈H₃₃N₃O₃ requires 459. δ: 1.05–1.35(5H, m), 1.45(2H, m), 1.80(2H, m), 2.04(2H, m), 2.48(2H, m), 2.53(3H, s), 2.61(4H, m), 2.95(4H, m), 3.84(1H, m), 5.56(1H, d, J=8Hz), 6.43(1H, d, J=16Hz), 6.70(1H, d, J=2Hz), 7.17 |

TABLE 1-continued

| Example | R¹ | A | Characterising Data Mass Spectrum (API⁺); ¹H NMR (CDCl₃) |
|---|---|---|---|
| | | | (1H, d, J=8Hz), 7.38(1H, s), 7.41(1H, d, J=8Hz), 7.45(1H, d, J=2Hz), 7.95(1H, d, J=16Hz). |
| 110 | 7-CN | —CH₂(6-(2-amino) benzoxazolyl) | Found: 472(MH⁺); C₂₈H₃₃N₅O₂ requires 471. δ: 0.81–1.12(5H, m), 1.40(2H, m), 1.72 (2H, m), 1.89(2H, m), 2.45(2H, m), 2.93 (4H, m), 3.58(2H, s), 3.69(1H, m), 4.92 (2H, br s), 5.13(1H, m), 7.05(1H, m), 7.17 (2H, m), 7.36(3H, m). |
| 111 | 7-CN | —CH₂(6-(3,4-dihydro-2-oxo)-2H-benzoxazinyl) | Found: 487(MH⁺); C₂₉H₃₄N₄O₃ requires 486. δ(DMSO-d₆): 0.83–1.24(5H, m), 1.32 (2H, m), 1.73(4H, m), 2.47(6H, m), 2.90 (4H, m), 3.25(2H, s), 3.40(1H, m), 4.53 (2H, s), 6.80(3H, m), 7.31(1H, d, J= 8Hz), 7.56(2H, m), 7.84(1H, d, J=8Hz), 10.62(1H, br s). |
| 112 | 7-CN | trans-CH=CHC₆H₃(2-F, 5-NHCOMe) | Found: 503(MH⁺); C₃₀H₃₅FN₄O₂ requires 502. δ(DMSO-d₆+TFA): 0.94–1.34(5H, m), 1.61(2H, m), 1.76(2H, m), 1.87(2H, m), 2.05(3H, s), 2.93–3.33(8H, m), 3.54–3.77(3H, m), 6.65(1H, d, J=15Hz), 7.20 (1H, t, J=9Hz), 7.43(3H, m), 7.69(1H, d, J=9Hz), 7.73(1H, s), 8.03(1H, m), 8.19 (1H, d, J=9Hz), 9.88(1H, br s), 10.09 (1H, br s). |

TABLE 2

| Example No. | R | Mass spectrum, ¹H NMR |
|---|---|---|
| 113 | —CH₂—(2-benzothiophenyl) | Mass spectrum(API⁺): Found 529(MH⁺). C₃₁H₃₆N₄O₂S requires 528. NMR(CDCl₃)δ: 1.00–1.10(4H, m), 1.19(1H, m), 1.35–1.45(2H, m), 1.75(2H, m), 1.95(2H, m), 2.40–2.50(5H, m), 2.61(4H, m), 2.97(4H, m), 3.73(1H, m), 3.82(2H, s), 5.46(1H, d, J=8Hz), 7.16(1H, s), 7.22(1H, d, J=8Hz), 7.25–7.42(2H, m), 7.73(1H, d, J=8Hz), 7.79(1H, d, J=8Hz), 7.81–7.88(2H, m). |
| 114 | (E)-CH=CH-(3-thienyl) | Mass spectrum(API⁺): Found 491(MH⁺). C₂₈H₃₄N₄O₂S requires 490. NMR(CDCl₃)δ: 1.04–1.15(4H, m), 1.25(1H, m), 1.44(2H, m), 1.76(2H, m), 2.05(2H, m), 2.46(3H, s), 2.50(2H, m), 2.64(4H, m), 3.00(4H, m), 3.85(1H, m), 5.36(1H, d, J=8Hz), 6.18(1H, d, J=16Hz), |

TABLE 2-continued

| Example No. | R | Mass spectrum, ¹H NMR |
|---|---|---|
| | | 7.22–7.20(2H, m), 7.30(1H, m), 7.43(1H, m), 7.59(1H, d, J=16Hz), 7.80–7.90(2H, m). |
| 115 | 5-quinolyl | Mass spectrum(API$^+$): Found 510(MH$^+$). $C_{31}H_{35}N_5O_2$ requires 509. NMR(CDCl$_3$)δ: 1.15–1.27(5H, m), 1.45(2H, m), 1.85(2H, m), 2.20(2H, m), 2.46(3H, s), 2.55(2H, m), 2.70(4H, m), 3.00(4H, m), 4.00(1H, m), 5.85(1H, d, J=8Hz), 7.25(1H, d, J=8Hz), 7.46(1H, dd, J=4, 8Hz), 7.60–7.72(2H, m), 7.84–7.87(2H, m), 8.16(1H, d, J=8Hz), 8.72(1H, d, J=8Hz), 8.92(1H, m). |
| 116 | 3-pyrrolo[2,3-b]pyridyl | Mass spectrum(API$^+$): Found 499(MH$^+$). $C_{29}H_{34}N_6O_2$ requires 498. NMR(DMSO-d$_6$)δ: 0.90–1.10(2H, m), 1.10–1.40(5H, m), 1.70–1.90(4H, m), 2.40–2.70(6H, m), 2.96(3H, s), 3.31(4H, m), 3.89(1H, m), 7.15(1H, m), 7.36(1H, d, J=8Hz), 7.71(1H, d, J=8Hz), 7.75–7.85(2H, m), 8.12(1H, s), 8.20(1H, s), 8.35(1H, d, J=8Hz), 12.02(1H, br s). |
| 117 | 3-(3-(5-methyl)-1,2,4-oxadiazolyl)phenyl | Mass spectrum(API$^+$): Found 541(MH$^+$). $C_{31}H_{36}N_6O_3$ requires 540. NMR(CDCl$_3$)δ 1.10–1.22(4H, m), 1.27(1H, m), 1.55(2H, m), 1.90(2H, m), 2.10(2H, m), 2.47(3H, s), 3.65(2H, m), 2.68(3H, s), 2.76(4H, m), 3.06(4H, m), 3.95(1H, m), 6.00(1H, d, J=8Hz), 7.25(1H, d, J=8Hz), 7.57(1H, t, J=8Hz), 7.80–7.90(2H, m), 8.02(1H, d, J=8Hz), 8.15(1H, d, J=8Hz), 8.32(1H, s). |
| 118 | 8-(1,4-dihydro-4-oxo)quinolyl | Mass spectrum(API$^+$): Found 526(MH$^+$). $C_{31}H_{35}N_5O_3$ requires 525. NMR(DMSO-d$_6$)δ: 0.90–1.10(2H, m), 1.20–1.40(5H, m), 1.80–2.00(4H, m), 2.30–2.75(9H, m), 2.96(4H, m), 3.80(1H, m), 6.09(1H, d, J=8Hz), 7.30–7.40(2H, m), 7.75–7.88(2H, m), 7.92(1H, m), 8.05(1H, d, J=8Hz), 8.22(1H, d, J=8Hz), 8.65(1H, d, J=8Hz), 12.04(1H, br s). |
| 119 | (E)-CH=CH-(4-fluoro)phenyl | Mass spectrum(API$^+$): Found 503(MH$^+$). $C_{30}H_{35}FN_4O_2$ requires 502. NMR(CDCl$_3$)δ: 1.10–1.30(5H, m), 1.40–1.47(2H, m), 1.78–1.82(2H, m), 2.00–2.10(2H, m), 2.46(3H, s), 2.47–2.52(2H, m), 2.60–2.70(4H, m), 2.95–3.05(4H, m), 3.86(1H, m), 5.38(1H, d, J=8Hz), 6.26(1H, d, J=16Hz), 7.05(2H, t, J=8Hz), 7.24(1H, d, J=8Hz), 7.47(2H, dd, J=5, 8Hz), 7.57(1H, d, J=16Hz), 7.80–7.90(2H, m). |
| 120 | (E)-CH=CH-(3-fluoro)phenyl | Mass spectrum(API$^+$): Found 503(MH$^+$). $C_{30}H_{35}FN_4O_2$ requires 502. NMR(CDCl$_3$)δ: 1.10–1.30(5H, m), 1.42(2H, m), 1.81(2H, m), 2.06(2H, m), 2.46(3H, s), 2.51(2H, m), 2.65(4H, m), 3.00(4H, m), 3.87(1H, m), 5.41(1H, d, J=8Hz), 6.33(1H, d, J=16Hz), 7.02(1H, m), 7.15(1H, m), 7.25(2H, m), 7.31(1H, m), 7.57(1H, d, J=16Hz), 7.80–7.90(2H, m). |
| 121 | (E)-CH=CH-(3-acetamido-2-fluoro)phenyl | Mass spectrum(API$^+$): Found 560(MH$^+$). $C_{32}H_{38}FN_5O_3$ requires 559. NMR(CDCl$_3$)δ: 1.10–1.20(4H, m), 1.20–1.30(1H, m), 1.40–1.50(2H, m), 1.77–1.83(2H, m), 2.05–2.12(2H, m), 2.24(3H, s), |

TABLE 2-continued

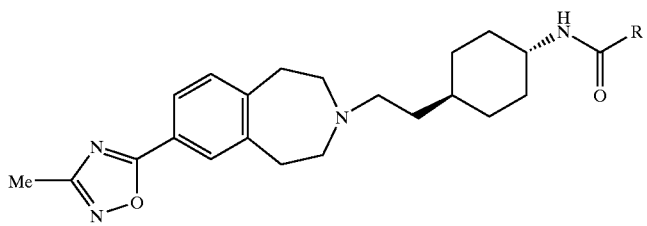

| Example No. | R | Mass spectrum, ¹H NMR |
|---|---|---|
| | | 2.46(3H, s), 2.55(2H, m), 2.65(4H, m), 3.00(4H, m), 3.85(1H, m), 5.42(1H, d, J=8Hz), 6.42(1H, d, J=16Hz), 7.12(1H, t, J=8 Hz), 7.18–7.30(2H, m), 7.38(1H, s), 7.71(1H, d, J=16Hz), 7.80–7.90(2H, m), 8.30(1H, m). |
| 122 | (E)-CH=CH-(3-acetyl)phenyl | Mass spectrum(API⁺): Found 527(MH⁺). $C_{32}H_{38}N_4O_3$ requires 526. NMR(CDCl₃)δ: 1.10–1.20(4H, m), 1.20–1.30(1H, m), 1.50(2H, m), 1.80(2H, m), 2.05(2H, m), 2.46(3H, s), 2.56(2H, m), 2.60(3H, s), 2.65(4H, m), 3.00(4H, m), 3.85(1H, m), 5.48(1H, d, J=8Hz), 6.20(1H, d, J=16Hz), 7.24(1H, d, J=8Hz), 7.40(1H, m), 7.45–7.55(2H, m), 7.70(1H, d, J=8 Hz), 7.85–7.88(2H, m), 7.91(1H, d, J=16 Hz). |
| 123 | —CH₂-(3-fluoro)phenyl | Mass spectrum(API⁺): Found 491(MH⁺). $C_{29}H_{35}FN_4O_2$ requires 490. NMR(CDCl₃)δ: 1.00–1.12(4H, m), 1.19(1H, m), 1.40(2H, m), 1.75(2H, m), 1.93(2H, m), 2.40–2.50(5H, m), 2.62(4H, m), 2.95(4H, m), 3.52(2H, s), 3.70(1H, m), 5.14(1H, d, J=8Hz), 6.90–7.05(3H, m), 7.22(1H, d, J=8Hz), 7.30(1H, m), 7.80–7.90(2H, m). |
| 124 | —CH₂-(2,4-difluoro)phenyl | Mass spectrum(API⁺): Found 509(MH⁺). $C_{29}H_{34}F_2N_4O_2$ requires 508. NMR(CDCl₃)δ:. 1.00–1.10(4H, m), 1.15–1.25(1H, m), 1.35–1.45(2H, m), 1.70–1.80(2H, m), 1.90–2.00(2H, m), 2.46(3H, s), 2.48(2H, m), 2.63(4H, m), 2.97(4H, m), 3.48(2H, s), 3.70(1H, m), 5.24(1H, d, J=8 Hz), 6.85(2H, m), 7.23(1H, d, J=8Hz), 7.24–7.35(1H, m), 7.80–7.90(2H, m). |
| 125 | 2-naphthyl | Mass spectrum(API⁺): Found 509(MH⁺). $C_{32}H_{36}N_4O_2$ requires 508. NMR(CDCl₃)δ: 1.10–1.35(5H, m), 1.40–1.50(2H, m), 1.80–1.90(2H, m), 2.10–2.20(2H, m), 2.46(3H, s), 2.55(2H, m), 2.67(4H, m), 3.01(4H, m), 4.00(1H, m), 6.04(1H, d, J=8Hz), 7.24(1H, d, J=8Hz), 7.55(2H, m), 7.80–7.95(6H, m), 8.25(1H, s). |
| 126 | 7-(3,4-dihydro-3-oxo)-2H-benzoxazinyl | Mass spectrum(API⁺): Found 530(MH⁺). $C_{30}H_{35}N_5O_4$ requires 529. NMR(CDCl₃)δ: 1.10–1.30(5H, m), 1.40–1.50(2H, m), 1.75–1.85(2H, m), 2.00–2.10(2H, m), 2.46(3H, s), 2.50–2.60(2H, m), 2.64–2.75(4H, m), 2.95–3.05(4H, m), 3.90(1H, m), 4.64(2H, s), 5.79(1H, d, J=8Hz), 6.81(1H, d, J=8Hz), 7.20–7.22(1H, m), 7.40(2H, m), 7.72(1H, br s), 7.83–7.90(2H, m). |
| 127 | 5-quinolinyl(2-Me) | Mass spectrum(API⁺): Found 524(MH⁺). $C_{32}H_{37}N_5O_2$ requires 523. NMR(DMSO-d₆)δ: 1.02–1.10(2H, m), 1.20–1.40(5H, m), 1.75–1.83(2H, m), 1.90–2.00(2H, m), 2.33(2H, m), 2.40(3H, s), 2.55–2.60(4H, m), 2.66(3H, s), 2.90–3.00(4H, m), 3.75–3.85(1H, s), 7.35–7.37(1H, m), 7.44–7.47(1H, m), 7.57–7.59(1H, m), 7.69–7.72(1H, m), 7.81–7.85(2H, m), 7.96–8.00(1H, m), 8.41–8.48(2H, m). |

TABLE 2-continued

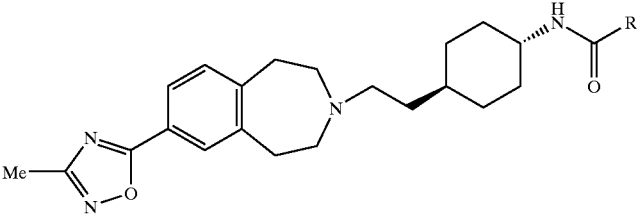

| Example No. | R | Mass spectrum, ¹H NMR |
|---|---|---|
| 128 | —CH₂-(2-fluoro)phenyl | Mass spectrum(API⁺): Found 491(MH⁺). $C_{29}H_{35}FN_4O_2$ requires 490. NMR(CDCl₃)δ: 1.00–1.07(4H, m), 1.18–1.23(1H, m), 1.38–1.43(2H, m), 1.72–1.76(2H, m), 1.91–1.94(2H, m), 2.46(3H, s), 2.45–2.49(2H, m), 2.60–2.64(4H, m), 2.95–2.99(4H, m), 3.54(2H, s), 3.67–3.72(1H, m), 5.25(1H, d, J=8Hz), 7.04–7.14(2H, m), 7.21–7.32(3H, m), 7.84–7.86(2H, m). |
| 129 | —CH₂-(2,5-difluoro)phenyl | Mass spectrum(API⁺): Found 509(MH⁺). $C_{29}H_{34}F_2N_4O_2$ requires 508. NMR(CDCl₃)δ: 0.96–1.29(5H, m), 1.37–1.46(2H, m), 1.67–1.79(2H, m), 1.93–1.97(2H, m), 2.46(3H, s), 2.44–2.50(2H, m), 2.60–2.65(4H, m), 2.95–3.05(4H, m), 3.50(2H, s), 3.62–3.76(1H, m), 5.30(1H, d, J=8Hz), 6.89–7.08(2H, m), 7.21–7.24(2H, m), 7.84–7.87(2H, m). |
| 130 | 2-indolyl | Mass spectrum(API⁺): Found 498(MH⁺). $C_{30}H_{35}N_5O_2$ requires 497. NMR(DMSO-d₆)δ: 0.97–1.11(2H, m), 1.26–1.50(5H, m), 1.70–2.00(4H, m), 2.39–2.62(5H, m), 2.93–3.02(4H, m), 3.31–3.40(4H, m), 3.70–3.90(1H, m), 6.98–7.04(1H, m), 7.13–7.18(2H, m), 7.35–7.43(2H, m), 7.59(1H, d, J=8Hz), 7.81–7.85(2H, m), 8.20(1H, d, J=8Hz), 11.50–11.54(1H,s). |

TABLE 3

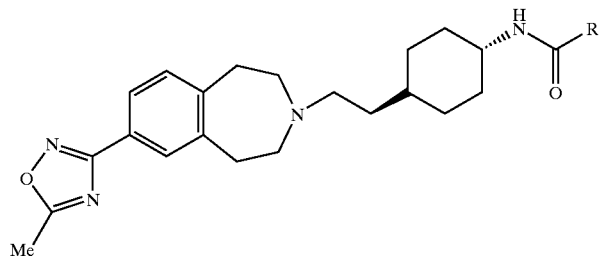

| Example No. | R | Mass spectrum, ¹H NMR |
|---|---|---|
| 131 | —CH₂-(2-benzothiophenyl) | Mass spectrum(API⁺): Found 529(MH⁺). $C_{31}H_{36}N_4O_2S$ requires 528. NMR(CDCl₃)δ: 0.95–1.10(4H, m), 1.18(1H, m), 1.35–1.45(2H, m), 1.74(2H, m), 1.95(2H, m), 2.45(2H, m), 2.55–2.68(4H, m), 2.64(3H, s), 2.90–3.00(4H, m), 3.73(1H, m), 3.82(2H, s), 5.46(1H, d, J=8Hz), 7.16(1H, s), 7.18(1H, d, J=8Hz), 7.27–7.40(2H, m), 7.72(1H, d, J=7Hz), 7.76–7.85(3H, m). |
| 132 | (E)-CH=CH-(3-thienyl) | Mass spectrum(API⁺): Found 491(MH⁺). $C_{28}H_{34}N_4O_2S$ requires 490. NMR(CDCl₃)δ: 1.05–1.20(4H, m), 1.24(1H, m), 1.44(2H, m), 1.80(2H, m), 2.05(2H, m), 2.50(2H, m), 2.55–2.70(7H, m), 2.90–3.05(4H, m), 3.85(1H, m), 5.35(1H, |

TABLE 3-continued

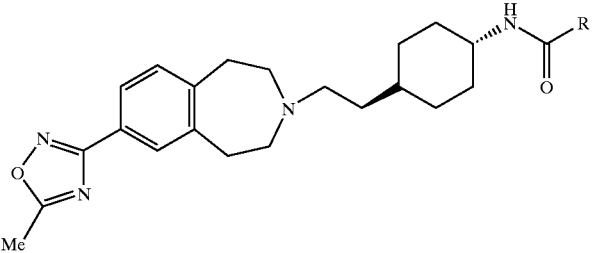

| Example No. | R | Mass spectrum, $^1$H NMR |
|---|---|---|
|  |  | d, J=8Hz), 6.18(1H, d, J=16Hz), 7.19(1H, d, J=8Hz), 7.21–7.27(1H, m), 7.32(1H, m), 7.43(1H, m), 7.59(1H, d, J=16 Hz), 7.75–7.85(2H, m). |
| 133 | 5-quinolinyl | Mass spectrum(API$^+$): Found 510(MH$^+$). $C_{31}H_{35}N_5O_2$ requires 509. NMR(CDCl$_3$)δ: 1.10–1.35(5H, m), 1.48(2H, m), 1.80–1.90(2H, m), 2.10–2.25(2H, m), 2.53(2H, m), 2.65(3H, s), 2.60–2.70(4H, m), 2.99(4H, m), 4.03(1H, m), 5.85(1H, d, J=8Hz), 7.20(1H, d, J=8Hz), 7.46(1H, dd, J=4, 8Hz), 7.66(2H, m), 7.78–7.85(2H, m), 8.16(1H, d, J=8Hz), 8.74(1H, d, J=8Hz), 8.95(1H, m). |
| 134 | 3-pyrrolo[2,3-b]pyridyl | Mass spectrum(API$^+$): Found 499(MH$^+$). $C_{29}H_{34}N_6O_2$ requires 498. NMR(DMSO-d$_6$)δ: 0.90–1.10(2H, m), 1.20–1.50(5H, m), 1.70–1.90(4H, m), 2.40–2.60(6H, m), 2.65(3H, s), 2.93(4H, m), 3.75(1H, m), 7.14(1H, dd, J=4, 8Hz), 7.29(1H, d, J=8Hz), 7.60–7.80(3H, m), 8.14(1H, s), 8.23(1H, m), 8.43(1H, m), 11.99(1H, s). |
| 135 | 8-(1,4-dihydro-4-oxo)quinolyl | Mass spectrum(API$^+$): Found 526(MH$^+$). $C_{31}H_{35}N_5O_3$ requires 525. NMR(CDCl$_3$)δ: 1.10–1.20(2H, m), 1.20–1.34(3H, m), 1.42–1.50(2H, m), 1.80–1.90(2H, m), 2.05–2.15(2H, m), 2.50(2H, m), 2.65(3H, s), 2.65–2.70(4H, m), 2.98(4H, m), 3.95(1H, m), 6.30(1H, d, J=8Hz), 6.33(1H, dd, J=2, 8Hz), 7.20(1H, d, J=8Hz), 7.31(1H, t, J=8Hz), 7.67(1H, t, J=8Hz), 7.81(3H, m), 8.55(1H, d, J=8Hz), 12.20(1H, br s). |
| 136 | 3-(3-(5-methyl)-1,2,4-oxadiazolyl)phenyl | Mass spectrum(API$^+$): Found 541(MH$^+$). $C_{31}H_{36}N_6O_3$ requires 540. NMR(CDCl$_3$)δ: 1.10–1.30(5H, m), 1.40(2H, m), 1.83(2H, m), 2.10(2H, m), 2.52(2H, m), 2.60–2.70(10H, m), 2.98(4H, m), 3.96(1H, m), 6.00(1H, d, J=8Hz), 7.20(1H, d, J=8Hz), 7.57(1H, t, J=8Hz), 7.75–7.82(2H, m), 7.97(1H, d, J=8Hz), 8.17(1H, d, J=8Hz), 8.32(1H, s) |
| 137 | (E)-CH=CH(4-fluoro)phenyl | Mass spectrum(API$^+$): Found 503(MH$^+$). $C_{30}H_{35}FN_4O_2$ requires 502. NMR(CDCl$_3$)δ: 1.10–1.80(4H, m), 1.25(1H, m), 1.44(2H, m), 1.78(2H, m), 2.06(2H, m), 2.50(2H, m), 2.60–2.70(7H, m), 2.90–3.00(4H, m), 3.85(1H, m), 5.39(1H, d, J=8Hz), 6.26(1H, d, J=16Hz), 7.05(2H, t, J=8Hz), 7.20(1H, d, J=8Hz), 7.47(2H, m), 7.57(1H, d, J=16Hz), 7.80–7.90(2H, m). |
| 138 | (E)-CH=CH-(3-F)phenyl | Mass spectrum(API$^+$): Found 503(MH$^+$). $C_{30}H_{35}FN_4O_2$ requires 502. NMR(CDCl$_3$)δ: 1.05–1.20(4H, m), 1.20–1.30(1H, m), 1.40–1.50(2H, m), 1.75–1.85(2H, m), 2.00–2.10(2H, m), 2.45–2.55(2H, m), 2.60–2.70(7H, m), 2.90–3.05(4H, m), 3.80–3.90(1H, m), 5.41(1H, d, J=8Hz), 6.33(1H, d, J=15Hz), 6.95–7.05(1H, m), 7.13–7.20(2H, m), 7.20–7.25(1H, m), 7.27–7.35(1H, m), 7.56(1H, d, J=15Hz), |

TABLE 3-continued

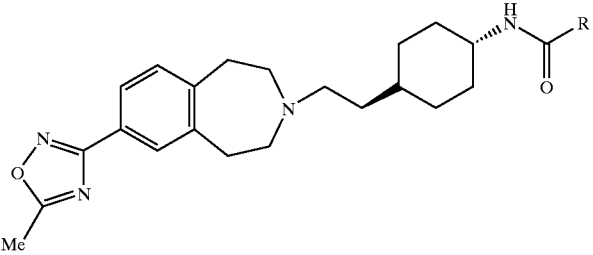

| Example No. | R | Mass spectrum, ¹H NMR |
|---|---|---|
| 139 | (E)-CH=CH-(2-F)phenyl | 7.75–7.85(2H, m). Mass spectrum(API⁺): Found 503(MH⁺). $C_{30}H_{35}FN_4O_2$ requires 502. NMR(CDCl₃)δ: 1.06–1.30(5H, m), 1.40–1.50(2H, m), 1.75–1.85(2H, m), 2.00–2.10(2H, m), 2.45–2.55(2H, m), 2.60–2.70(7H, m), 2.90–3.00(4H, m), 3.80–3.90(1H, m), 5.42(1H, d, J=8Hz), 4.49(1H, d, J=15 Hz), 7.10–7.22(3H, m), 7.26–7.31(1H, m), 7.40–7.50(1H, m). 7.66(1H, d, J=15Hz), 7.75–7.85(2H, m). |

TABLE 4

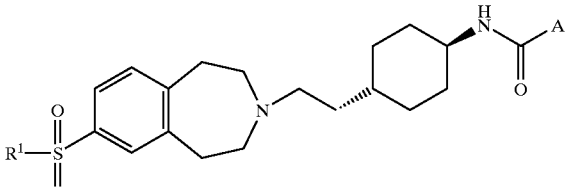

| Example | R¹ | A | Mass spectrum |
|---|---|---|---|
| 140 | Me | trans-CH=CHC₆H₄(2-F) | Found: 499(MH⁺) $C_{28}H_{35}N_2SO_3F$ requires 498 |
| 141 | Me | —C₆H₄(3-(2-(4-Methyl)-oxazolyl)) | Found: 536(MH⁺) $C_{30}H_{37}N_3SO_4$ requires 535 |
| 142 | Me | —C₆H₄(3-trifluoromethyl) | Found: 523 (MH⁺)$C_{27}H_{33}N_2SO_3F_3$ requires 522 |
| 143 | Me | 5-quinolinyl(8-Cl, 2-Me) | Found: 554(MH⁺) $C_{30}H_{36}N_3SO_3Cl$ requires 553 |
| 163 | Me | 5-quinolinyl(8-F, 2-Me) | Found: 538(MH⁺) $C_{30}H_{36}FN_3O_3S$ requires 537 |

The substituted benzazepines required as intermediates for the compounds of Table 5 were prepared from the compounds of Descriptions 8, 9, or 13, using standard methods for functional group transformation and heterocyclic ring synthesis or by palladium-catalysed cross-coupling reactions.

TABLE 5

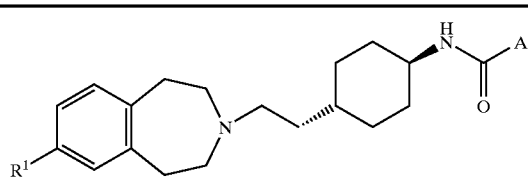

| Example | R¹ | A | Mass Spectrum (API⁺) |
|---|---|---|---|
| 144 | 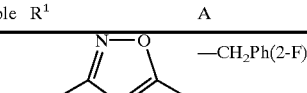 | —CH₂Ph(2-F) | Found 490 (MH⁺). $C_{30}H_{36}FN_3O_2$ requires 489. |

TABLE 5-continued

[Structure: benzazepine with R¹ substituent, connected via ethyl linker to cyclohexyl-NH-C(=O)-A]

| Example | R¹ | A | Mass Spectrum (API⁺) |
|---|---|---|---|
| 145 | 2-methyl-5-oxazolyl (Me on 5, linked at 2) | trans-CH=CH-Ph(4-F) | Found 502 (MH⁺). $C_{31}H_{36}FN_3O_2$ requires 501. |
| 146 | 5-methyl-3-isoxazolyl | trans-CH=CH-Ph(4-F) | Found 502 (MH⁺). $C_{31}H_{36}FN_3O_2$ requires 501. |
| 147 | 5-methyl-3-isoxazolyl | —CH$_2$Ph(4-F) | Found 490 (MH⁺). $C_{30}H_{36}FN_3O_2$ requires 489. |
| 148 | 2-pyridyl | trans-CH=CH-Ph(4-F) | Found 498 (MH⁺). $C_{32}H_{36}FN_3O$ requires 497. |
| 149 | 2-pyrimidinyl | trans-CH=CH-Ph(4-F) | Found 499 (MH⁺). $C_{31}H_{35}FN_4O$ requires 498. |
| 151 | 1-(pyrrolidin-1-yl)carbonyl | trans-CH=CH-Ph(4-F) | Found 518 (MH⁺). $C_{32}H_{40}FN_3O_2$ requires 517. |
| 152 | 1-(pyrrolidin-1-yl)carbonyl | 3-(7-aza)indolyl | Found 514 (MH⁺). $C_{31}H_{39}N_5O_2$ requires 513. |
| 153 | 5-pyrimidinyl | 3-(3-(5-methyl)-1,2,4-oxadiazolyl)phenyl | Found 537 (MH⁺). $C_{32}H_{36}N_6O_2$ requires 536. |
| 154 | 5-pyrimidinyl | 5-quinolinyl(2-Me) | Found 520 (MH⁺). $C_{33}H_{37}N_5O$ requires 519. |
| 155 | 5-pyrimidinyl | trans-CH=CH-Ph(4-F) | Found 499 (MH⁺). $C_{31}H_{35}FN_4O$ requires 498. |
| 156 | 5-methyl-3-isoxazolyl | 5-quinolinyl(2-Me) | Found 523 (MH⁺). $C_{33}H_{38}N_4O_2$ requires 522. |
| 157 | 5-methyl-3-isoxazolyl | trans-CH=CHC$_6$H$_4$(2-CN) | Found 509 (MH⁺). $C_{32}H_{36}N_4O_2$ requires 508. |
| 158 | 5-methyl-3-isoxazolyl | trans-CH=CHC$_6$H$_4$(3-CN) | Found 509 (MH⁺). $C_{32}H_{36}N_4O_2$ requires 508. |
| 159 | 5-methyl-3-isoxazolyl | trans-CH=CHC$_6$H$_4$(4-CN) | Found 509 (MH⁺). $C_{32}H_{36}N_4O_2$ requires 508. |
| 161 | MeSO$_2$O— | 5-quinolinyl(8-F, 2-Me) | Found 554 (MH⁺). $C_{30}H_{36}FN_3O_4S$ requires 553. |
| 162 | MeSO$_2$O— | —C$_6$H$_4$(3-(2-(5-Methyl)-oxazolyl)) | Found 552 (MH⁺). $C_{30}H_{37}N_3O_5S$ requires 551. |

Example 12 trans-(E)-7-Cyano-3-(2-(1-(4-(3-(4-fluoro)
phenylpropenoyl)amino)cyclohexyl)ethyl)-2,3,4,5-
tetrahydro-1H-3-benzazepine A mixture of trans-3-(2-(1-(4-amino)cyclohexyl)ethyl)-7-cyano-2,3,4,5-tetrahdyro-1H-3-benzazepine (103 mg, 0.35 mmol), 4-fluorocinnamic acid (58 mg, 0.35 mmol), 1-(3-dimethylaminopropyl)-3-ethylcarbodiimide hydrochloride (67 mg, 0.35 mmol), and 1-hydroxybenzotriazole (20 mg, 0.15 mmol) in dichloromethane (8 ml) was shaken at room temperature for 16 h. The reaction mixture was washed with saturated sodium bicarbonate (4 ml). The resulting precipitate was collected by filtration, washed with water (2×10 ml), and dried to give the title compound (87 mg, 56%) as a colourless solid.

Mass spectrum (API$^+$): Found 446 (MH$^+$). $C_{28}H_{32}FN_3O$ requires 445. $^1$H NMR (DMSO-d$_6$) δ: 0.94–1.31 (8H, m), 1.81 (4H, m), 2.40 (5H, m), 3.04 (4H, m), 3.63 (1H, m), 6.54 (1H, d, J=16 Hz), 7.32 (4H, m), 7.59 (4H, m), 7.99 (1H, d, J=8 Hz).

Example 13 trans-7-Cyano-3-(2-(1-(4-(3-pyrrolo[2,3-b]pyridyl)
carboxamido)cyclohexyl)ethyl)-2,3,4,5-tetrahydro-
1H-3-benzazepine A mixture of trans-3-(2-(1-(4-amino)cyclohexyl)ethyl)-7-cyano-2,3,4,5-tetrahydro-1H-3-benzazepine (103 mg, 0.35 mmol), 3-pyrrolo[2,3-b]pyridyl carboxylic acid (56 mg, 0.35 mmol), 1-(3-dimethylaminopropyl)-3-ethylcarbodiimide hydrochloride (67 mg, 0.35 mmol) and 1-hydroxybenzotriazole (20 mg, 0.15 mmol) in dichloromethane (8 ml) was shaken at room temperature for 16 h. The reaction mixture was washed with saturated aqueous sodium bicarbonate (4 ml). The resulting precipitate was collected by filtration, washed with water (2×10 ml) and dried to give the title compound (81 mg, 0.18 mmol, 53%) as a colourless solid.

Mass spectrum (API$^+$): Found 442 (MH$^+$). $C_{27}H_{31}N_5O$ requires 441. $^1$H NMR (DMSO-d$_6$) δ: 1.02 (2H, m), 1.15–1.45 (6H, m), 1.81 (4H, m), 2.50 (5H, m), 2.91 (4H, m), 3.73 (1H, m), 7.14 (1H, m), 7.32 (4 H, d, J=8 Hz), 7.57 (2H, m), 7.73 (1H, d, J=8 Hz), 8.16 (1H, m), 8.25 (1H, m), 8.42 (1H, m), 12.03 (1H, br s).

Example 14 trans-7-Cyano-3-(2-(1-(4-(3-(5-methyl)-1,2,4-
oxadiazolyl)benzoyl)amino)-cyclohexyl)ethyl)-2,3,4,
5-tetrahydro-1H-3-benzazepine A mixture of trans-3-(2-(1-(4-amino)cyclohexyl)ethyl-7-cyano-2,3,4,5-tetrahydro-1H-3-benzazepine (103 mg, 0.35 mmol), 3-(3-(5-methyl)-1,2,4-oxadiazolyl)benzoic acid (71 mg, 0.35 mmol), 1-(3-dimethylaminopropyl)-3-ethylcarbodiimide hydrochloride (67 mg, 0.35 mmol) and 1-hydroxybenzotriazole (20 mg, 0.15 mmol) in dichloromethane (8 ml) was shaken at room temperature for 16 h. The reaction mixture was washed with saturated aqueous sodium bicarbonate (4 ml). The organic layer was pipetted onto a 10 g pre-packed silica column and eluted with 30–100% ethyl acetate in hexane. The fractions containing the title compound were combined and evaporated in vacuo to give the title compound (119 mg, 71%) as a colourless solid.

Mass spectrum (API$^+$): Found 484. $C_{29}H_{33}N_5O_2$ requires 483. $^1$H NMR (CDCl$_3$) δ: 1.08–1.35 (5H, m), 1.45 (2H, m), 1.84 (2H, m), 2.12 (2H, m), 2.50 (2H, m), 2.62 (4H, m), 2.68 (3H, s), 2.96 (4H, m), 3.95 (1H, m), 6.02 (1H, d, J=8 Hz), 7.17 (1H, d, J=8 Hz), 7.41 (2H, m), 7.57 (1H, t, J=8 Hz), 7.98 (1H, m), 8.17 (1H, m), 8.32 (1H, m).

Example 15 trans-(E)-7-Cyano-3-(2-(1-(4-(5-quinolinyl)
carboxamido)cyclohexyl)ethyl)-2,3,4,5-tetrahydro-
1H-benzazepine A mixture of trans-3-(2-(1-(4-amino)cyclohexyl)ethyl)-7-cyano-2,3,4,5-tetrahydro-1H-benzazepine (0.10 g, 0.34 mmol), quinoline-5-carboxylic acid (0.057 g, 0.37 mmol), 1-ethyl-3-(3-dimethylaminopropyl)carbodiimide hydrochloride (0.065 g, 0.34 mmol), 1-hydroxybenzotriazole (catalytic amount) and dichloromethane (8 ml) was shaken for 16 h. Saturated sodium bicarbonate (4 ml) was then added and the mixture shaken for 0.25 h. Chromatography on the organic layer on silica eluting with a gradient of 30–100% ethyl acetate in hexane and then 0–10% methanol in ethyl acetate gave the title compound (0.130 g, 86%).

Mass spectrum (API$^+$) Found 453 (MH$^+$). $C_{29}H_{32}N_4O$ requires 452. $^1$H NMR (CDCl$_3$) δ: 1.12–1.35 (5H, m), 1.41–1.51 (2H, m), 1.83–1.89 (2H, m), 2.15–2.24 (2H, m), 2.48–2.55 (2H, m), 2.60–2.66 (4H, m), 2.91–2.99 (4H, m), 3.97–4.13 (1H, m), 5.86 (1H, d, J=8 Hz), 7.18 (1H, d, J=8 Hz), 7.37–7.49 (3H, m), 7.63–7.70 (2H, m), 8.15–8.20 (1H, m), 8.71–8.76 (1H, m), 8.94–8.96 (1H, m).

Example 16 trans-(E)-7-Cyano-3-(2-(1-(4-(3-(3-acetylamino)
phenylpropenoyl)amino)cyclohexyl)ethyl)-2,3,4,5-
tetrahydro-1H-3-benzazepine A mixture of trans-3-(2-(1-(4-amino)cyclohexyl)ethyl)-7-cyano-2,3,4,5-tetrahydro-1H-3-benzazepine (0.10 g, 0.34 mmol), 3-acetamido cinnamic acid (0.076 g, 0.42 mmol), 1-ethyl-3-(3-dimethylaminopropyl)carbodiimide hydrochloride (0.071 g, 0.42 mmol), 1-hydroxybenzotriazole (catalytic amount) and dichloromethane (8 ml) was shaken for 16 h. Saturated sodium bicarbonate (4 ml) was then added and the mixture shaken for 0.25 h. The precipitated solid was filtered off and washed with water then diethyl ether, and dried to give the title compound (0.12 g, 74%) as a colourless solid.

Mass spectrum (API$^+$): Found 485 (MH$^+$). $C_{30}H_{36}N_4O_2$ requires 484. $^1$H NMR (CDCl$_3$+CD$_3$OD) δ: 1.02–1.35 (5H, m), 1.35–1.50 (2H, m), 1.77–1.82 (2H, m), 2.00–2.04 (2H, m), 2.17 (3H, s), 2.47–2.55 (6H, m), 2.93–2.99 (4H, m), 1.77–1.82 (2H, (1H, m), 6.41 (1H, d, J=15 Hz), 7.17–7.30 (4H, m), 7.38–7.43 (3H, m), 7.50 (1H, d, J=16 Hz), 7.80 (1H, s).

Example 17 trans-7-Cyano-3-(2-(1-(4-(6-(3,4-dihydro-3-oxo)-
2H-benzoxazinyl)carboxamido)-cyclohexyl)ethyl)-2,
3,4,5-tetrahydro-1H-benzazepine A mixture of trans-3-(2-(1-(4-amino)cyclohexyl)ethyl)-7-cyano-2,3,4,5-tetrahydro-1H-3-benzazepine (0.10 g, 0.34 mmol), 2,3-dihydro-3-oxo-4H-benzoxazine-6-carboxylic acid (0.072 g, 0.42 mmol), 1-ethyl-3-(3-dimethylaminopropyl)carbodiimide hydrochloride (0.071 g, 0.42 mmol), 1-hydroxybenzotriazole (catalytic amount) and dichloromethane (8 ml) was shaken for 16 h. Saturated sodium bicarbonate (4 ml) was then added and the mixture shaken for 0.25 h. The precipitated solid was filtered off and washed with water then diethyl ether, and dried to give the title compound (0.16 g, 100%) as a colourless solid.

Mass spectrum (API+): Found 473 (MH+). $C_{28}H_{32}N_4O_3$ requires 472. $^1$H NMR (DMSO-$d_6$) δ: 0.95–1.50 (7H, m), 1.75–1.95 (4H, m), 2.40–2.65 (6H, m), 2.93–3.05 (4H, m), 3.69–3.82 (1H, m), 4.67 (2H, s), 7.02 (1H, d, J=8 Hz), 7.39 (1H, d, J=8 Hz), 7.46–7.50 (2H, m), 7.65 (2H, m), 8.13 (1H, d, J=8 Hz).

Example 18 trans-(E)-7-Cyano-3-(2-(1-(4-(3-(6-(1,2-dihydro-2-oxo)quinolinyl)propenoyl)amino)-cyclohexyl)ethyl)-2,3,4,5-tetrahydro-1H-3-benzazepine A mixture of trans-3-(2-(1-(4-amino)cyclohexyl)ethyl)-7-cyano-2,3,4,5-tetrahydro-1H-3-benzazepine (288 mg, 0.97 mmol), trans-3-(6-(1,2-dihydro-2-oxo)quinolinyl)-propenoic acid (250 mg, 1.16 mmol), 1-ethyl-3-(3-dimethylaminopropyl)carbodiimide hydrochloride (204 mg, 1.07 mmol), 1-hydroxybenzotriazole (catalytic amount) and DMF (20 ml) was shaken for 18 h. Saturated sodium bicarbonate (8 ml) was then added and the mixture shaken for 0.25 h. The resulting precipitate was filtered and dried in vacuo to give the title compound (370 mg, 77%) as a colourless solid.

Found: 495 (MH+). $C_{31}H_{34}N_4O_2$ requires 494. $^1$H NMR (DMSO-$d_6$) δ: 0.94–1.05 (2H, m), 1.10–1.30 (3H, m), 1.30–1.40 (2H, m) 1.74–1.80 (2H, m), 1.80–1.88 (2H, m), 2.44 (2H, t, J=7.5 Hz), 2.45–2.55 (4H, m), 2.85–2.95 (4H, m), 3.55–3.65 (1H, m), 6.50–6.60 (2H, m), 7.28–7.35 (2H, m), 7.40 (1H, d, J=16 Hz), 7.55–7.60 (2H, m), 7.68–7.72 (1H, m), 7.81 (1H, s), 7.93 (1H, d, J=16 Hz), 7.94–8.00 (2H, m).

Example 19 trans-(E)-7-Cyano-3-(2-(1-(4-(3-(2-fluoro-4-acetylamino)phenylpropenoyl)amino)-cyclohexyl)ethyl)-2,3,4,5-tetrahydro-1H-3-benzazepine A mixture of trans-3-(2-(1-(4-amino)cyclohexyl)ethyl)-7-cyano-2,3,4,5-tetrahydro-1H-3-benzazepine (150 mg, 0.51 mmol), (E)-(2-fluoro-4-acetylamino)phenylpropenoic acid (113 mg, 0.51 mmol), EDC. hydrochloride (97 mg, 0.51 mmol) and 1-hydroxybenzotriazole in dichloromethane (10 ml) was shaken at room temperature for 16 h. The reaction mixture was washed with saturated aqueous sodium bicarbonate (4 ml) and the precipitate collected by filtration and then re-suspended in water and filtered before drying in vacuo to give the title compound as an off white solid (200 mg, 79%).

Mass spectrum (API+): Found 503. $C_{30}H_{35}FN_4O_2$ requires 502. $^1$H NMR δ (DMSO-$d_6$+TFA): 0.95–1.34 (5H, m), 1.61 (2H, m), 1.82 (4H, m), 2.07 (3H, s), 3.06 (2H, m), 3.18 (6H, m), 3.68 (3H, m), 6.59 (1H, d, J=16 Hz), 7.34 (2H, m), 7.39–7.63 (3H, m), 7.72 (2H, m), 8.03 (1H, d, J=8 Hz), 9.74 (1H, br s), 10.29 (1H, s).

Example 20 trans-(E)-7-Cyano-3-(2-(1-(4-(3-(8-(1,2-dihydro-2-oxo)quinolinyl)propenoyl)amino)cyclohexyl)ethyl)-2,3,4,5-tetrahydro-1H-3-benzazepine A mixture of trans-3-(2-(1-(4-amino)cyclohexyl)ethyl-7-cyano-2,3,4,5-tetrahydro-1H-3-benzazepine (0.25 g, 0.84 mmol), (E)-3-(8-(1,2-dihydro-2-oxo)quinolinyl)propenoic acid (0.27 g, 1.2 mmol), EDC. hydrochloride (0.3 g, 1.5 mmol) and 1-hydroxybenzotriazole (50 mg) in DMF (10 ml) was allowed to stir at 80° C. for 4 h, then poured into water (500 ml). The precipitate was collected by filtration and then re-suspended in aqueous sodium bicarbonate solution. Resulting solid was collected by filtration, then washed with water and diethyl ether, then was dried in vacuo to give the title compound (0.42 g, 95%) as a yellow solid.

Found: 495 (MH+). $C_{31}H_{34}N_4O_2$ requires 494. δ (DMSO-$d_6$+TFA): 1.00–1.15 (2H, m), 1.15–1.30 (3H, m), 1.50–1.70 (2H, m), 1.70–1.85 (2H, m), 1.85–1.95 (2H, m), 2.95–3.30 (8H, m), 3.60–3.80 (3H, m), 6.45–6.60 (2H, m), 7.23 (1H, t, J=8 Hz), 7.46 (1H, d, J=8 Hz), 7.60–7.80 (4H, m), 7.94 (1H, d, J=10 Hz), 7.95–8.10 (3H, m), 9.70 (1H, br s).

Example 21 trans-7-Cyano-3-(2-(1-(4-(5-(8-fluoro)quinolinyl) carboxamido)cyclohexyl)ethyl)-2,3,4,5-tetrahydro-1H-3-benzazepine A mixture of trans-3-(2-(1-(4-amino)cyclohexyl)ethyl)-7-cyano-2,3,4,5-tetrahydro-1H-3-benzazepine (0.162 g, 0.545 mmol), 8-fluoroquinoline-5-carboxylic acid (0.115 g, 0.6 mmol), 1-(3-dimethylaminopropyl)-3-ethylcarbodiimide hydrochloride (0.115 g, 0.6 mmol) and 1-hydroxybenzotriazole hydrate (0.01 g, 0.065 mmol) in dichloromethane (7 ml) was shaken for 18 h. Saturated aqueous sodium hydrogen carbonate (6 ml) was added and shaking continued for 0.5 h. The organic layer was separated and pipetted onto a column of silica (10 g). Elution with 30–100% ethyl acetate-hexane gradient then 1–10% methanol-ethyl acetate gradient yielded the title compound as a colourless solid (0.22 g, 85%).

Mass spectrum (API+): Found 471 (MH+). $C_{29}H_{31}FN_4O$ requires 470. $^1$H NMR (CDCl$_3$) δ: 1.05–1.40 (5H, m), 1.45 (2H, m), 1.85 (2H, m), 2.20 (2H, m), 2.55 (2H, m), 2.63 (4H, m), 2.96 (4H, m), 4.00 (1H, m), 5.86 (1H, d, J=8 Hz), 7.17 (1H, d, J=8 Hz), 7.30–7.45 (3H,m), 7.54 (1H, m), 7.62 (1H, m), 8.80 (1H, d, J=8 Hz), 9.01 (1H, m).

Example 22 trans-7-Acetyl-3-(2-(1-(4-(5-quinolinyl) carboxamido)cyclohexyl)ethyl)-2,3,4,5-tetrahydro-1H-3-benzazepine A mixture of 7-acetyl-trans-3-(2-(1-(4-amino)cyclohexyl) ethyl)-2,3,4,5-tetrahydro-1H-3-benzazepine (0.105 g, 0.334 mmol), quinoline-5-carboxylic acid (0.064 g, 0.368 mmol), 1-(3-dimethylaminopropyl)-3-ethylcarbodiimide hydrochloride (0.071 g, 0.368 mmol) and 1-hydroxybenzotriazole hydrate (0.01 g, 0.065 mmol) in dichloromethane (6 ml) was shaken for 18 h. Saturated aqueous sodium hydrogen carbonate (6 ml) was added and shaking continued for a further 0.5 h. The organic layer was separated and pipetted onto a column of silica (10 g). Elution with 30–100% ethyl acetate-hexane gradient then 1–10% methanol—ethyl acetate gradient gave the title compound as a colourless solid (0.1 g, 64%).

Mass spectrum (API+): Found 470 (MH+); $C_{30}H_{35}N_3O_2$ requires 469. $^1$H NMR (CDCl$_3$) δ: 1.10–1.40 (5H, m), 1.48 (2H, m), 1.86 (2H, m), 2.33 (2H, m), 2.55 (2H, m), 2.58 (3H, s), 2.65 (4H, m), 2.98 (4H, m), 4.02 (1H, m), 5.88 (1H, d, J=8 Hz), 7.17 (1H, d, J=8 Hz), 7.20 (1H, m), 7.55–7.75 (4H, m), 8.15 (1H, m), 8.75 (1H, d, J=8 Hz), 8.95 (1H, m).

Example 23 trans-3-(2-(1-(4-(5-(2-Methyl)quinolinyl)
carboxamido)cyclohexyl)ethyl)-7-methylsulphonyl-
2,3,4,5-tetrahydro-1H-3-benzazepine

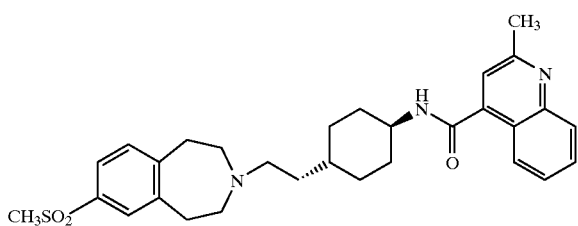

A mixture of trans-3-(2-(1-(4-amino)cyclohexyl)ethyl)-7-methylsulphonyl-2,3,4,5-tetrahydro-1H-3-benzazepine (100 mg, 0.29 mmol), 2-methyl-quinoline-5-carboxylic acid (64 mg, 0.34 mmol), 1-ethyl-3-(3-dimethylaminopropyl) carbodiimide hydrochloride (59 mg, 0.31 mmol) and 1-hydroxybenzotriazole (cat. amt.) in dichloromethane (10 ml) was shaken at room temperature for 18 h. A saturated solution of sodium bicarbonate (4 ml) was then added and the mixture shaken for 0.25 h. The organic layer was then applied directly to a silica column eluted with a gradient of 30–100% ethyl acetate in hexane and then 0–10% methanol in ethyl acetate to give the title compound (95 mg, 66%) as a colourless solid.

$^1$H NMR δ (CDCl$_3$) 1.15–1.30 (5H, m), 1.44–1.50 (2H, m), 1.82–1.88 (2H, m), 2.15–2.20 (2H, m), 2.53 (2H, t, J=7.6 Hz), 2.62–2.68 (4H, m), 2.75 (3H, s), 2.98–3.02 (4H, m), 3.04 (3H, s), 3.95–4.05 (1H, m), 5.84 (1H, d, J=8.2 Hz), 7.28 (1H, d, J=7.9 Hz), 7.35 (1H, d, J=8.8 Hz), 7.56–7.70 (4H, m), 8.08 (1H, d), 8.62 (1H, d). Mass spectrum: API$^+$ 520 (MH$^+$): C$_{30}$H$_{37}$N$_3$SO$_3$ requires 519.

Example 24 trans-3-(2-(1-(4-(3-(3-(5-Methyl)-1,2,4-oxadiazolyl)
benzoyl)amino)cyclohexyl)ethyl)-7-
methylsulphonyl-2,3,4,5-tetrahydro-1H-3-
benzazepine A mixture of trans-3-(2-(1-(4-amino)cyclohexyl)-7-methylsulphonyl-2,3,4,5-tetrahydro-1H-3-benzazepine (100 mg, 0.29 mmol), 3-(3-(5-methyl)-1,2,4-oxadiazolyl)-benzoic acid (69 mg, 0.34 mmol), 1-ethyl-3-(3-dimethylaminopropyl)carbodiimide hydrochloride (59 mg, 0.31 mmol) and 1-hydroxybenzotriazole (cat. amt.) in dichloromethane (10 ml) was shaken at room temperature for 18 h. A saturated solution of sodium bicarbonate (4 ml) was then added and the mixture shaken for 0.25 h. The organic layer was then applied directly to a silica column eluted with a gradient of 30–100% ethyl acetate in hexane and then 0–10% methanol in ethyl acetate to give the title compound (103 mg, 69%) as a colourless solid.

$^1$H NMR δ (CDCl$_3$): 1.08–1.30 (5H, m), 1.40–1.46 (2H, m), 1.80–1.85 (2H, m), 2.08–2.15 (2H, m), 2.52 (2H, t, J=7.8), 2.60–2.65 (4H, m), 2.68 (3H, s), 2.98–3.02 (4H, m), 3.05 (3H, s), 3.90–4.00 (1H, m), 6.01 (1H, d, J=8.0 Hz), 7.28 (1H, d, J=7.28 Hz), 7.57 (1H, t, J=7.8 Hz), 7.65–7.70 (2H, m), 8.0 (1H, d), 8.19 (1H, d, J=7.7 Hz), 8.32 (1H, s). Mass spectrum: API$^+$ 537 (MH$^+$): C$_{29}$H$_{36}$N$_4$SO$_4$ requires 536.

Example 25 trans-7-(5-(3-Methyl)-1,2,4-oxadiazolyl)-3-(2-(1-(4-
(3-pyrrolo[2,3-b]pyridyl)carboxamido)cyclohexyl)
ethyl)-2,3,4,5-tetrahydro-1H-3-benzazepine,
Hydrochloride A mixture of trans-3-(2-(1-(4-amino)cyclohexyl)-7-(5-(3-methyl)-1,2,4-oxadiazolyl)-2,3,4,5-tetrahydro-1H-3-benzazepine (21.0 g, 59.3 mmol), pyrrolo[2,3-b]pyridyl-3-carboxylic acid (10.57 g, 65.2 mmol), EDC hydrochloride (12.46 g, 64.4 mmol) and HOBT (0.5 g) in CH$_2$Cl$_2$ (630 ml) and DMF (84 ml) was stirred at ambient temperature for 16 h. Saturated aqueous sodium bicarbonate (350 ml) was added and the mixture stirred for 0.25 h. The precipitate was collected by filtration, washed in turn with water and diethyl ether and dried in vacuo to give the free base of the title compound (18.0 g, 61%).

Mass spectrum (API$^+$): Found 499 (MH$^+$). C$_{29}$H$_{34}$N$_6$O$_2$ requires 498. NMR (DMSO-d$_6$) δ: 0.90–1.10 (2H, m), 1.10–1.40 (5H, m), 1.70–1.90 (4H, m), 2.40–2.70 (6H, m), 2.96 (3H, s), 3.31 (4H, m), 3.89 (1H, m), 7.15 (1H, m), 7.36 (1H, d, J=8 Hz), 7.71 (1H, d, J=8 Hz), 7.75–7.85 (2H, m), 8.12 (1H, s), 8.20 (1H, s), 8.35 (1H, d, J=8 Hz), 12.02 (1H, br s).

To a suspension of the above free base (18.0 g, 36 mmol) in 10% methanol-dichloromethane (500 ml) was added a 1M solution of HCl in diethyl ether (37.08 ml). The resulting solution was evaporated in vacuo and the residue crystallised from methanol to give the title compound as a colourless solid (12.5 g, m.p. 275–276° C.).

Example 26 trans-(E)-7-(3-(5-Methyl)-1,2,4-oxadiazolyl)-3-(2-
(1-(4-(3-(4-fluoro)phenylpropenoyl)amino)
cyclohexyl)ethyl)-2,3,4,5-tetrahydro-1H-3-
benzazepine

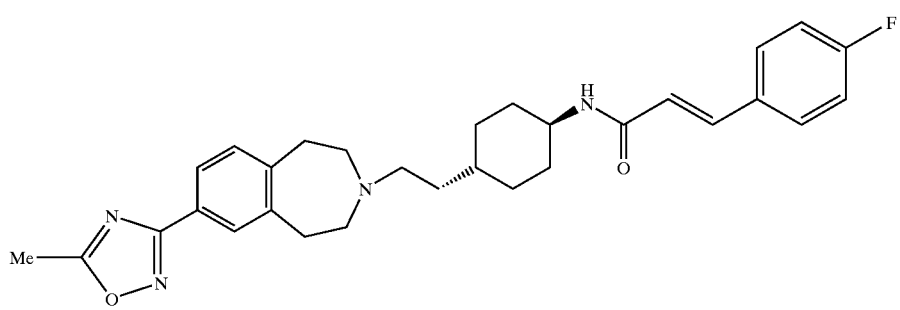

Alternative Name: (2E)-3-(4-fluorophenyl)-N-[trans-4-[2-[2,3,4,5-tetrahydro-7-(5-methyl-1,2,4-oxadiazol-3-yl)-1H-3-benzazepin-3-yl]ethyl]cyclohexyl]-2-propenamide A mixture of trans-3-(2-(1-(4-amino)cyclohexyl)ethyl)-7-(3-(5-methyl)-1,2,4-oxadiazolyl)-2,3,4,5-tetrahydro-1H-3-benzazepine (0.1 g, 0.28 mmol), (E)-4-fluorocinnamic acid (0.046 g, 0.28 mmol), EDC hydrochloride (0.06 g, 0.31 mmol) and HOBT (0.015 g) in dichloromethane (8 ml) was stirred at ambient temperature for 64 h, then was washed with saturated aqueous sodium bicarbonate (4 ml). The organic phase was purified by silica gel chromatography eluting with 0–10% methanol in ethyl acetate, to give the title compound (0.12 g, 85%) as a colourless solid.

Mass spectrum (API$^+$): Found 503 (MH$^+$). $C_{30}H_{35}FN_4O_2$ requires 502. NMR (CDCl$_3$) δ: 1.10–1.80 (4H, m), 1.25 (1H, m), 1.44 (2H, m), 1.78 (2H, m), 2.06 (2H, m), 2.50 (2H, m), 2.60–2.70 (7H, m), 2.90–3.00 (4H, m), 3.85 (1H, m), 5.39 (1H, d, J=8 Hz), 6.26 (1H, d, J=16 Hz), 7.05 (2H, t, J=8 Hz), 7.20 (1H, d, J=8 Hz), 7.47 (2H, m), 7.57 (1H, d, J=16 Hz), 7.80–7.90 (2H, m).

A mixture of trans-3-(2-(1-(4-amino)cyclohexyl)ethyl)-7-(3-(5-methyl)-1,2,4-oxadiazolyl)-2,3,4,5-tetrahydro-1H-3-benzazepine (16.0 g, 0.045 mol), (E)-4-fluorocinnamic acid (7.5 g, 0.045 mol), EDC hydrochloride (9.53 g, 0.050 mol), and HOBT (0.78 g, 0.006 mol) in dichloromethane (0.78L) was stirred under argon at ambient temperature for 111 h. Saturated aqueous sodium bicarbonate (1L) was added and after stirring for 0.25 h, the mixture was filtered and the solid washed with saturated aqueous sodium bicarbonate (2×0.25 L), water (3×0.25 L), diethyl ether (3×0.25L) and dried in vacuo to afford the title compound (18.4 g, 81%) as a colourless solid.

The filtrate was separated and the aqueous layer extracted with dichloromethane (2×0.3 L). The combined extracts were dried and evaporated in vacuo to afford a pale yellow solid (4.5 g). Sequential trituration with dichloromethane (0.08L), saturated aqueous sodium bicarbonate (1×0.5 L; 2×0.2 L), water (3×0.2 L), and diethyl ether (3×0.2 L) followed by drying in vacuo afforded the title compound (2.8 g, 12%) as a colourless solid.

Both batches had spectroscopic data identical to that described above.

To a solution of the free base obtained above (21.2 g, 0.042 mol) in dichloromethane (0.55 L) and methanol (0.1 L) was added 1M hydrogen chloride in diethyl ether (0.051 L, 0.05 mol). The resulting solution was evaporated in vacuo and the residue crystallised from methanol to afford (2E)-3-(4-fluorophenyl)-N-[trans-4-[2-[2,3,4,5-tetrahydro-7-(5-methyl-1,2,4-oxadiazol-3-yl)-1H-3-benzazepin-3-yl]ethyl]cyclohexyl]-2-propenamide monohydrochloride (19.8 g, 91%) as a colourless solid m.p. 259–261° C.

NMR (D$_6$-DMSO) δ: 1.00–1.09 (2H, m), 1.15–1.28 (3H, m), 1.60–1.70 (2H, m), 1.70–1.80 (2H, m), 1.80–1.90 (2H, m), 2.66 (3H, m), 2.95–3.25 (6H, m), 3.35–3.50 (2H, m), 3.55–3.75 (3H, m), 6.55 (1H, d, J=16 Hz), 7.22–7.27 (2H, m), 7.39 (1H, d, J=16 Hz), 7.40–7.45 (1H, m), 7.55–7.64 (2H, m), 7.80–7.85 (1H, m), 7.87 (1H, s), 7.95–8.05 (1H, m), 10.60 (1H, br s).

Example 27 trans-(E)-7-(5-(3-Methyl)-1,2,4-oxadiazolyl)-3-(2-(1-(4-(3-(4-fluoro)phenylpropenoyl)amino)cyclohexyl)ethyl)-2,3,4,5-tetrahydro-1H-3-benzazepine A mixture of trans-3-(2-(1-(4-amino)cyclohexyl)ethyl)-7-(5-(3-methyl)-1,2,4-oxadiazolyl)-2,3,4,5-tetrahydro-1H-3-benzazepine (0.1 g, 0.28 mmol), (E)-4-fluorocinnamic acid (0.046 g, 0.28 mmol) EDC hydrochloride (0.06 g, 0.31 mmol) and HOBT (0.0 15 g) in dichloromethane (8 ml) was stirred at ambient temperature for 64 h, then was washed with saturated aqueous sodium bicarbonate (4 ml). The organic phase was purified by silica gel chromatography eluting with 0–10% methanol in ethyl acetate to give the title compound (0.12 g, 85%) as a colourless solid.

Mass spectrum (API$^+$): Found 503 (MH$^+$). $C_{30}H_{35}FN_4O_2$ requires 502. NMR (CDCl$_3$) δ: 1.10–1.30 (5H, m), 1.40–1.47 (2H, m), 1.78–1.82 (2H, m), 2.00–2.10 (2H, m), 2.46 (3H, s), 2.47–2.52 (2H, m), 2.60–2.70 (4H, m), 2.95–3.05 (4H, m), 3.86 (1H, m), 5.38 (1H, d, J=8 Hz), 6.26 (1H, d, J=16 Hz), 7.05 (2H, t, J=8 Hz), 7.24 (1H, d, J=8 Hz), 7.47 (2H, dd, J=5, 8 Hz), 7.57 (1H, d, J=16 Hz), 7.80–7.90 (2H, m).

Example 28 trans-(E)-7-(5-(3-Methyl)isoxazolyl)-3-(2-(1-(4-(3-(4-fluoro)phenylpropenoyl)amino)cyclohexyl)ethyl)-2,3,4,5-tetrahydro-1H-3-benzazepine A mixture of trans-3-(2-(1-(4-amino)cyclohexyl)ethyl-7-(5-(3-methyl)isoxazolyl)-2,3,4,5-tetrahydro-1H-3-benzazepine (0.1 g, 0.28 mmol), 4-fluorophenylacetic acid (0.044 g, 0.28 mmol), EDC hydrochloride (0.065 g, 0.31 mmol) and HOBT (0.02 g) in CH$_2$Cl$_2$ (8 ml) was stirred at ambient temperature for 16 h, then was washed with saturated sodium bicarbonate (4 ml). The organic phase was purified by silica gel chromatography eluting with 0–10% methanol in ethyl acetate to give the title compound (0.1 g, 73%).

Mass spectrum (API$^+$): Found 490 (MH$^+$). $C_{30}H_{36}FN_3O_2$ requires 489. $^1$H NMR δ (CDCl$_3$): 0.90–1.10 (4H, m), 1.10–1.20 (1H, m), 1.30–1.40 (2H, m), 1.70–1.80 (2H, m), 1.85–1.95 (2H, m), 2.34 (3H, s), 2.40–2.50 (2H, m), 2.55–2.70 (4H, m), 2.90–3.00 (4H, m), 3.50 (2H, s), 3.65–3.80 (1H, m), 5.12 (1H, d, J=8 Hz), 6.30 (1H, s), 7.03 (2H, t, J=8 Hz), 7.15 (1H, d, J=8 Hz), 7.19–7.25 (2H, m), 7.45–7.52 (2H, m).

Example 29 trans-7-(5-(3-Methyl)-1,2,4-oxadiazolyl)-3-(2-(1-(4-(4-fluoro)phenylacetamido)cyclohexyl)ethyl)-2,3,4,5-tetrahydro-1H-3-benzazepine A mixture of trans-3-(2-(1-(4-amino)cyclohexyl)ethyl)-7-(5-(3-methyl)-1,2,4-oxadiazolyl)-2,3,4,5-tetrahydro-1H-3-benzazepine (0.1 g, 0.28 mmol), (4-fluoro)phenylacetic acid (0.044 g, 0.28 mmol), EDC hydrochloride (0.054 g, 0.28 mmol) and HOBT (0.015 g) in dichloromethane (5 ml) was shaken at ambient temperature for 16 h, and saturated aqueous sodium bicarbonate (4 ml) added. The organic phase was purified by silica gel chromatography eluting with 30–100% ethyl acetate in hexane, then 0–10% methanol in ethyl acetate gradient elution to give the title compound (0.095 g, 70%) as a colourless solid.

Mass spectrum (API$^+$): Found 491 (MH$^+$). $C_{29}H_{35}FN_4O_2$ requires 490. $^1$H NMR δ (CDCl$_3$): 0.90–1.30 (5H, m), 1.35–1.50 (2H, m), 1.70–1.80 (2H, m), 1.85–1.95 (2H, m), 2.46 (3H, s), 2.40–2.50 (2H, m), 2.55–2.65 (4H, m), 2.95–3.00 (4H, m), 3.50 (2H, s), 3.60–3.80 (1H, m), 5.13 (1H, d, J=8 Hz), 6.95–7.08 (2H, m), 7.15–7.30 (3H, m), 7.80–7.90 (2H, m).

Example 150 trans-3-(2-(1-(4-(5-(2-Methyl)quinolinyl) carboxamide)cyclohexyl)ethyl)-7-methanesulphonyloxy-2,3,4,5-tetrahydro-1H-3-benzazepine

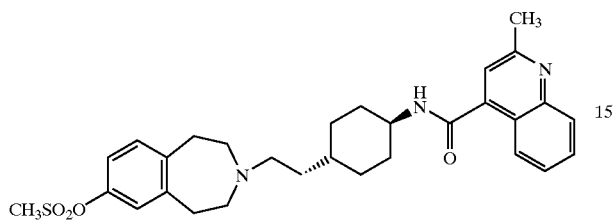

A mixture of trans-3-(2-(1-(4-amino)cyclohexyl)ethyl)-7-methanesulphonyloxy-2,3,4,5-tetrahydro-1H-3-benzazepine (150 mg, 0.41 mmol), 2-methyl-quinoline-5-carboxylic acid (92 mg, 0.49 mmol), 1-ethyl-3-(3-dimethylaminopropyl)carbodiimide hydrochloride (86 mg, 0.45 mmol) and 1-hydroxybenzotriazole (cat. amt.) in dichloromethane (10 ml) was shaken at room temperature for 18 h. A saturated solution of sodium bicarbonate (4 ml) was added and the mixture shaken for 0.25 h. The organic layer was then applied directly to a silica column eluted with a gradient of 30–100% ethyl acetate in hexane and then 0–10% methanol in ethyl acetate to give the title compound (161 mg, 74%) as a colourless solid.

$^1$H NMR (CDCl$_3$) δ: 1.15–1.30 (5H, m), 1.45–1.50 (2H, m), 1.82–1.90 (2H, m), 2.15–2.20 (2H, m), 2.50–2.55 (2H, m), 2.60–2.68 (4H, m), 2.75 (3H, s), 2.90–2.95 (4H, m), 3.13 (3H, s), 3.95–4.05 (1H, m), 5.82 (1H, d,J=8.2 Hz), 7.00–7.03 (2H, m), 7.12 (1H, d, J=7.8 Hz), 7.35 (1H, d, J=8.8 Hz), 7.55–7.70 (2H, m), 8.08 (1H, d, J=8.3 Hz), 8.61 (1H, d). Mass Spectrum (AP$^+$): Found 536 (MH$^+$). C$_{30}$H$_{37}$N$_3$SO$_4$ requires 535.

What is claimed is:

1. A compound of formula (I):

Formula (I)

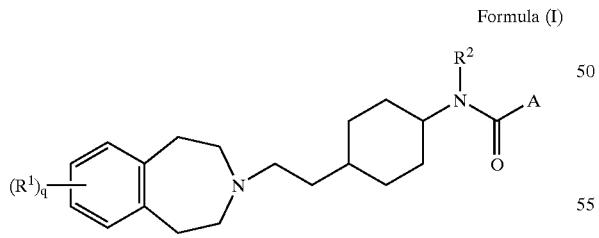

wherein:

R$^1$ represents a substituent selected from: a hydrogen or halogen atom; a hydroxy, cyano, nitro, trifluoromethyl, trifluoromethoxy, trifluoromethanesulfonyloxy, pentafluoroethyl, C$_{1-4}$alkyl, C$_{1-4}$alkoxy, arylC$_{1-4}$alkoxy, C$_{1-4}$alkylthio, C$_{1-4}$alkoxyC$_{1-4}$alkyl, C$_{3-6}$cycloalkylC$_{1-4}$alkoxy, C$_{1-4}$alkanoyl, C$_{1-4}$alkoxycarbonyl, C$_{1-4}$alkylsulfonyl, C$_{1-4}$alkylsulfonyloxy, C$_{1-4}$alkylsulfonylC$_{1-4}$alkyl, arylsulfonyl, arylsulfonyloxy, arylsulfonylC$_{1-4}$alkyl, C$_{1-4}$alkylsulfonamido, C$_{1-4}$alkylamido, C$_{1-4}$alkylsulfonamidoC$_{1-4}$alkyl, C$_{1-4}$alkylamido C$_{1-4}$alkyl, arylsulfonamido, arylcarboxamido, arylsulfonamidoC$_{1-4}$alkyl, arylcarboxamidoC$_{1-4}$alkyl, aroyl, aroylC$_{1-4}$alkyl, or arylC$_{1-4}$alkanoyl group; a group R$^3$OCO(CH$_2$)$_p$, R$^3$CON(R$^4$)(CH$_2$)$_p$, R$^3$R$^4$NCO (CH$_2$)$_p$ or R$^3$R$^4$NSO$_2$(CH$_2$)$_p$ where each of R$^3$ and R$^4$ independently represents a hydrogen atom or a C$_{1-4}$alkyl group or R$^3$R$^4$ forms part of a C$_{3-6}$azacyloalkane or C$_{3-6}$(2-oxo)azacycloalkane ring and p represents zero or an integer from 1 to 4; or a group Ar$^3$—Z, wherein Ar$^3$ represents an optionally substituted phenyl ring or an optionally substituted 5- or 6-membered aromatic heterocyclic ring and Z represents a bond, O, S or CH$_2$;

R$^2$ represents a hydrogen atom or a C$_{1-4}$alkyl group;

q is 1 or 2;

A represents a group of the formula (a), (b), (c) or (d):

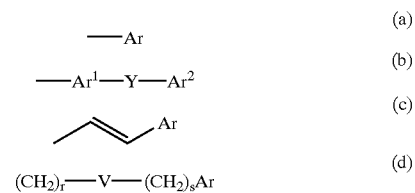

wherein

Ar represents an optionally substituted phenyl ring or an optionally substituted 5- or 6-membered aromatic heterocyclic ring; or an optionally substituted bicyclic ring system;

Ar$^1$ and Ar$^2$ each independently represent an optionally substituted phenyl ring or an optionally substituted 5- or 6-membered aromatic heterocyclic ring; and Y represents a bond, —NHCO—, —CONH—, —CH$_2$—, or —(CH$_2$)$_m$Y$^1$(CH$_2$)$_n$—, wherein Y$^1$ represents O, S, SO$_2$, or CO and m and n each represent zero or 1 such that the sum of m+n is zero or 1; providing that when A represents a group of formula (a), any substituent present in Ar ortho to the carboxamide moiety is necessarily a hydrogen or a methoxy group;

r and s independently represent an integer from zero to 3 such that the sum of r and s is equal to an integer from 1 to 4; and V represents a bond, O or S;

or a salt thereof.

2. A compound or salt as claimed in claim 1 wherein q represents 1.

3. A compound or salt as claimed in claim 1 wherein rings Ar, Ar$^1$, and Ar$^2$ are each independently optionally substituted by one or more substituents selected from: a hydrogen or halogen atom, or a hydroxy, oxo, cyano, nitro, trifluoromethyl, C$_{1-4}$alkyl, C$_{1-4}$alkoxy, C$_{1-4}$alkylenedioxy, C$_{1-4}$alkanoyl, C$_{1-4}$alkylsulfonyl, C$_{1-4}$alkylsulfinyl, C$_{1-4}$alkylthio, R$^7$SO$_2$N(R$^8$)—, R$^7$R$^8$NSO$_2$—, R$^7$R$^8$N—, R$^7$R$^8$NCO—, or R$^7$CON(R$^8$)— group wherein each of R$^7$ and R$^8$ independently represents a hydrogen atom or a C$_{1-4}$ alkyl group, or R$^7$R$^8$ together form a C$_{3-6}$ alkylene chain;

and wherein in the rings Ar and Ar² any substituents positioned ortho to one another may optionally be linked to form a 5- or 6-membered ring.

4. A compound or salt as claimed in claim 3 wherein the one or more optional substituents of the Ar, Ar¹, and Ar² rings are other than trifluoromethyl.

5. A compound or salt as claimed in claim 3, wherein the rings Ar, Ar¹, and Ar² are each independently optionally substituted by one substituent selected from: a hydrogen or halogen atom, or a hydroxy, oxo, cyano, nitro, trifluoromethyl, $C_{1-4}$alkyl, $C_{1-4}$alkoxy, $C_{1-4}$alkylenedioxy, $C_{1-4}$alkanoyl, $C_{1-4}$alkylsulfonyl, $C_{1-4}$alkylsulfinyl, $C_{1-4}$alkylthio, $R^7SO_2N(R^8)$—, $R^7R^8NSO_2$—, $R^7R^8N$—, $R^7R^8NCO$—, or $R^7CON(R^8)$— group wherein each of $R^7$ and $R^8$ independently represents a hydrogen atom or a $C_{1-4}$ alkyl group, or $R^7R^8$ together form a $C_{3-6}$ alkylene chain; and wherein in the rings Ar and Ar² any substituents positioned ortho to one another may optionally be linked to form a 5- or 6-membered ring.

6. A compound or salt as claimed in claim 1, wherein A is the group of the formula (b).

7. A compound or salt as claimed in claim 6 wherein Ar¹ is optionally substituted phenyl.

8. A compound or salt as claimed in claim 6 wherein Y is a bond.

9. A compound or salt as claimed in claim 6 wherein Ar² is optionally substituted phenyl, pyridyl, pyrimidinyl, isoxazolyl, oxazolyl or oxadiazolyl.

10. A compound or salt as claimed in claim 13 wherein R¹ is defined as follows:
  (a) when R¹ represents an aryl$C_{1-4}$alkoxy, arylsulfonyl, arylsulfonyloxy, arylsulfonyl$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group, the aryl moiety is selected from an optionally substituted phenyl ring or an optionally substituted 5- or 6-membered heterocyclic ring; and
  (b) wherein, in the group R¹ any aryl moiety is optionally substituted by one or more substituents selected from hydrogen, halogen, amino, cyano, $C_{1-4}$alkyl, $C_{1-4}$alkylamino, $C_{1-4}$dialkylamino, $C_{1-4}$alkanoyl, or $R^5R^6NCO$ where each of $R^5$ and $R^6$ independently represents a hydrogen atom or $C_{1-4}$alkyl group.

11. A compound or salt as claimed in claim 10 wherein in the group R¹ any aryl moiety is optionally substituted by one substituent selected from hydrogen, halogen, amino, cyano, $C_{1-4}$alkyl, $C_{1-4}$alkylamino, $C_{1-4}$dialkylamino, $C_{1-4}$alkanoyl, or $R^5R^6NCO$ where each of $R^5$ and $R^6$ independently represents a hydrogen atom or $C_{1-4}$alkyl group.

12. A compound or salt as claimed in claim 1 wherein R¹ represents a substituent selected from a halogen atom, methyl cyano, acetyl, trifluoromethyl, pentafluoroethyl, methylsulphonyl, methylsulphonyloxy or trifluoromethoxy group; or a group Ar³—Z, where Z is a bond and Ar³ is a 5- or 6-membered ring heterocycle, optionally substituted by a methyl group, containing at least one N and one O atom.

13. A compound or salt as claimed in claim 1 wherein, in the groups Ar, Ar¹, Ar² and Ar³, any optionally substituted 5- or 6-membered heterocyclic aromatic ring contains from 1 to 4 heteroatoms selected from O, N or S; and when the ring contains 2–4 heteroatoms, one is selected from O, N and S and the remaining heteroatom is N.

14. A compound or salt as claimed in claim 1 wherein R² is a hydrogen atom.

15. A compound or salt as claimed in claim 1 which is in the trans configuration with respect to the cyclohexyl ring.

16. A process for preparing a compound or salt of formula (I) as defined in claim 1 which process comprises:

(a) reacting a compound of formula(II):

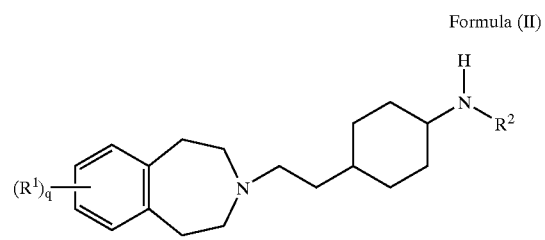

Formula (II)

wherein R¹, R², and q are as defined in claim 1, with a compound of formula (III):

A—COX          Formula (III)

wherein A is as defined in claim 1 and X is a halogen atom or the residue of an activated ester; or (b) reacting a compound of formula (II) with a compound A—Br, or A—I, or A—OSO₂CF₃ in the presence of carbon monoxide and a catalyst; or (c) preparing a compound of formula (I) wherein R¹ is Ar³—Z and Z is a bond, by reacting a compound of formula (IV):

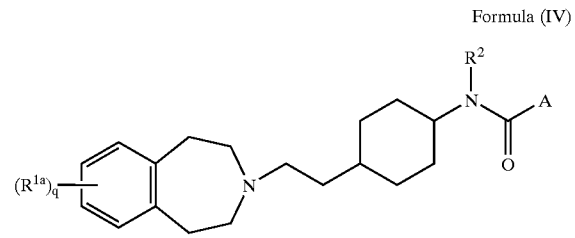

Formula (IV)

wherein A, R², and q are as defined in claim 1, one $R^{1a}$ represents a group W wherein W is a halogen atom or a trifluoromethylsulfonyloxy group, or W is a group M selected from a boron derivative or a metal function, and when q is 2 the other $R^{1a}$ is R¹ as defined in claim 1;

with a compound Ar³—W¹, wherein W¹ is a halogen atom or a trifluoromethylsulfonyloxy group when W is a group M, or W¹ is a group M as defined above when W is a halogen atom or a trifluoromethylsulfonyloxy group; or (d) preparing a compound of formula (I) wherein R¹ is Ar³—Z and Z is O or S, by reacting a compound of formula (V):

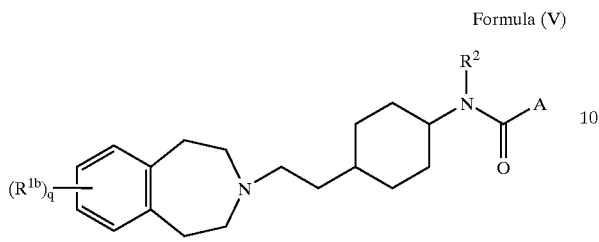

Formula (V)

wherein A, R², and q are as defined in claim 1, one R^{1b} represents a group ZH and when q is 2 the other R^{1b} represents R¹ as defined in claim 1;
with a reagent serving to introduce the group Ar³; or (e) preparing a compound of formula (I) where A represents a group a formula (b) and Y is a bond, reaction of a compound of formula (VI):

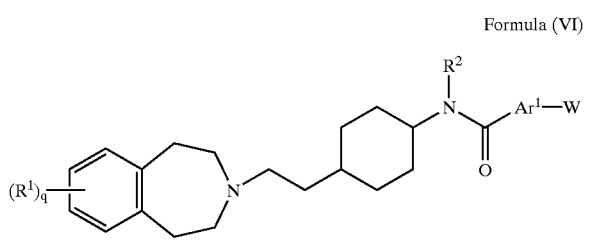

Formula (VI)

wherein R¹, R², q, and Ar¹ are as defined in claim 1 and W is as defined in (c) above,
with a compound Ar²—W¹, wherein W¹ is a halogen atom or a trifluoromethylsulfonyloxy group when W is a group M, or W¹ is a group M as defined in (c) above when W is a halogen atom or a trifluoromethylsulfonyloxy group; or (f) interconversion of one compound of formula (I) to a different compound of formula (I) by (i) alkylation of a compound (I) wherein R² represents hydrogen; (ii) conversion of one R¹ from alkoxy to hydroxy; (iii) conversion of R¹ from hydroxy to sulfonyloxy; (iv) conversion of a compound wherein Y represents S to a compound wherein Y is $SO_2$; or (v) conversion of Y from CO to $CH_2$; or (g) separating cis- and trans-isomers of compounds of formula (I) by conventional methods;

and optionally thereafter forming a salt of the compound of formula (I).

17. A compound according to formula (I), wherein the compound is trans-3-(2-(1-(4-(3-(3-(5-Methyl)-1,2,4-oxadiazolyl)benzoyl)amino)-cyclohexyl)ethyl)-7-methylsulphonyl-2,3,4,5-tetrahydro-1H-3-benzazepine or a salt thereof.

18. A compound according to formula (I), wherein the compound is trans-3-(2-(1-(4-(3-(2-(4-Methyl)oxazolyl)benzoyl)amino)-cyclohexyl)ethyl)-7-methylsulphonyl-2,3,4,5-tetrahydro-1H-3-benzazepine or a salt thereof.

19. A compound according to formula (I), wherein the compound is trans-3-(2-(1-(4-(3-(2-(5-Methyl)oxazolyl)benzoyl)amino)-cyclohexyl)ethyl)-7-methylsulphonyloxy-2,3,4,5-tetrahydro-1H-3-benzazepine or a salt thereof.

20. A compound according to formula (I), wherein the compound is trans-(E)-7-(3-(5-Methyl)-1,2,4-oxadiazolyl)-3-(2-(1-(4-(3-(4-fluoro)phenylpropenoyl)amino)cyclohexyl)ethyl)-2,3,4,5-tetrahydro-1H-3-benzazepine, which is the compound of the formula

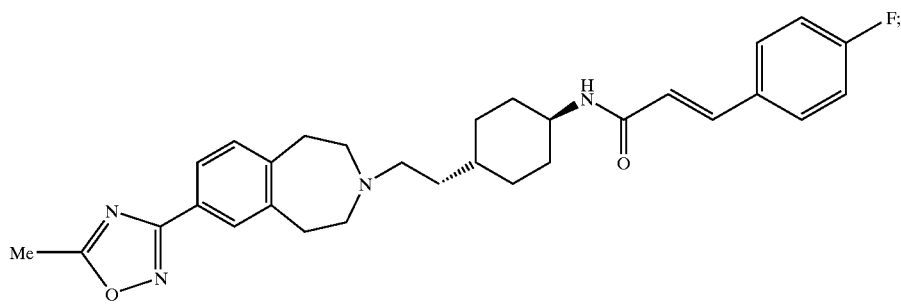

or a salt thereof.

21. A compound which is:

trans-3-(2-(1-(4-(N-tert-Butyloxycarbonyl)amino)cyclohexyl)ethyl)-7-methylsulphonyl-2,3,4,5-tetrahydro-1H-3-benzazepine, or trans-3-(2-(1-(4-Amino)cyclohexyl)ethyl)-7-methylsulphonyl-2,3,4,5-tetrahydro-1H-3-benzazepine.

* * * * *